United States Patent
Nielsen et al.

(10) Patent No.: US 12,351,817 B2
(45) Date of Patent: Jul. 8, 2025

(54) SYSTEMS AND METHODS FOR GENETIC ENGINEERING OF A POLYPLOID ORGANISM

(71) Applicants: David Nielsen, Tempe, AZ (US); Christopher Jones, Tempe, AZ (US)

(72) Inventors: David Nielsen, Tempe, AZ (US); Christopher Jones, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 18/389,738

(22) Filed: Dec. 19, 2023

(65) Prior Publication Data
US 2024/0158815 A1  May 16, 2024

Related U.S. Application Data

(62) Division of application No. 16/894,416, filed on Jun. 5, 2020, now Pat. No. 11,898,157.

(60) Provisional application No. 62/857,582, filed on Jun. 5, 2019.

(51) Int. Cl.
   *C12N 15/90*     (2006.01)
   *C12N 15/86*     (2006.01)
   *C12Q 1/6874*    (2018.01)
   *C12Q 1/6897*    (2018.01)

(52) U.S. Cl.
   CPC .......... *C12N 15/902* (2013.01); *C12N 15/86* (2013.01); *C12Q 1/6874* (2013.01); *C12Q 1/6897* (2013.01)

(58) Field of Classification Search
   None
   See application file for complete search history.

(56) References Cited

U.S. PATENT DOCUMENTS

| | | |
|---|---|---|
| 9,150,884 B2 | 10/2015 | Nielsen et al. |
| 9,944,955 B1 | 4/2018 | Wang et al. |
| 10,125,377 B2 | 11/2018 | Nielsen et al. |
| 10,174,346 B2 | 1/2019 | Nielsen et al. |
| 10,246,726 B2 | 4/2019 | Wang et al. |
| 10,844,405 B2 | 11/2020 | Nielsen et al. |
| 11,898,157 B2 * | 2/2024 | Nielsen ................ C12Q 1/6897 |
| 2007/0196334 A1 | 8/2007 | Khan |
| 2020/0216865 A1 | 7/2020 | Nielsen et al. |
| 2020/0231992 A1 | 7/2020 | Nielsen et al. |

FOREIGN PATENT DOCUMENTS

| | | |
|---|---|---|
| WO | 2012122333 A1 | 9/2012 |
| WO | 2013172928 A1 | 11/2013 |
| WO | 2015031048 A1 | 3/2015 |
| WO | 2015041776 A1 | 3/2015 |
| WO | 2019018302 A1 | 1/2019 |
| WO | 2019023019 A1 | 1/2019 |

OTHER PUBLICATIONS

Chica, et al., Curr Opin Biotechnol. Aug. 2005; 16(4):378-84 (Year: 2005).
Singh, et al., Curr Protein Pept Sci. 2017, 18, 1-11 (Year: 2017).
Crasto, et al., LINKER: a program to generate linker sequences for fusion proteins, Protein Eng., 2000, vol. 13, No. 5, pp. 3096-3312.
Dayhoff, Margaret O.; Eck, Richard V.; and National Biomedical Research Foundation, Atlas of Protein Sequence and Structure, vol. 3, National Biomedical Research Foundation, USA, 1996, 215 pages.
Lange, et al., Classical nuclear localization signals: definition, function, and interaction with importin alpha, J. Biol. Chem. 20007, vol. 282, No. 8, pp. 5101-5105.
Lombardo, et al., Gene editing in human stem cells using zince finger nucleases and integrase-defective lentiviral vector delivery, Nat. Biltechnology 2007, vol. 25, No. 11, pp. 1298-1306.
Moehle, et al., Targeted gene addition into a specified location in the human genome using designed zinc finger nucleases, Pro Natl Acad Sci, 2007, No. 9, pp. 3055-3060.
Santiago, et al., Targeted gene knockout in mammalian cells by using engineered zinc-finger nucleases, Pnas, 2008, vol. 105, No. 15, pp. 5809-5814.
Stevens, et al., The Production of Hydrogen Peroxide by Blue-Green Algae: A Survey, J. Phycol., 1973, vol. 9, pp. 427-430.
Taylor, et al., A High-throughput Platform for the Production and Analysis of Transgenic Cassave (*Manihot esculenta*) Plants, Tropical Plant Biology, 2012, vol. 5, pp. 127-139.
Urnov, et al., Highly efficient endogenous human gene correction using designed zinc-finger nucleases, Nature, 2005, vol. 435, pp. 646-651.
Gribskov, Nucl. Acids Res. 14(6):6745-6763 (1986).

* cited by examiner

*Primary Examiner* — Christian L Fronda
(74) *Attorney, Agent, or Firm* — Polsinelli PC

(57) ABSTRACT

Compositions and methods for genetically modifying at least one nucleic acid sequence of interest in a polyploid organism.

10 Claims, 24 Drawing Sheets
(18 of 24 Drawing Sheet(s) Filed in Color)
Specification includes a Sequence Listing.

wt7002

ΔglpK::loxP::gmR::loxP wt7002

ΔglpK::loxP::gmR::loxP

ΔglpK::loxP::gmR::loxP + Cre

Low CO2

Low light

High light

High CO2

Low light

High light

Patch 1

Patch 2 n/a

SEQUENCE LISTING

Sequence total quantity: 23
SEQ ID NO: 1            moltype = DNA   length = 5284
FEATURE               Location/Qualifiers
misc_feature        1..5284
                     note = SYNTHESIZED
source                1..5284
                     mol_type = other DNA
                     organism = synthetic construct
SEQUENCE: 1

```
gtgaatattt caccccccat tcaacttgtc gaagccccca cccaagcttt actgacctgg   60
gctaaggcga tcgccacggg caccccagac ccatttcagc gggggcaaca actgagtcag  120
aaattgggcg caacctatgg cagtgatggc ctaacccaaa taggattctg gattccggag  180
gtgggcgatc gccccgttta cctcgaaatt tttacgccca tggaggcaat cgattttcgc  240
cttgctgatc aagtcattcc gttccgtcgg gaggtgctag aactgccgcg ccagggggaa  300
tttgcctggg ccgttgtggc gggtctcaaa gctggcaccc gtacccaagc gggatcgttt  360
tactggttgc gcagtggtga acagattatc gcgatgtct tgcccactc tctgccctac  420
ggtgtgtttg cgccagccga gctgtacgac atggcgcaac tggagcgcga cagggccgac  480
cgcgactatt ttcaccagga aacttgggtc acaccgccgc gcaatatttt gcagattcat  540
gtgggtaccg cttcccccac gggcacccta gccggactca gccgcattta ccgtgacctc  600
gcccgcaaat tggccaatag ccaacccctc accgccgctg aaaaaaaacta tgtgggcttt  660
gatgcgattg aactgttacc cattgaaccc acggtgaat ttcgcccgc cgaaaatgaa  720
atgattcatg cttttttgca aattcgggcg atcaccaacc aagaagtgca agtccacctg  780
aaaaaaccag acacccaaaa ttggggctat gacgatctga ttttaggggc gcggccacc  840
agtcccgccc tcctcagtac cctcagaccc accgaagttg tggattttat tgccacgctc  900
cacactgcct ttgcccgccc gatccagatt attttttgacc tggtttatgg gcatatccat  960
caccaagccc tgggattaat caatgcgcga ttttttccggg ggcaaatat attggccat 1020
gatacaaacc agcaaaatcc gatggtgcgg gctgttctcc tggagttgca acggcgaaaa 1080
attaatctag gggccgatgg gattcgggtg gatggggtc aagattttca ggtgtccgac 1140
gccatttccg gccaactaga ctatgacaat gatttcctgc tgaagatggc tgcggtaccc 1200
caaaccgttg gtacagcgac tcgcgagttg tacaccattt atgaagatgg ccgcccctgg 1260
cccaatgtcg gttgggaaga tatggctacc catttggatt taatttacct aaagcccgat 1320
tgttttcagt ggagtccgtt gatcttcgag cataatacgc ccacgttaca gggattttgg 1380
caacgggaat ggcgggatgt gtgcaaaatt atggcccatg cgatcgctg ggtgaccggt 1440
tgcgccaacc atgacacggt acgcaagggc aaccacatca caccgccgc aattcggatt 1500
aatgaatatt taggggattc tttgccggaa attttacaaa atgcctacga taatccgaca 1560
acccaactgt ggatccatgg ctttagccca ggaattccga tggatttttt aaatgcatta 1620
atgcacactc cctggggctt ttttcggaat acagatgacc aatatgccgt caaaattatg 1680
gcggacgaaa ttggctttct ctattggcaa attacgccgg aaatttaccg acaatctggg 1740
gcgtttcggc ggtttaaaac catgggcttt tatgatctct cgttaatgcg gcagttcttt 1800
aaggcagtgg aacaggccat tgaagcgatt ggctatgatc taccaaagct ggcgattttt 1860
ctgcaaaccg aattagaacc acaatttgat ttttaaagc cgattaccat tgccaacctg 1920
aaggaaatag cgatcgcctt tatggaggat ggccacgagg cttgtcgggt ctcccattat 1980
tgtggatcgg taccggatga gcgggcgagc tttaatttac gcttgcggca atatcgccag 2040
```

```
gcccagcctt ggctgcgaaa tcatctcgat cctgcaaggg gcgatcgcct gcaccattgg  2100
tcggatcacc aacgcaccat tttctacggc aggcgcacca atcccgacac ccagcagcgg  2160
cttgtgttag tggcgcacat ggccggggct ccgaagaccg ttgagattgg caaatggctc  2220
gccctggatt tggatcgttg gcagttggcg atcgccacac cgactttgaa gatcaacacc  2280
atctatgact tagcccaaat tcacttgcac aatggcgaag gttttctgtt atctgaaatt  2340
cctccctaaa tgatgtcttt tgagcctaaa aacacacttt tttgacctaa tttaacccat  2400
ttaaaaaact ttatttaata atgaccatgg cccatcaaaa atacattctt gcgttagacc  2460
tcggtaccac tggtaatcgt gcccttttgt ttaaccacaa aggcgatatt gttgcccaag  2520
cctataaaga attaacccaa tattatcccc agccgggctg ggtcgaacat gatgcgacgg  2580
aaatttggaa cgacaccaaa gccgtcatgc aacaggtcgt caacaatagc agcattgaaa  2640
cccaggatat cgcggcgatc ggcctgacgg tgcagcggga aacctgtgtc ctctgggata  2700
aaaccactgg caaaccactt cataaagcaa ttgtctggca ggatcggcgg acggctcccc  2760
tctgtcaaac cctcagtgcg gcaggcaaag cggcagaaat ttacgataaa acgggcttgg  2820
tgttggatgc ttattttcg gcgacgaaac tgaattggat attaagctgg gctaaggaaa  2880
atagtgccat taaccccaat aatgtcctcg ctggaaccat tgacacctgg gccttgtgga  2940
acctcacggg aggcaaagtc cacgccacag atcacagtaa tgccagccgg acaatgttgc  3000
tcaatctcaa ccaaaaagat tgggatccgg atttgttgga tttattcgat attccccgcc  3060
agatgatgcc aacggtgcag tcgagcctag gggaatttgg caaaaccgat ccaagtttat  3120
tgggggcggc aattccgatc accgccatct ttggggatca acaggcgcc ctctatgccc  3180
atggttgcga tcgccccggc ttattaaaat gcacctatgg cacaggggcg ttttttggtgg  3240
cgcacacggg cgacgagatt aaacgctcca acataagct cctaacgacc atcgcgcaac  3300
cattggatac aagcccatca cgatggcaca aatctcgata ttggctatgc cctcgaaggg  3360
agtatgttca ccgctgggc ttgtatccaa tggttgcgcg atggcctaca aattatcgaa  3420
acggcggcgg aaacgaatga tcttgcccaa ggggtgaatg ataatggcgg cgcttatttt  3480
gttccggctt taagtggtct gggagcgccc cactgggata tgagtgccag gggcgcattt  3540
ctgggtttaa cgagagggcgt caaaaaagaa cacatgcgtcct agaggcgatc  3600
gcctaccaag ccaaagaagt agtcgaagcg attaaccaag attccggtac gccgatccaa  3660
gaattaaaag tcgatggcgg cgcgtgcaat aacgactttc tgatgcaatt ccaagctgac  3720
gtgttgggta ttcccgtgga acgtcccgct gtcctcgatg ccacgcccca gggggcagcc  3780
tttgccgctg gattagctgt cggttttttgg gatgattacc aaaccctggt gcaaaaccgc  3840
aaaattgatt acgtctttaa gcccagtgcc aacgcctccc aagcccaagc ccatttcaaa  3900
gtctggcaaa aagccgttga acgagcgaaa aactgggcct aaccccctct tgcctacagc  3960
atctcccccca ggggagaatt cttcctgttt caactccctc taacgtaaac ccattgaatt  4020
taaaaaagac tttatgactg cttttactgct ccatgaccaa cattattccc ttgatcatga  4080
agccttctct caaccctca gcaacacaga aaatttactc attattcaag atctagatgg  4140
cgtttgcatg gggttagtca aagacccctt aacccgcaaa attgatcctg actatatccg  4200
cgccacacgc aagtttagag accttcttc tgtcctcacc aacggtgaac atgaaggcag  4260
aaggggagta aatcgcatcg ttgaacgggc atttcgcaat gttgaagcca aaggagaaac  4320
aagtcatttta cctggtttag cagcaggggg tgtgcaaatg cagacagata atggccaaat  4380
ttcccatccc ggtgttagcc aagcagaact cgatttcctt gccacagtgc cagatttaat  4440
tggtcaaagt ttaggacaat ttttactaa atatgttgat atttttcccg ctgagcttca  4500
acctgagctg atccatgctt ctgtttaga taatctcgtt tcaccgacgg caaatttaaa  4560
cgtcctggcc gaatatttag gcgatcgcct tgagatttac caagacctcc agcgcaccat  4620
ggaaaccctg atgaatgatt tgctagaaaa agctggccaa cagggtttag acaatagttt  4680
tttcgtgcac tatgcgccca atttaggcag agataatgtg gggaaagaaa ttgtccgctt  4740
tgccacagcc aaggattctg gcaccacaga ttttcagttt atggtgtgtg gtgccgtcaa  4800
agaagcgggg gttttagtgc tgctgaatta ttactatgcc caacgcacgg gccactatcc  4860
cctaggagaa acctttaacg cccgccaagc gccccaaaac cacgaggaac tattgcaact  4920
ggtgcaaagac aatttcgatc cgcaattgat gcctttaatc gttggcgtcg gcgatacggt  4980
cacaagtcac accgaaggcg atcaagttcg acggggggg agcgatcgcc tattcctgca  5040
gctcgtccaa gacattggta aatgggcaaa gagcggcaat ctcgtcgtgt atatcgacag  5100
ctcccaggga gaattaaaaa atcggattcc cttaaaactg gggacaatca atggtcaaac  5160
ccaagtgatt gagggcatta ctgatccggc tgatccgtta caaattaacg ttgcttttcc  5220
gggcgggttt gaacaataca ccgcccttttt tcagcaggcc gccgcaaacc gatctggaac  5280
atag                                                                5284

SEQ ID NO: 2            moltype = DNA   length = 19
FEATURE                 Location/Qualifiers
misc_feature            1..19
                        note = SYNTHESIZED
source                  1..19
                        mol_type = other DNA
                        organism = synthetic construct
SEQUENCE: 2
catctcgatc ctgcaaggg                                                 19

SEQ ID NO: 3            moltype = DNA   length = 20
FEATURE                 Location/Qualifiers
misc_feature            1..20
                        note = SYNTHESIZED
source                  1..20
                        mol_type = other DNA
                        organism = synthetic construct
SEQUENCE: 3
aaccaattca gtttcgtcgc                                                20

SEQ ID NO: 4            moltype = DNA   length = 4669
FEATURE                 Location/Qualifiers
misc_feature            1..4669
```

```
                        note = SYNTHESIZED
source                  1..4669
                        mol_type = other DNA
                        organism = synthetic construct
SEQUENCE: 4
gtgaatattt cacccccat  tcaacttgtc gaagccccca cccaagcttt actgacctgg    60
gctaaggcga tcgccacggg caccccagac ccatttcagc gggggcaaca actgagtcag   120
aaattgggcg caacctatgg cagtgatggc ctaacccaaa taggattctg gattccggag   180
gtgggcgatc gccccgttta cctcgaaatt tttacgccca tggaggcaat cgattttcgc   240
cttgctgatc aagtcattcc gttccgtcgg gaggtgctag aactgccgcg ccaggggaa    300
tttgcctggg ccgttgtggc gggtctcaaa gctggcaccc gtacccaagc gggatcgttt   360
tactggttgc gcagtggtga acagattatc cgcgatgtct tgcccactc  tctgccctac   420
ggtgtgtttg cgccagccga gctgtacgac atggcgaac  tggagcgcga cagggccgac   480
cgcgactatt ttcaccagga aacttgggtc acaccgcccc gcaatatttt gcagattcat   540
gtgggtaccg cttcccccac gggcacccta gccggactca gccgcattta ccgtgacctc   600
gcccgcaaat tggccaatag ccaacccctc accgccgctg aaaaaaacta tgtgggcttt   660
gatgcgattg aactgttacc cattgaaccc acggtggaat tcgccccgc  cgaaaatgaa   720
atgattcatg cttttggca  aattcgggcg atcaccaacc aagaagtgca agtccacctg   780
aaaaaaccag acacccaaaa ttggggctat gacgatctga ttttaggggc cgcggccacc   840
agtcccgccc tcctcagtac cctcagaccc accgaagttg tggattttat tgccacgctc   900
cacactgcct ttgcccgccc gatccagatt atttttgacc tggtttatgg gcatatccat   960
caccaagccc tgggattaat caatgcgcga tttttccggg gcgcaaatat gtatggccat  1020
gatacaaacc agcaaaatcc gatggtgcgg gctgttctcc tggagttgca acggcgaaaa  1080
attaatctag gggccgatgg gattcgggtg gatggggtc  aagattttca ggtgtccgac  1140
gccatttccg gccaactaga ctatgacaat gatttcctgc tgaagatggc tgcggtaccc  1200
caaaccgttg gtacagcgac tcgcgagttg tacaccattc atgaagatgg ccgcccctgg  1260
cccaatgtcg gttgggaaga tatgctacc  catttggatt taatttacct aaagcccgat  1320
tgttttcagt ggagtccgtt gatcttcgag cataatacgc ccacgttaca gggattttgg  1380
caacgggaat ggcgggatgt gtgcaaaatt atggcccatg cgatcgctg  ggtgaccggt  1440
tgcgccaacc atgacacggt acgcaagggc aaccacatca caaccgccgc aattcggatt  1500
aatgaatatt tagggaattc tttgccggaa attttacaaa atgcctacga taatccagca  1560
acccaactgt ggatccatgg ctttagccca ggaattccga tggatttttt aaatgcatta  1620
atgcacactc cctggggctt ttttcggaat acagatgacc aatatgccgt caaaattatg  1680
gcggacgaaa ttggctttct ctattggcaa attacgccgg aaatttaccg acaatcctga  1740
gcgtttcggc ggtttaaaac catgggcttt tatgatctct cgttaatgcg gcagttcttt  1800
aaggcagtgg aacaggccat gaagcgatt  ggctatgatc taccaaagct ggcgattttt  1860
ctgcaaaccg aattagaacc acaatttgat ttttaaagc  cgattaccat tgccaacctg  1920
aaggaaatag cgatcgcctt tatggaggat ggccacgagg cttgtcgggt ctcccattat  1980
tgtgatcgg  taccggatga gcgggcgagc tttaatttac gcttgcggca atatcgccag  2040
gcccagcctt ggctgcgaaa tcatctcgat cctgcaaggg gcgatcgcct gcaccattgg  2100
tcggatcacc aacgcaccat tttctacggc aggcgcacca atcccgacac ccagcagcgg  2160
cttgtgttag tggcgcacat ggccgggct  ccgaagaccg ttgagattgg caaatggctc  2220
gccctggatt tggatcgttg gcagttggcg atcgccaacc cgacttttgaa gatcaacacc  2280
atctatgact tagcccaaat tcacttgcac aatggcgaag  gttttctgtt atctgaaatt  2340
cctccctaaa tgatgtcttt tgagcctaaa aacacacttt tttgacctaa tttaacccat  2400
aacttcgtat aatgtatgct atacgaagtt atccctaggc gcagcggccg ctactagtac  2460
aacaaagcca cgttgtgtct caaaatctct gatgttacat tgcacaagat aaaaatatat  2520
catcatgaac aataaaactg tctgcttaca taaacagtaa tacaagggg  gttatgttac  2580
gcagcagcaa cgatgttacg cagcagggca gtcgccctaa aacaaagtta ggtggctcaa  2640
gtatgggcat cattcgcaca tgtaggctcg gccctgacca agtcaaatcc atgcgggctg  2700
ctcttgatct tttcggtcgt gagttcgag  acgtagccac ctactcccaa catcagccgg  2760
actccgatta cctcgggaac ttgctccgta gtaagacatt catcgcgctt gctgccttcg  2820
accaagaagc ggttgttggc gctctcgcgg cttacgttct gcccaggttt gagcagccgc  2880
gtagtgagat ctatatctat gatctcgcag tctccggcga gcaccggagg cagggcattg  2940
ccaccgcgct catcaatctc ctcaagcatg aggccaacgc gcttggtgct tatgtgatct  3000
acgtgcaagc agattacggt gacgatcccg cagtggctct ctatacaaag ttgggcatac  3060
gggaagaagt gatgcacttt gatatcgacc aagtaccgc  cacctaatca gaattggtta  3120
attggttgta acactggcag agcctctagt atataaacgc agaaaggccc acccgaaggt  3180
gagccagtgt gactctagta gagagcgttc accgacaaac aacagataaa acgaaaggcc  3240
cagtctttcg actgagcctt tcgttttatt tgatgcctgg ctctagtctc gagataactt  3300
cgtataatgt atgctatacg aagttatccc cctcttgcct acagcatctc ccccagggga  3360
gaattcttcc tgtttcaact ccctctaacg taaacccatt gaatttaaaa aagacttat   3420
gactgcttta ctgctccatg accaacatta ttcccttgat catgaagcct ttctctcaac  3480
cctcagcaac acagaaaatt tactcattat tcaagatcta gatgcgtt  gcatggggtt  3540
agtcaaagac cccttaaccc gcaaaattga tcctgactat atccgcgcca cacgcaagtt  3600
tagagaccac ttctttgtcc tcaccaacgg tgaacatgaa ggcagaaggg gagtaaatcg  3660
catcgttgaa cgggcatttc gcaatgttga agccaaagag gaaacaagct atttacctgg  3720
tttagcagca gggggtgtgc aatggcagac agataatggc caaatttccc atcccggtgt  3780
tagccaagca gaactcgatt tccttgccac agtgccaagt ttaattggtc aaagtttagg  3840
acaattttt  actaaatatg ttgatatttt tcccgctgag cttcaacctg agctgatcca  3900
tgcttctgtt ttagataatc tcgtttcacc gacggcaaat ttaaacgtcc tggccgaata  3960
tttaggcgat cgccttgaga tttaccaaga cctccagcgc accatggaaa ccctgatgaa  4020
tgattttgcta gaaaaagctg gccaacaggg tttagacaat agttttttcg tgcactatgc  4080
gcccaattta ggcagagata atgtgggaaa agaaattgtc gcgtttgcca cagccaagga  4140
ttctggcacc acagattttc agtttatggt gtgtggtgcc gtcaaagaag cggggggttt   4200
agtgctgctg aattattact atgcccaacg cacgggccac tatccctag  gagaaacctt  4260
taacgcccgc caagcgcccc aaaaccacga ggaactattg caactggtgc aagacaattt  4320
cgatccgcaa ttgatgcctt taatcgttgg cgtcggcgat acggtcacaa gtcacaccga  4380
aggcgatcaa gttcgacggg gggggagcga tcgcctattc ctgcagctcg tccaagacat  4440
```

```
tggtaaatgg gcaaagagcg gcaatctcgt cgtgtatatc gacagctccc agggagaatt    4500
aaaaaatcgg attcccttaa aactggggac aatcaatggt caaacccaag tgattgaggg    4560
cattactgat ccggctgatc cgttacaaat taacgttgct tttccgggcg ggtttgaaca    4620
atacaccgcc cttttttcagc aggccgccgc aaaccgatct ggaacatag                4669

SEQ ID NO: 5           moltype = DNA  length = 19
FEATURE                Location/Qualifiers
misc_feature           1..19
                       note = SYNTHESIZED
source                 1..19
                       mol_type = other DNA
                       organism = synthetic construct
SEQUENCE: 5
catctcgatc ctgcaaggg                                                   19

SEQ ID NO: 6           moltype = DNA  length = 20
FEATURE                Location/Qualifiers
misc_feature           1..20
                       note = SYNTHESIZED
source                 1..20
                       mol_type = other DNA
                       organism = synthetic construct
SEQUENCE: 6
caagcgcgat gaatgtctta                                                  20

SEQ ID NO: 7           moltype = DNA  length = 19
FEATURE                Location/Qualifiers
misc_feature           1..19
                       note = SYNTHESIZED
source                 1..19
                       mol_type = other DNA
                       organism = synthetic construct
SEQUENCE: 7
catctcgatc ctgcaaggg                                                   19

SEQ ID NO: 8           moltype = DNA  length = 20
FEATURE                Location/Qualifiers
misc_feature           1..20
                       note = SYNTHESIZED
source                 1..20
                       mol_type = other DNA
                       organism = synthetic construct
SEQUENCE: 8
caagcgcgat gaatgtctta                                                  20

SEQ ID NO: 9           moltype = DNA  length = 6001
FEATURE                Location/Qualifiers
misc_feature           1..6001
                       note = SYNTHESIZED
source                 1..6001
                       mol_type = other DNA
                       organism = synthetic construct
SEQUENCE: 9
aacacgccag cactcgccgt tttaaaaccc agtcttggct aggggcaggc tttgtggagg      60
gtcattctgc taatcagatt ttggcaaata tccaggcagt cgccgcccag ttccccaacg    120
aatatgtcca gttaatcgcc gttgacccca actccaaaac acgggccgca gagatcatca    180
tccaacgccc tggcaacaat gcgcctgtcc agacagcaac cgcaaccagt agttttttcgg   240
gaggcacgaa agcagcccca agcagcaatg gtttcggggg tcacagtagc gggagtctca    300
gtggggatgt ggttttctaaa gtccgttcgc ttttgatgca aggctacaag attggaacag    360
aacacgccga taagcgccgt ttccgtgtta agtcctggag tagttgtggc accattgaca    420
gcacccaaga ggcagaagtt ttacgtcacc tcgaaggttg tctccaggag cacagtggcg    480
aatatgtccg catgattggt gtcgatgaag cggctaaacg acgggtgctt gaggaaatta    540
tccaacgccc ctaggttgtg taacgcgacc acttcgttat gggggagaaa acgaatgtct    600
atccccaaac ccttaccccca cctgtgatta attgaatcac cgttgacaga atcattgtga    660
ctttccaggc aattacccat ccagatattc aaattagtgg cgatgtaagg attcatcccc    720
gtgcggttat tgccccggt gttattctgc aagcaaccga aggcaattat gtggcgatcg    780
ccactggtgc ttgtattggt gcaggtgcga ttatccaggc ccacggcggc aacatcgaga    840
tccatgccgg cgcgattatc ggggcaggct gcctgatcat tggccaatgc tcagtgggag    900
aaaatgccctg cttaggttat ggctctaccc tattcaagc gcgatcgcc gccgccgaca    960
ttctcccgcc ccaaagcctc atcggcgatc cgtcccgcca agaaccacc gcttcttacc   1020
agactcaacc gccaaaaccc gcgaatcaat cgacaaccca acccctcgat ccttggcagg   1080
cagaagatac aactaaccag actgccacaa ccttttcgcc accagggcga tcgcccacta   1140
gcagcagcaa tcgtcccaat gtccagcccc accagaagc aggatcccct ccaactgaaa   1200
caccaaacac cgaagtgatg ccgacggttc cagaatcaaa ggaatcccta gaatcgggcg   1260
aaaaaacacc agttgtcggg caagtttata tcaatcaact attaatgacc ctattccctc   1320
accaaaattc tctcaatacc ccaaatcaac cagatgagcc ttagccccac aaaactttca   1380
tgattgcttg agtgaaaatt aaatgtttaa agttcttaaa ggagattgtt gagaaacata   1440
aatacttaat tcatctcatt tgaacgcttt ccctctctaa agatcccgac agaaaacggt   1500
tttagcccaa tgtctcatta ggtagcatgg ctgaattcga gcgggatttt atggcttttt   1560
```

```
taggtatttt tgtaagggta aaataggccc atcaaacagc attagaaatg ctaatcagcc   1620
caaaaaacaa aagcaatctt ttttttgttgc taaaagataa aaataagtcg aggctgtggt   1680
aacatatccc acagattaaa gaaagtcata agacttgaat cttcagaatt ttaaaaagca   1740
gttttgccaa cgtaagattt ttgaagtttt cgaccaacaa taccgttact ggtatttgtc   1800
tgttaaagat aagcatttt gctggaggaa aaccgcatgg ttcagaccaa atctgctggg   1860
tttaatgccg gtgtacagga ctaccgcctg acttactaca cccccgatta cacccccgaaa   1920
gataccgact tactcgcttg tttccggatg actcccaac ctggagtccc ccccgaagaa   1980
tgtgctgcgg ctgttgcggc tgaatcttct accggtactt ggaccactgt atggaccgat   2040
ggtttaactg acctcgaccg ctacaagggt cgttgctaca atgttgaacc cgttcccggt   2100
gaagacaacc aatatttctg tttcgttgct taccccctcg atctgttga agaaggttct   2160
gtaaccaacg ttttgacttc cttggttggt aacgtattcg gttttaaagc gctgcgtgcc   2220
ctgcgcctcg aagatatccg cttccccgtt gcgttaatca aaacttacca agggcctccc   2280
cacgggatca ctgtagagcg tgacctcctc aacaagtatg gtcgtcctct cctcggttgt   2340
acgattaagc cgaagctcgg tctgtctgcg aagaactacg gtcgtgcggt ttatgaatgt   2400
ctccgtggtg gtcttgactt caccaaagat gacgaaaaca tcaactctca gcctttcatg   2460
cgttggcgcg atcgcttcct gttcgttcaa gaagctatcg aaaaatccca agctgaaacc   2520
aacgaagtta agggtcacta ccttaacgtc accgctggca cttgcgaaga aatgctcaag   2580
cgggctgaat tcgctaagga aatcggcact cccatcatca tgcgacactt cttaactggt   2640
ggtttcactg cgaatactac ccttgcgaag tggtgtcgtg ataacggcgt tctgctccac   2700
atccaccggg caatgcacgc ggtaatcgac cgtcagaaga accacggtat tcacttccgc   2760
gttctcgcta agtgtctccg cctctctggt ggtgaccacc tccactccgg tacggttgtt   2820
ggtaagctcg aaggcgatcg cgccgccacc ctcggttttcg tagacctgat gcgtgaagac   2880
tacgttgaag aagatcgttc tcgcggtgta ttcttcaccc aagactacgc ttctctcccc   2940
ggcaccatgc ctgtggcttc cggtggtatc cacgtatggc acatgcctgc cctcgttgaa   3000
atcttcggcc acgattcctg cctccagttt ggtggtggta ccctcggtca cccctggggt   3060
aacgcacctg gtgcaactgc aaaccgtgtt gctctgaagc cttgtgttca agctcgtaac   3120
gaaggtcgca gcctgcccg tgaaggtaat gatgtcctcc gtgaagcagg taagtggtcg   3180
cctgaattgg cagccgccct cgacctgtgg aaggaaatca agttcgaatt cgataccgtt   3240
gacactctct aagctcctga tgagcatcag tggatgggga agtttgtcac aatctaccta   3300
ttcactgatg atttcctccc atggagttta aaaaagttgg gaaggaaacg gccatcactt   3360
tgcaaagcta tttgacctac caagcggtgc gtctaattag tcagcagctt agtgaaacca   3420
atcctggaca ggcgatttgg ctaggagagt tctctaaacg tcatccaatt caggaaagtg   3480
atctttacct cgaagcgatg atgctagaaa acaaagagct cgtcctcaga atcctgacgg   3540
tgcgagaaaa ccttgcggaa ggagttctgg agtttttgcc agaaatggtc ctcagccaaa   3600
tcaagcagtc caatggaaac catcgccgtt ctttattaga gcgtttaact caagttgatt   3660
cttcatcaac tgatcagact gaacctaacc ctggtgagtc tgatacttca gaagattctg   3720
aataaacttt gatccgataa agaggacata aatcaatgaa aactttacct aaagaaaagc   3780
gttacgaaac tctttcttac ttgccccccc tcagcgacca gcaaatcgct cgccaagtcc   3840
agtacatgat ggatcaaggc tatattcctg gtatcgatgt cgaaaaagat ccgactcctg   3900
aactccacca ctggacactg tggaagctgc ccctttttcaa cgcaagctct gctcaagaag   3960
tactcaacga agtgcgtgag tgcgtagtg aatattctga ctgctacatc cgtgttgttg   4020
gtttcgacaa catcaagcag tgccaaaccg ttagcttcat cgtttacaag cccaaccaaa   4080
cccgttaacta aggttttgtt ggttttttgtg acctgaattt aatttgaatc atgcggaatg   4140
cgatcgcctt aggacggtcg catttttttgt ttacgtctaa aattagtcga aatcccccat   4200
caacgccatg gtagtgattt tgtcttaacg ttattcaccc atcaatttca aaatgaacct   4260
gaagtttctt aaatctctct gggctacggc ggcgatcgcc tttgccatta gcgtaaatcc   4320
gagccttgtc tttgctgaaa cggaaccccc aagcgaaacc aaaactgccc tgatcaatga   4380
actccgcacc ttaactttcc gggatgaaaa cgcgacccag attttggact tgatgctgca   4440
acagatccaa gctcaatcca ccaccatggg cgatggcttt tgggtgaag aaacagatcc   4500
cgaaaccctg gccgctatcc aagaaagtgt caccgcatc accgaccgca tttatacccct   4560
gatgcaagac agaattgatt tcgttgccct ccagcggact cgactttca agctctatca   4620
cgaatatttc accgaagccg aactccaaga tttaatcacc ttctataaaa caccaccgg   4680
acaaaagact gccgcaactt ttccagaact tacagaacgc tccacagccc tctttagtga   4740
gcagctagcc ccagccatga tagaaattac ccaacaggtg atgttagaag aatttgcctc   4800
tgcctttgca acgttcgatg ctccagaaac tgaagcgcct gaaaattcgg agtcggctga   4860
agcagaagcc atcgattaaa cagagttgcg gatggatctg tgtaatcatc ctgaaacttc   4920
tacagatccc gcaaattacc aaccaagata attgaattcc catcatctc atcatggcaa   4980
cggacggctt tcttcagata ttgctcgcct ttctcattgg gaacacacaa tttacttttt   5040
ttgccaaact tgagccttaa tcgcgccagt ccccatgggt gagaaagccg cactagaatg   5100
attctagaga agtgagattc gaggggaatt tttaagatga aaaaacgagt gactctgaca   5160
tttccccagg acacggtgca aatgcccgtc acctatcgct tggcaaagga ttttaatatt   5220
gcggcgaata tcatccgcgc ccaggtcgct ccaaaccagg tgggcaagtt ggtggtggaa   5280
ctccaggggg atattgatgc cattgagatg gccttgaat ggatgaaagg caaggggatt   5340
ttagtttccc tcgcgagcaa agaaattgtg attaacgaaa atattgtgt ggattgtgct   5400
ctctgtacag gggtttgtcc gacgggagca ttatcgctag atcccaaac gtttcgacta   5460
aaatttaccc gccaaaaatg tgtggttttgc gaacagtgtt tacccgcttg tccggtccag   5520
gcgatcgcca caaattttta aggtaccttc ccaaaaaaaa gtgctgttgg cggtgatgaa   5580
atcaacccaa agattgcaat tgttaatgag agtgattata aattctgttg aaaaatgtat   5640
ttaaaggtag aaaccattgt gtttttaagct ttttgggtct gttttggagca attaagaaga   5700
ttattctagg ccagagcatc ccttaggata ttgttaggaa ttcctaactt tttaattctt   5760
catgaaaaaa caggccaacg ttcagcgtca cacagagccc gcagatcaga atttgcggct   5820
aaaaagtcat ggcaatttat tttattttatt ggctgtggcg gcgggcttga tttttttaca   5880
gggttacatg attgcgccct taattcccccg tttatcggag attttttggcg ttttctgtcca   5940
ggaaattggc tttattgtgc cgatttatat gctgtcctac gctgtcatgg ctctttttta   6000
t                                                                  6001

SEQ ID NO: 10       moltype = DNA   length = 20
FEATURE             Location/Qualifiers
misc_feature        1..20
```

```
                        note = SYNTHESIZED
source                  1..20
                        mol_type = other DNA
                        organism = synthetic construct
SEQUENCE: 10
aattcgagcg ggattttatg                                                        20

SEQ ID NO: 11           moltype = DNA   length = 20
FEATURE                 Location/Qualifiers
misc_feature            1..20
                        note = SYNTHESIZED
source                  1..20
                        mol_type = other DNA
                        organism = synthetic construct
SEQUENCE: 11
gggaagcgga tatcttcgag                                                        20

SEQ ID NO: 12           moltype = DNA   length = 6068
FEATURE                 Location/Qualifiers
misc_feature            1..6068
                        note = SYNTHESIZED
source                  1..6068
                        mol_type = other DNA
                        organism = synthetic construct
SEQUENCE: 12
aacacgccag cactcgccgt tttaaaaccc agtcttggct aggggcaggc tttgtggagg            60
gtcattctgc taatcagatt ttggcaaata tccaggcgat cgccgcccag ttccccaacg            120
aatatgtcca gttaatcgcc gttgacccca actccaaaac acgggccgca gagatcatca            180
tccaacgccc tggcaacaat gcgcctgtcc agacagcaac cgcaaccagt agttttcgg             240
gaggcacgaa agcagcccca agcagcaatg gttcgggg tcacagtagc gggagtctca             300
gtggggatgt ggtttctaaa gtccgttcgc ttttgatgca aggctacaag attggaacag            360
aacacgccga taagcgccgt ttccgtgtta agtcctggag tagttgtggc accattgaca            420
gcacccaaga ggcagaagtt ttacgtcacc tcgaaggttg tctccaggag cacagtggcg            480
aatatgtccg catgattggt gtcgatgaag cggctaaacg acgggtgctt gaggaaatta            540
tccaacgccc ctaggttgtg taacgcgacc acttcgttat gggggagaaa acgaatgtct            600
atccccccaac ccttacccca cctgtgatta ttgaatcac cgttgacaga atcattgtga            660
cttccaggc aattacccat ccagatattc aaattagtgg cgatgtaagg attcatcccc             720
gtgcgggtat tgccccgcgt gttattctgc aagcaaccga aggcaattat gtggcgatcg            780
ccactggtgc ttgtattggt gcaggtgcga ttatccagac ccacgccgcg aacatcgaag            840
tccatgccgg cgcgattatc ggggcaggct gcctgatcat tggccaatgc tcagtgggag            900
aaaatgcctg cttaggttat ggctctaccc tatttcaagc ggcgatcgcc gccgccgcaa            960
ttctcccgcc ccaaagcctc atcggcgatc cgtcccgcca agaaaccacc gcttcttacc            1020
agactcaacc gccaaaaccc gcgaatcaat cgacaaccca acccctcgat ccttggcagg            1080
cagaagatac aactaaccag actgccacaa ccttttcgcc accagggcga tcgcccacta           1140
gcagcagcaa tcgtcccaat gtccagcccc accagaagc aggatcccct ccaactgaaa            1200
caccaaaacac cgaagtgatg ccgacggttc cagaatcaaa ggaatcccta gatcgggcg           1260
aaaaaacacc agttgtcggg caagtttata tcaatcaact attaatgacc ctattccctc            1320
accaaaattc tctcaatacc ccaaatcaac cagatgagcc ttagccccac aaaactttca            1380
tgattgcttg agtgaaaatt aaatgtttaa agttcttaaa ggagattgtt gagaaacata          1440
aatacttaat tcatctcatt tgaacgcttt ccctctctaa agatcccgac agaaaacggt         1500
tttagcccaa tgtctcatta ggtagcatgg ctgaattcga gcgggatttt atggctttt           1560
taggtatttt tgtaagggta aatagggccc atcaaacagc attagaaatg ctaatcagcc          1620
caaaaaacaa agcaatcttt ttttgttgc taaaagataa aaataagtcg aggctgtggt           1680
aacatatccc acagattaaa gaaagtcata agacttgaat cttcagaatt ttaaaaagca          1740
gttttgccaa cgtaagattt ttgaagtttt cgaccaacaa taccgttact ggtatttgtc         1800
tgttaaagat aagcatttt gctggaggaa aaccgcatgg ttcagaccaa atctgctggg          1860
tttaatgccg gttccaacct gctgacggtg caccagaatc tgccggcact gccggtcgat          1920
gcaaccagtg acgaagtgcg caaaaatctg atggatatgt ttcgtgaccg ccaagccttc         1980
agcaacatat cgtggaaaat gctgctgtcg gtttgccgta gctggggcgc ctgtctgtaaa         2040
ctgaacaatc gcaaatggtt tccggcagaa ccggaagatg tgcgtgacta tctgctgtac         2100
ctgcaggcac gtggtctggc agttaaaacc atccagcaac atctggggcca actgaacatg        2160
ctgcaccgtc gctctggtct gccgcgtccg agtgattcca atgccgtcag tctggtgatg          2220
cgtcgcattc gtaaagaaaa cgtggatgca ggcgaacgcg ctaaacaggc actggctttt         2280
gaacgtaccg atttcgacca agttcgctct ctgatgaaca acagtgatgc ttgccagaag        2340
atccgcaatc tggcattcct gggtattgct tataacaccc tgctgcgcat tgcagaaatc       2400
gctcgtattc gcgtgaaaga tatcagccgt acggacggcg tcgcatgct gattcacatc         2460
ggccgtacca aaacgctggt ttccaccgcg ggcgtcgaaa agccctgtc actgggtgtc          2520
acgaaactgg tggaacgctg gatttcagtt tcgggcgtcg cagatgaccc gaacaattac        2580
ctgttttgtc tgtgtgcgcaa aatggttgtt gcagctccga tgcgtacctc tcagctgagt      2640
acgcgtgcgc tggaaggcat cttcgaagcc acccatcgcc tgatttatgg cgcgaaagat        2700
gacagcggtc agcgttacct ggcatggtcc ggtcactcag ctcgtgttgg tgcagcacgt       2760
gatatgcac gtgcaggtgt ctctatcccg gaaattatgc aggccggcgg ttggacgaac         2820
gtgaatattg ttatgaacta tattcgtaac ctggactctg aaacgggtgc gatggtcgt         2880
ctgctggaag atgcgcagga acgaggggcgg tgctttggca ggatccggct gctaacaaag      2940
cccgaaagga agctgagttg gctgctgcca ccgctgagca ataactagca taaccccttg         3000
gggcctctaa acgggtcttg acggtttt tgtctagatc aacggcctca acctactact            3060
gggcaacaaa gccacgttgt gtctcaaaat ctctgatgtt acattgcaca agataaaaat         3120
atatcatcat gaacaataaa actgtctgct tacataaaca gtaatacaag gggtgttatg         3180
agccatattc aacgggaaac gtcttgctcc aggccgcgat taaattccaa catggatgct        3240
```

```
gatttatatg ggtataaatg ggctcgcgat aatgtcgggc aatcaggtgc gacaatctat   3300
cgattgtatg ggaagcccga tgcgccagag ttgtttctga acatggcaa aggtagcgtt    3360
gccaatgatg ttacagatga gatggtcaga ctaaactggc tgacggaatt tatgcctctt   3420
ccgaccatca agcattttat ccgtactcct gatgatgcat ggttactcac cactgcgatc   3480
cccggaaaa cagcattcca ggtattagaa gaatatcctg attcaggtga aaatattgtt    3540
gatgcgctgg cagtgttcct gcgccggttg cattcgattc ctgtttgtaa ttgtcctttt   3600
aacagcgatc gcgtatttcg tctcgctcag gcgcaatcac gaatgaataa cggtttggtt   3660
gatgcgagtg attttgatga cgagcgtaat ggctggcctg ttgaacaagt ctggaaagaa   3720
atgcataagc ttttgccatt ctcaccggat tcagtcgtca ctcatggtga tttctcactt   3780
gataaccttta ttttgacga ggggaaatta ataggttgta ttgatgttgg acgagtcgga   3840
atcgcagacc gataccagga tcttgccatc ctatggaact gcctcggtga gttttctcct   3900
tcattacaga aacggctttt tcaaaaatat ggtattgata atcctgatat gaataaattg   3960
cagtttcatt tgatgctcga tgagttttc taatcagaat tggttaattg gttgtaacac    4020
tggcagagcc tctagtatat aaacgcagaa gggcccaccc gaaggtgagc cagtgtgact   4080
ctagtagaga gcgttcaccg acaaacaaca gataaaacga aaggcccagt ctttcgactg   4140
agcctttcgt tttatttggg ttttgttggt ttttgtgacc tgaatttaat ttgaatcatg   4200
cggaatgcga tcgccttagg acggtcgcat ttttgttta cgtctaaaat tagtcgaaat   4260
ccccatcaa cgccatggta gtgattttgt cttaacgtta ttcacccatc aatttcaaaa   4320
tgaacctgaa gtttcttaaa tctctctggg ctacggcggc gatcgccttt gccattagcg   4380
taaatccgag ccttgtcttt gctgaaacgg aaccccaag cgaaaccaaa actgccctga    4440
tcaatgaact ccgcacctta actttccggg atgaaaacgc gacccagatt ttggacttga   4500
tgctgcaaca gatccaagct caatccacca ccatgggtca tggctttttg ggtgaagaaa   4560
cagatcccga aaccctggcc gctatccaag aaagtgtcac ccgcatcacc gaccgcattt   4620
atacctgat gcaagacaga attgatttcg ttgccctcca gcgggatatc gacttcaagc    4680
tctatcacga atatttcacc gaagccgaac tccaagattt aatcaccttc tataaaacac   4740
ccaccggaca aagactgcc gcaacttttc cagaacttac agaacgctcc acagcccctct   4800
ttagtgagca gctagcccca gccatgatag aaattaccca acaggtgatg ttagaagaat   4860
ttgcctctgc ctttgcaacg ttcgatgctc cagaaactga agcgcctgaa aattcggagt   4920
cggctgaagc agaagccatc gattaaacag agttgcggat ggatctgtgt aatcatcctg   4980
aaacttctac agatcccgca aattaccaac caagataatt gaattcccca tcatctcatc   5040
atggcaacgg acggctttct tcagatattg ctcgccttc tcattgggaa cacacaattt    5100
acttttttg ccaacttga gccttaatcg cgccagtccc catgggtgag aaagccgcac     5160
tagaatgatt ctagagaagt gagattcgag gggaattttt aagatgaaaa aacgagtgac   5220
tctgacattt ccccaggaca cggtgcaaat gcccgtcacc tatcgcttgg caaaggattt   5280
taatattgcg gcgaatatca tccgcgccca ggtcgctcca aaccaggtgg gcaagttgat   5340
ggtggaactc caggggata ttgatgccat tgagatggcc ttggaatgga tgaaaggcaa    5400
ggggattta gtttccctcg cgagcaaaga aattgtgatt aacgaagata tttgtgtgga   5460
ttgtggtctc tgtacagggg tttgtccgac gggagcatta tcgctagatc cccaaaacgtt   5520
tcgactaaaa tttacccgcc aaaaatgtgt ggtttgcgaa cagtgtttac ccgcttgtcc   5580
ggtccaggcg atcgccacaa ttttttaagg taccttccca aaaaaaagtg ctgttggcgg   5640
tgatgaaatc aacccaaaga ttgcaattgt taatgagagt gattataaat tctgttgaaa   5700
aatgtattta aaggtagaaa ccattgtgtt ttaagctttt tgggtctgtt ttgagcaatt   5760
aagaagatta ttctaggcca gagcatccct taggatattg ttaggaattc ctaacttttt   5820
aattcttcat gaaaaaacag gccaacgttc agcgtcacac agagcccgca gatcagaatt   5880
tgcggctaaa aagtcatggc aatttatttt atttattggc tgtggcggcg ggcttgattt   5940
ttttacaggg ttacatgatt gcgccttaa ttccccgttt atcggagatt tttggcgttt     6000
ctgtccagga aattggcttt attgtgccga tttatgtct gtcctacgct gtcatggctc    6060
tttttat                                                              6068

SEQ ID NO: 13          moltype = DNA   length = 20
FEATURE                Location/Qualifiers
misc_feature           1..20
                       note = SYNTHESIZED
source                 1..20
                       mol_type = other DNA
                       organism = synthetic construct
SEQUENCE: 13
aattcgagcg ggattttatg                                                20

SEQ ID NO: 14          moltype = DNA   length = 20
FEATURE                Location/Qualifiers
misc_feature           1..20
                       note = SYNTHESIZED
source                 1..20
                       mol_type = other DNA
                       organism = synthetic construct
SEQUENCE: 14
agagagcgaa cttggtcgaa                                                20

SEQ ID NO: 15          moltype = DNA   length = 3774
FEATURE                Location/Qualifiers
misc_feature           1..3774
                       note = SYNTHESIZED
source                 1..3774
                       mol_type = other DNA
                       organism = synthetic construct
SEQUENCE: 15
gtgaatattt caccccccat tcaacttgtc gaagcccca cccaagcttt actgacctgg      60
gctaaggcga tcgccacggg caccccagac ccatttcagc gggggcaaca actgagtcag    120
```

```
aaattgggcg caacctatgg cagtgatggc ctaacccaaa taggattctg gattccggag  180
gtgggcgatc gccccgttta cctcgaaatt tttacgccca tggaggcaat cgattttcgc  240
cttgctgatc aagtcattcc gttccgtcgg gaggtgctag aactgccgcg ccaggggaa   300
tttgcctggg ccgttgtggc gggtctcaaa gctggcaccc gtacccaagc gggatcgttt  360
tactggttgc gcagtggtga acagattatc cgcgatgtct ttgcccactc tctgccctac  420
ggtgtgtttg cgccagccga gctgtacgac atggcgcaac tggagcgcga cagggccgac  480
cgcgactatt tcaccaggaa aacttgggtc acaccgcccc gcaatatttt gcagattcat  540
gtgggtaccg cttcccccac gggcaccctg gccggactca gccgcattta ccgtgacctc  600
gcccgcaaat tggccaatag ccaacccctc accgccgctg aaaaaaacta tgtgggcttt  660
gatgcgattg aactgttacc cattgaaccc acggtggaat ttcgcccgc cgaaaatgaa   720
atgattcatg cttttggca aattcggcg atcaccaacc aagaagtgca agtccacctg    780
aaaaaaccag acacccaaaa ttggggctat gacgatctga ttttaggggc gcggccacc   840
agtcccgccc tcctcagtac cctcagaccc accgaagttg tggattttat tgccacgctc  900
cacactgcct ttgcccgccc gatccagatt attttttgacc tggtttatgg gcatatccat  960
caccaagccc tgggattaat caatgcgcga ttttttccggg gcgcaaatat gtatggccat 1020
gatacaaacc agcaaaatcc gatggtgcgg gctgttctcc tggagttgca acggcgaaaa 1080
attaatctag gggccgatgg gattcgggtg atgggggtc aagattttca ggtgtccgac  1140
gccatttccg gccaactaga ctatgacaat gatttcctgc tgaagatggc tgcggtaccc 1200
caaaccgttg gtacagcgac tcgcgagttg tacaccattt atgaagatgg ccgcccctgg 1260
cccaatgtcg gttgggaaga tatgctaccc catttggatt taatttacct aaagcccgat 1320
tgttttcagt ggagtccgtt gatcttcgag cataatacgc ccacgttaca gggattttgg 1380
caacgggaat ggcgggatgt gtgcaaaatt atggcccatg ggctcgctg ggtgaccggt  1440
tgcgccaacc atgacacggt acgcaagggc aaccacatca acccgccgc aattcggatt  1500
aatgaatatt tagggattc tttgccggaa attttacaaa atgcctacga taatccagca  1560
acccaactgt ggatccatgg ctttagccca ggaattccga tggattttt aaatgcatta  1620
atgcacactc cctgggcttt ttttcggaat acagatgacc aatatgccgt caaaattatg 1680
gcggacgaaa ttggcttttct ctattggcaa attacgccgg aaatttaccg acaatcctga 1740
gcgtttcggc ggttttaaaac catgggcttt tatgatctct cgttaatgcg gcagttcttt 1800
aaggcagtgg aacaggccat tgaagcgatt ggctatgatc taccaaagct ggcgatttt   1860
ctgcaaaccg aattagaacc acaatttgat ttttaaagc cgattaccat tgccaacctg   1920
aaggaaatag cgatcgcctt tatggaggat ggccacgagg cttgtcgggt ctcccattat  1980
tgtggatcgg taccgatga gcgggcgagc tttaatttac gcttgcggca atatcgccag   2040
gcccagcctt ggctgcgaaa tcatctcgat cctgcaaggg gcgatcgcct gcaccattgg  2100
tcggatcacc aacgcaccat tttctacggc aggcgcaaca ccagcagcgg              2160
cttgtgttag tggcgcacat ggccgggggct ccgaagaccg ttgagattgg caaatggctc  2220
gccctggatt tggatcgttg gcagttggcg atcgccacac cgactttgaa gatcaacacc  2280
atctatgact tagcccaaat tcacttgcac aatggcgaag gttttctgtt atctgaaatt  2340
cctccctaaa tgatgtcttt tgagcctaaa aacacacttt tttgacctaa tttaacccat  2400
aacttcgtat aatgtatgct atacgaagtt atcccccctct tgcctacagc atctcccca   2460
ggggagaatt cttcctgttt caactccctc taacgtaaac ccattgaatt taaaaagac   2520
tttatgactg ctttactgct ccatgaccaa cattattccc ttgatcatga agcctttctc  2580
tcaaccctca gcaacacaga aaatttactc attattcaag atctagatgg cgtttgcatg  2640
gggttagtca aagaccctt aacccgcaaa attgatcctg actatatccg cgccacacgc   2700
aagtttagag accacttctt tgtcctcacc aacggtgaac atgaaggcag aagggggagta 2760
aatcgcatcg ttgaacgggc atttcgcaat gttgaagcca agaggaaac aagctattta   2820
cctggtttag cagcagggg tgtgcaatgg cagacagata atgccaaat tcccatccc    2880
ggtgttagcc aagcagaact cgatttcctt gccacagtgc cagatttaat tggtcaaagt  2940
ttaggacaat tttttactaa atatgttgat atttttcccg ctgagcttca acctgagctg  3000
atccatgctt ctgttttaga taatctcgtt tcaccgacgg caaatttaaa cgtcctggcc   3060
gaatatttag gcgatcgcct tgagatttac caagacctcc agcgcaccat ggaaaccctg   3120
atgaattcgt tgctagaaaa agctggccaa cagggtttag acaatagttt tttcgtgcac   3180
tatgcgccca attttaggcag agataatgtg gggaaagaaa ttgtccgctt tgccacagcc  3240
aaggattctg gcaccacaga tttttcagttt atggtgtgtg gtgccgtcaa agaagcgggg  3300
gttttagtgc tgctgaatta ttactatgcc caacgcacgg gccactatcc cctaggagaa   3360
accttaacg cccgccaagc gccccaaaac cacgaggaac tattgcaact ggtgcaagac   3420
aatttcgatc cgcaattgat gccttttaatc gttggcgtcg gcgatacggt cacaagtcac   3480
accgaaggcg atcaagttcg acggggggggg agcgatcgcc tattcctgca gctcgtccaa   3540
gacattggta aatgggcaaa gagcggcaat tcgtcgtgt atatcgacag ctcccaggga   3600
gaattaaaaa atcggattcc cttaaaactg gggacaatca atggtcaaac ccaagtgatt   3660
gagggcatta ctgatccggc tgatccgtta caaattaacg ttgcttttcc gggcgggttt   3720
gaacaataca ccgcccttt tcagcaggcc gccgcaaacc gatctggaac atag         3774

SEQ ID NO: 16         moltype = DNA  length = 19
FEATURE               Location/Qualifiers
misc_feature          1..19
                      note = SYNTHESIZED
source                1..19
                      mol_type = other DNA
                      organism = synthetic construct
SEQUENCE: 16
catctcgatc ctgcaaggg                                                 19

SEQ ID NO: 17         moltype = DNA  length = 21
FEATURE               Location/Qualifiers
misc_feature          1..21
                      note = SYNTHESIZED
source                1..21
                      mol_type = other DNA
                      organism = synthetic construct
```

SEQUENCE: 17
ttgtttcctc tttggcttca a                                             21

| SEQ ID NO: 18 | moltype = DNA length = 4218 |
|---|---|
| FEATURE | Location/Qualifiers |
| misc_feature | 1..4218 |
| | note = SYNTHESIZED |
| source | 1..4218 |
| | mol_type = other DNA |
| | organism = synthetic construct |

SEQUENCE: 18
```
atgagcgatc gccccataga aaaaccctc gccgaaaagg ctcctgctag ttacgaatgc    60
cccagctgcg gttacattta caccctgca aagggagaaa gccgtaccaa cacgccaccg   120
ggtacagcct ttgaagatct gcccctcatt tggaactgtc ctgttttgtag cgttgatcgc   180
gcccaatttc gcaatattgg tgcagcggat gcccctcag gttttgaaga aaatctgaaa    240
tatggttttg gcgtgaataa cctcagctcc aaccaaaaaa acctactcat ttttggagcc   300
atgggcttgg caatccttt cttcctgagc ctttatggtc tggactaaag accccatag    360
caaagccttg tcttaattcc aaatttttac ttttattgct tttatattgc gctatgactt   420
cagttttagg tctattaaaa cccttaaaaa aagccattgc ggcgatcgcc gttttggtat   480
tgtgcatcgg ctgtgtccag gcaccaacca ttagcgaaaa tccctggcaa gaaatcgact   540
taaataccga ttcgaccttt gccaatattg cttttaccga cgacctccaa catggctggc   600
ttgtcggtac caaagaaacc ctctttgaaa ataccgatgc tgcaaaacc tgggccgagc   660
gagttattga tctcggtgac gaaaagaaa gttttaccgg tgttagcttc tctggccaag   720
aaggctggat taccggacgg ccttcgatcc tgctccacac cgacgatggt ggtgagcact   780
ggagtcgcat cgccctcagc agtcaattgc ccggtgcccc ctacaacatc accgcctag    840
ggcgaacac cgccgaaatg gtcaccgatc ttgggcat ttacaaaacc accgacggcg    900
gcaaaaactg gaaagccctt gtcgaaggtg ccgttggcgt tgcccgcacc attgaacgtt   960
ctgccgatgg taaatatgtg gccgtttctg cccggggtaa tttttattcc acttggtcgc  1020
ctggggacac agaatggacg ccccataacc ggaattcttc ccgtcgcctc caaagcatgg  1080
gctttaatgg cgaagataag ctctggttgt tagcccgtgg ggagttgtg caatttagcg   1140
acgatacaaa tccagacaat gcagaagcct ggagcgaacc agtgacaccg cagtaccgca  1200
acagtgttgg tttgttgcac attggctatc gtaccccgc agaactatgg gccgtcggtg   1260
gtagtggcag tgttgttgtg agtaaagatg gtggcgacac ttggttccgg gacgctgccc  1320
tagaagagat cccgacaaac ttttaccgag tcgtttcct aaatgagaat aaaggcttca  1380
tccttgggca acagggggtg attttacggt acgatacatc cacggaagcg gcctaaggc   1440
aacccattct attgtgggag tgtcttgtaa ttccgtatga tataggctaa tttgtttaat   1500
aagttttttt tcattaacaa ttgagaggag aatagtcgca tggcaggttc taccggagaa   1560
cgcccgtttt ctgacattgt gaccagtatt cgctactggg ttattcacag catcaccatt   1620
ccgatgttat ttattgctgg ctgcctcttt gtgagccatg gcttggctta cgatactttc   1680
gggacacccc gtcctgacca atactttact gaaactcgtc aagagattcc cattgtgact   1740
gatcgttaca aagcgattga tcagatcaat gagtttaaca attaagtaac gcgcgttttt   1800
ctttgctgta ttcactaaaa ggttttgtat tatgacaagc ggtcctaacc aacctgtttc   1860
ttatccaatt tttaccgtcc gttggttggc ggtgcacacc ctggctgtac cctcggtttt   1920
cttcctaggg gcgatcgccg ctatgcagtt tattcaacgt taggagcttc cgatggaaag   1980
aaatcaaaat cccaacagac agcctgtgga actaaaccgg acttctctat atctgggttt   2040
acttctaatc gctgtgctcg gtattctatt ttccagctac ttctttaact aagctggcag   2100
ccctttaatt tcagcccttt aatttatttt tttcggaagt tgttctcatg tctgaaggcg   2160
gaaaaatccc actttggatc gttgcagttg tcgctggtat gggcgtcatt gcggttgtcg   2220
gtatctttt ctacggtgca tatgcagggg taggctctgc ggtttagatg cacaattcgc   2280
tctaattaat tgttgagaca ccacctgctc taattgaggg gtggttttgt tttaggaact   2340
tctgggcaa tagggagtcc aaaaaagttt ggggataatc gtcaacggtg cagtatgact   2400
atgaaaagac agttgcggga tctgaaagta tgggtgatgg tgggtctgtt gagtttaggt   2460
ggagcctggg gtcaaagggc gatcgccgct gaaaccctcc gactaaaatt agggccactt   2520
caacaaactt tacaattaga agatttagaa acctttgccg aaacgggtca agtccccgc    2580
aacctccgac cctatgggt attttggat ggtaatttgc agaaatttct ccaacgacgc    2640
ttgcagatcg agccagagat ggcggatcag tttttgatc agttgtgcg atcgcctacg    2700
ggaaaacaga ttttgcgca aattcaaacg gccctaccgg gaacttctat tcaggatctc   2760
caggcgacgg tggatttggc gttaggtcag ggagtagaaa tcagcgccct gaatttgttg   2820
caggcttacc ccaagcagga actgactatt gatcttacgg cggtggctgg cctcttgtta   2880
caactcaatt taccgaatat ccagaatcaa ctcctcgcgc cgagggtgac tgaagccctc   2940
gaaagtacag aaccgcagat ttttcaacgc tcaaacctca accccacagc ccccggcccc   3000
caaacggtgc ggcgtcaaag cttaattctg caagatgcaa agcgcgatcg caccattccc   3060
attgatattt ttgatagtcc ccaatccag tctcagctag tggttttgtc ccatgggttt   3120
gcggccaacc gtcattttct cgattatctg gcggtgcatc tggcctccca tggttacacc   3180
gtcgttaccc tcgatcaccc cggcagtaat attcagtctc tgtttaatcc gggcttaaat   3240
cttgatactt tgctcccggc gacgaattt gtcgatcggc caaggatat tcaatttgtg    3300
ctggatcaac tggagcgcct caaccaggat caaaccctca aacccgctt tgccacggac   3360
aatgtgacgg taattggcca ttccttcgga ggttacacgg ccttggcgat cgccggagga  3420
attgtcgatc ccattgctat ccgtgctcac tgccagcggg caaccctt aaccagagca    3480
ccggggact ggctcaatg tgcagcggcg aaactcccct atgaccagtt aaatttgcgg    3540
gatgaacggg tcaaacaggc gatcgccctc aatcccctca gcgatcaaat ctttggggag  3600
cagggtttag aaaaaattaa aattccgacc ttgatcgttg ctagtacaaa ggataccgtc  3660
acccaagct tggcccacca gttgaaaccg ttccagcagt tgggcggcga aaatatctc    3720
gtcgtcggca acggtgcaac acatgagc gtcactgatg ttagcaatcg cgatagcgcc   3780
ttggcccaaa gtaccttgt cccggaggtg atgggcaacg cggcagaacc agtccgacaa   3840
atggtacgag gggtaagctt aagctttctg cgcgcgcacc aaaccggagg acaaaattac  3900
cagcaatttc tcacggggc ctatgtgcaa tctctttccc agggggcgat taagctacgc   3960
ctcacgaaa cgatttctcc agagttagaa cgattcctga gtcgcttacc ccaggctccc  4020
aattctgccg aagtggcgac accgactcaa caggctgctt ttttgaatat ggggcgatcg  4080
```

```
ccaaacccaa cccccaaccg cacctatccc cagggcgttc tcacggaaag ccttaagccc   4140
ttgatgacga acttggaatc ggaaactttt ctcgcaataa agccggataa ttttgatgtc   4200
ttgtatcaaa aaccctga                                                 4218

SEQ ID NO: 19          moltype = DNA  length = 24
FEATURE                Location/Qualifiers
misc_feature           1..24
                       note = SYNTHESIZED
source                 1..24
                       mol_type = other DNA
                       organism = synthetic construct
SEQUENCE: 19
tttctgacat tgtgaccagt attc                                            24

SEQ ID NO: 20          moltype = DNA  length = 21
FEATURE                Location/Qualifiers
misc_feature           1..21
                       note = SYNTHESIZED
source                 1..21
                       mol_type = other DNA
                       organism = synthetic construct
SEQUENCE: 20
cggaagctcc taacgttgaa t                                               21

SEQ ID NO: 21          moltype = DNA  length = 3359
FEATURE                Location/Qualifiers
misc_feature           1..3359
                       note = SYNTHESIZED
source                 1..3359
                       mol_type = other DNA
                       organism = synthetic construct
SEQUENCE: 21
gccccataac cggaattctt cccgtcgcct ccaaagcatg ggctttaatg gcgaagataa     60
gctctggttg ttagcccgtg ggggagttgt gcaatttagc gacgatacaa atccagacaa    120
tgcagaagcc tggagcgaac cagtgcacac cgcagtaccgc aacagtgttg gtttgttgca   180
cattggctat cgtaccccccg cagaactatg ggccgtcggt ggtagtgcag tgttgttgt    240
gagtaaagat ggtggcgaca cttggttccg ggacgctgcc ctagaagaga tcccgacaaa    300
cttttaccga gtcgttttct taaatgagaa taaaggcttc atccttgggc aacaggggt    360
gattttacgg tacgatacat ccacggaagc ggcctaaggg caacccattc tattgtggga    420
gtgtctgtta attccgtatg atataggcta atttgtttaa taagttttt tcattaaca     480
attgagagga gaatagtcgc ccccacaaaa ctttcatgat tgcttgagtg aaaattaaat    540
gtttaaagtt cttaaaggag attgttgaga acataaata cttaattcat ctcatttgaa    600
cgcttttccct ctctcaaagat cccgacagaa aacggttta gcccaatgtc tcattaggta   660
gcatggctga attcgagcgg gattttatgt ctttttttagg tatttttgta agggtaaat    720
aggcccatca aacagcatta gaaatgctaa tcagcccaaa aaacaaaagc aatctttttt    780
tgttgctaaa agataaaaat aagtcgaggc tgtggtaaca tatcccacag attaaagaaa    840
gtcataagac ttgaatcttc agaattttaa aaagcagttt tgccaacgta agattttga    900
agttttcgac caacaatacc gttactggta ttttgtctgtt aaagataagc attttttgctt   960
gaggaaaacc gcatggttca gaccaaatct gctgggttta atgccggttc caacctgctg   1020
acggtgcacc agaatctgcc ggcactgccg gtcgatgcaa ccagtgacga agtgcgcaaa    1080
aatctgatgg atatgtttcg tgaccgccaa gccttcgca aacatacgtg gaaaatgctg    1140
ctgtcggtt gccgtagctg gcggcctgg tgtaaactga caatcgcaa atggtttccg      1200
gcagaaccgg aagatgtgcg tgactatctg ctgtacctgc aggcacgtgg tctggcagtt    1260
aaaaccatcc agcaacatct gggccaactg aacatgctgc accgtcgctc tggtctgccg    1320
cgtccgagtg attccaatgc cgtcagtctg gtgatgcgct gcattcgtaa agaaaacgtg    1380
gatgcaggcg aacgcgctaa acaggcactg gcttttgaac gtaccgattt cgaccaagtt    1440
cgctctctga tggaaaacag tgatcgttgc caggacatcc gcaatctggc attcctgggt    1500
attgcttata cacccctgct gcgcattgca gaaatcgctc gtattcgcgt gaaagatatc    1560
agccgtacgg acggcggtcg catgctgatt cacatccggcc gtaccaaaac gctgtttcc    1620
accgcgggcg tcgaaaaagc cctgtcactg ggtgtcacga aactggtgga acgctggatt    1680
tcagtttcgg gcgtcgcaga tgacccgaac aattaccgt tttgtcgtgt gcgcaaaaat    1740
ggtgttgcag ctccgagcgc tacctctcag ctgagtacgc gtgcgctgga aggcatcttc    1800
gaagccaccc atcgcctgat ttatggcgcg aaagatgaca gcggtcagcg ttacctggca    1860
tggtccggtc actcagctcg tgttggtgca gcacgtgtgc tggcagtgc aggtgtctct    1920
atcccggaaaa ttatgcaggc cggcggttgg acgaacgtga atattgttat gaactatatt    1980
cgtaacctgg actctgaaac gggtcgatgt gtgcgtctgc tggaagatgg cgactgacga    2040
gggcggtgct ttggcaggat ccggctgcta caaagcccg aaaggaagct gagttggctg    2100
ctgccaccgc tgagcaataa ctagcataac ccctggggc tctaaacgg tcttgacgg     2160
gttttttgtc tagatcaacg gcctcaacct actactggga ttgacaatta atcatcgta    2220
tagtatatcg gcatagtata atacgacaag gtgaggaact aaaccatgaa gctgaccagc    2280
gccgttccgg tgctcaccgc gcgcgacgtc gccggagcgg tcgagttctg gaccgaccgg    2340
ctcgggttct cccgggactt cgtggaggac gacttcgccg gtgtggtccg ggacgacgtg    2400
accctgttca tcagcgcgt ccaggaccag gtggtgccgg acaacccct ggcctgggtg     2460
tgggtgcgcg gcctgacga gctgtacgcc gagtggtcgg aggtctgtct cacgaacttc    2520
cgggacgccc ccgggccggc catgaccgag atcggcgagc agcgtgggg cgggagttc     2580
gccctgcgcg accggccgg caactgcgtg cacttcgtgg ccgaggagca ggactaaccg    2640
acgtcgaccc actctagagg atccccgctc cgtgtaaatg gaggcgctcg ttgatctgag    2700
ccttgccccc tgacgaacgg cggtggatgg aagatactgc tctcaagtgc tgaagcgta    2760
gcttagctcc ccgtttcgtg ctgatcagtc ttttttcaaca cgtaaaaagc ggaggagttt    2820
```

```
tgcaattttg ttggttgtaa cgatcctccg ttgcaattga tgcacaattc gctctaatta    2880
attgttgaga caccacctgc tctaattgag gggtggtttt gttttaggaa cttctggggc    2940
aatagggagt ccaaaaaagt ttggggataa tcgtcaacgg tgcagtatga ctatgaaaag    3000
acagttgcgg gatctgaaag tatgggtgat ggtgggtctg ttgagtttag gtggagcctg    3060
gggtcaaagg gcgatcgccg ctgaaaccct ccgactaaaa ttagggccac ttcaacaaac    3120
tttacaatta gaagatttag aaacctttgc cgaaacgggt caagtccccc gcaacctccg    3180
accctatggg gtattttttgg atggtaattt gcagaaattt ctccaacgac gcttgcagat    3240
cgagccagag atggcggatc agtttttttga tcagttgtgg cgatcgccta cgggaaaaca    3300
gattttggcg caaattcaaa cggccctacc gggaacttct attcaggatc tccaggcga     3359

SEQ ID NO: 22          moltype = DNA  length = 20
FEATURE                Location/Qualifiers
misc_feature           1..20
                       note = SYNTHESIZED
source                 1..20
                       mol_type = other DNA
                       organism = synthetic construct
SEQUENCE: 22
aattcgagcg ggattttatg                                                 20

SEQ ID NO: 23          moltype = DNA  length = 20
FEATURE                Location/Qualifiers
misc_feature           1..20
                       note = SYNTHESIZED
source                 1..20
                       mol_type = other DNA
                       organism = synthetic construct
SEQUENCE: 23
agagagcgaa cttggtcgaa                                                 20
```

SYSTEMS AND METHODS FOR GENETIC ENGINEERING OF A POLYPLOID ORGANISM

CROSS-REFERENCE TO RELATED APPLICATIONS

This application is a divisional application of U.S. Non-Provisional patent application Ser. No. 16/894,416; filed Jun. 5, 2020 which claims priority to U.S. Provisional Ser. No. 62/857,582, filed Jun. 5, 2019, the contents of which are hereby incorporated by reference in their entirety.

SEQUENCE LISTING

The present application contains a Sequence Listing which has been submitted electronically in .XML format and is hereby incorporated herein by reference in its entirety. Said computer readable file, was created on Dec. 19, 2023 is named 055743_779440_Sequence_Listing.xml and is 26 kilobytes in size.

FIELD OF THE INVENTION

The present disclosure provides compositions and methods for genetically modifying a nucleic acid sequence in a polyploid organism.

BACKGROUND OF THE INVENTION

In most modern biotechnological applications, use of DNA modifying techniques (e.g., integrases, recombinases and CRISPR/Cas9) is routine practice, as these serve as tools for genome engineering to create recombinant organisms with various features or traits of interest. Presently, the genes encoding various components for DNA modification are delivered into host organisms on plasmids which must then later be removed by various counter-selection methods after the desired DNA modification has taken place. Overall, this process involves multiple steps and genetic parts that are not always available, compatible, or convenient for use with specific host organisms of interest. Meanwhile, many organisms of interest to biotechnological applications are polyploid in nature, including plants, algae, and cyanobacteria, all of which show promise for carbon-neutral applications in a bio-based economy.

Technological advances in these organisms in particular have been hindered by the lack of shuttle vectors and associated counter-selection systems and methods and tools for identifying and isolating successful products of genetic engineering. Adaptation of existing systems for use in cyanobacteria, for instance, is limited by a lack of easy-to-use replicative plasmids and counter-selection systems that are typically employed in other heterotrophic microorganisms. For example, one common counter-selection marker, sacB, which polymerizes sucrose into the toxic derivative levansucrose, cannot be used in the model cyanobacteria, *Synechococcus* sp. PCC 7002, because it already naturally produces sucrose as an osmolyte. Furthermore, common broad-host range plasmids such as those with the RSF1010 origin of replication are difficult to transform into many host organisms and are very large (i.e., >10 kb), making them a challenge to work with.

There is a need for genetic tools and methods for efficient genetic engineering of cyanobacteria and other polyploid organisms for which tools for genetic engineering are not readily available.

SUMMARY OF THE INVENTION

One aspect of the present disclosure encompasses a system for genetically modifying at least one nucleic acid sequence of interest in a polyploid organism. The system comprises a first nucleic acid construct. A schematic representation of an aspect of the system depicting the first nucleic acid construct for integration into an essential gene is shown in FIG. 1.

The nucleic acid construct encodes a nucleic acid modification system for modifying the at least one nucleic acid sequence of interest in the organism. The first construct further encodes a first reporter and comprises regions of homology to a first locus in an essential nucleic acid sequence in the organism flanking the nucleic acid modification system and the first reporter for integration of the first nucleic acid construct into the locus. The first reporter can be a kanamycin resistance gene or a zeocin resistance gene. When the polyploid organism is *Synechococcus* species, the essential nucleic acid sequence can be the rbcLXS operon or the psbEFLJ operon.

In some aspects, the nucleic acid modification system is a modular modification system comprising more than one component. When the nucleic acid modification system is modular, the first construct further encodes (i) a site-specific recombination system having specificity for recombination recognition sequences, and (ii) at least one component of the modification system required for the function of the modular modification system, and wherein the system further comprises a second nucleic acid construct encoding a nucleic acid sequence comprising one or more components of the modification system.

Another aspect of the present disclosure encompasses a system for genetically modifying at least one nucleic acid sequence of interest in a polyploid organism. The system comprises a first and a second nucleic acid construct. The first and second nucleic acids of the system can be as described in FIG. 2.

The first nucleic acid construct encodes a site-specific recombination system having specificity for recombination recognition sequences and a first reporter. The site-specific recombination system can be Cre-LoxP. The first construct also encodes regions of homology to a first locus in an essential nucleic acid sequence in the organism flanking the site-specific recombination system and the first reporter for integration of the nucleic acid construct into the first locus.

The second construct comprises a nucleic acid sequence for introducing at least one genetic modification in the nucleic acid sequence of interest. The second construct further comprises a second reporter and recombination recognition sequences flanking the second reporter or the second reporter and the nucleic acid sequence for introducing at least one genetic modification in the nucleic acid sequence of interest.

The second construct further comprises regions of homology to a second locus flanking the nucleic acid sequence comprising the at least one genetic modification and the second reporter for integration of the second construct into the second locus. The first construct, the second construct, or both can be plasmid-free.

The polyploid organism can be selected from plants, algae, and cyanobacteria. In some aspects, the polyploid organism is *Synechococcus* species. When the polyploid organism is *Synechococcus* species, the second locus can be in a neutral integration site (NIS). In some aspects, the NIS is the glpK gene. In some aspects, the second reporter is a gentamycin resistance gene.

When the nucleic acid modification system comprises a first and a second nucleic acid modification system as described above, an aspect of the present disclosure encompasses a method of genetically modifying at least one nucleic acid sequence of interest in a polyploid cell. The method can achieve full segregation of the genetic modification of the nucleic acid sequence of interest. The method comprises the steps of:
  a. obtaining or having obtained a system for genetically modifying the nucleic acid sequence of interest in a polyploid organism, the system comprising at least two nucleic acid sequence constructs as described above;
  b. introducing the second nucleic acid construct into the cell;
  c. identifying a homologous recombination event of the second construct at the second locus by identifying a cell expressing the second reporter;
  d. introducing the first nucleic acid construct into the cell;
  e. identifying a homologous recombination event of the first construct at the first locus in the essential nucleic acid sequence by identifying a cell from step (d) expressing the first reporter;
  f. maintaining the cell under conditions for continuing expression of the first reporter and removing conditions for maintaining expression of the second reporter for a sufficient length of time for the site-specific recombination system to excise the second reporter;
  g. identifying a cell that expresses the first reporter and fails to express the second reporter;
  h. removing conditions for maintaining expression of the first reporter in a cell from step (g); and
  i. identifying a cell from step (h) that fails to express the first reporter, thereby generating a genetically modified cell comprising the at least one nucleic acid modification.

The method can achieve full segregation of the genetic modification of the nucleic acid sequence of interest. The method can further comprise confirming that the at least one nucleic acid sequence of interest is modified after step (d) and before step (e). The method can also comprise confirming excision of the second reporter or the second reporter and the recombinase recognition sequences from the second locus after step (g). In some aspects, the method further comprises confirming the absence of the first construct from the locus in the essential nucleic acid sequence after step (h).

The polyploid organism can be *Synechococcus* species. When the polyploid organism is *Synechococcus* species, the second reporter is a selectable reporter, and identifying a homologous recombination event of the second construct with the nucleic acid sequence of interest comprises selecting for expression of the selectable reporter. When the polyploid organism is *Synechococcus* species, the second reporter is gentamycin resistance, and identifying a homologous recombination event of the second construct with the nucleic acid sequence of interest comprises identifying cells capable of growing in the presence of gentamycin. Alternatively, the first reporter can be a selectable reporter, and identifying a homologous recombination event of the first construct into the essential nucleic acid sequence comprises selecting for expression of the selectable reporter. Further, the first reporter can be kanamycin resistance, and identifying a homologous recombination event of the first construct into the essential nucleic acid sequence comprises identifying cells capable of growing in the presence of kanamycin.

A flow chart depicting an aspect of a method of the disclosure is depicted in FIG. 14. The method can achieve full segregation of the genetic modification of the nucleic acid sequence of interest. The method can further comprise the step of confirming that the at least one nucleic acid sequence of interest is modified after step (d) and before step (e). The method can also comprise the step of confirming excision of the second reporter or the second reporter and the recombinase recognition sequences from the second locus after step (g). Additionally, the method can comprise the step of confirming the absence of the first construct from the locus in the essential nucleic acid sequence after step (h).

In some aspects, the second reporter is a selectable reporter, and identifying a homologous recombination event of the second construct with the nucleic acid sequence of interest comprises selecting for expression of the selectable reporter. In an alternative of the aspects, the second reporter is gentamycin resistance, and identifying a homologous recombination event of the second construct with the nucleic acid sequence of interest comprises identifying cells capable of growing in the presence of gentamycin.

In some aspects, the first reporter is a selectable reporter, and identifying a homologous recombination event of the first construct into the essential nucleic acid sequence comprises selecting for expression of the selectable reporter. In an alternative of the aspects, the first reporter is kanamycin resistance, and identifying a homologous recombination event of the first construct into the essential nucleic acid sequence comprises identifying cells capable of growing in the presence of kanamycin.

An additional aspect of the present disclosure encompasses recombinant polyploid cell comprising a system as described above.

Yet another aspect of the present disclosure encompasses a kit comprising the system described above. The system can be used in the methods described above.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
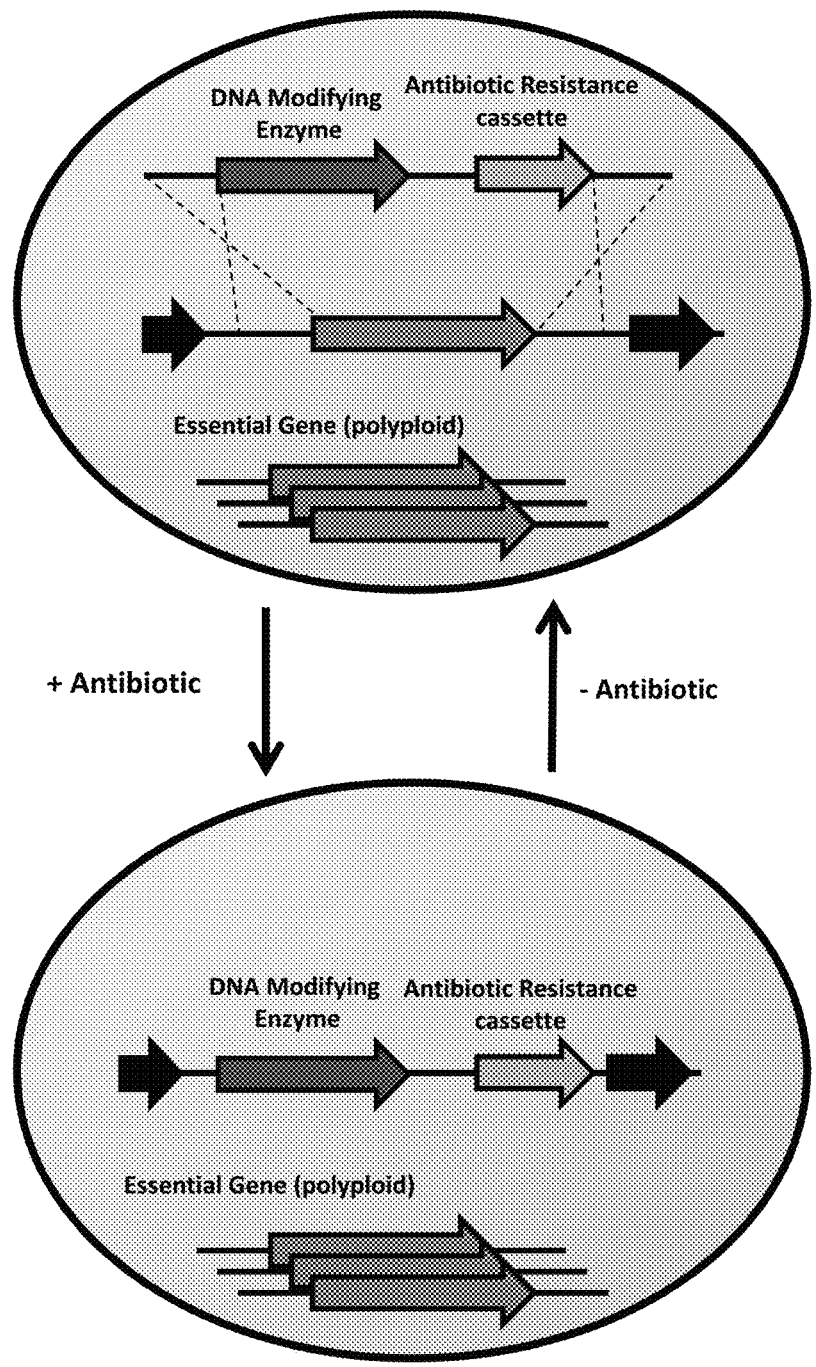
FIG. 1. A schematic representation of an aspect of a system for genetically modifying at least one nucleic acid sequence of interest in a polyploid organism. Copies of an essential nucleic acid sequence are shown in blue. A construct encoding a DNA modifying enzyme and homologous recombination of the construct is also shown (panel 1; top). In panel 2 (bottom), the construct is shown integrated into a copy of the essential nucleic acid sequence and replacing the copy of the essential nucleic acid sequence.

The present disclosure encompasses compositions and methods of using the tools to genetically modify a polyploid organism. The methods exploit polyploidy of the organism as an inherent counter-selection strategy in order to transiently introduce and express a nucleic acid modification system in order to modify a nucleic acid sequence of interest in a markerless manner. The method can achieve full segregation of the genetic modification.

Further, the compositions and methods eliminate the need for genetic tools specifically adapted for each polyploid organism that may not be readily available, thus saving time and effort in generating genetically engineering such organisms. Importantly, the systems and methods are capable of achieving markerless modifications to nucleic acid sequences of interest, as well as full segregation of a genetic modification of a nucleic acid sequence of interest. As used herein, the term "full segregation" refers to the modification of all copies of a target nucleic acid site in a polyploid cell. As used herein, the term "markerless" refers to a genetically modified polyploid organism that does not continue to carry or express an antibiotic selection marker or other reporter after the organism has been genetically modified.

I. Compositions

One aspect of the present disclosure encompasses a system for genetically engineering a polyploid organism. The system can comprise at least one or at least two nucleic acid constructs. A system comprising at least one nucleic acid construct can be as described in Section I(b), and a system comprising at least two nucleic acid constructs can be as described in Section I(c). The one or more of the constructs can be plasmid-free.

(a) Polyploid Organism.

Polyploid or polyploidy is the heritable condition of possessing more than two complete sets of chromosomes. Polyploidy is common among plants, algae, certain bacteria such as photosynthesizing bacteria, as well as among certain groups of fish and amphibians. For instance, some salamanders, frogs, and leeches are polyploids. In some aspects, the polyploid organism is a polyploid photosynthesizing bacterium of the class Cyanobacteria. Any cyanobacterium can be appropriate for a composition of the disclosure provided the cyanobacterium is a polyploid cyanobacterium. The cyanobacterium can belong to the order *Chroococcales*, *Chroococcidiopsidales*, *Gloeobacterales*, *Nostocales*, *Oscillatoriales*, *Pleurocapsales*, *Spirulinales*, *Synechococcales*, *Incertae sedis*, and endosymbiotic plastids, among others. In some aspects, the cyanobacterium is a species of *Synechococcus*. Non-limiting examples of *Synechococcus* species can be *Synechococcus ambiguus* Skuja, *Synechococcus arcuatus* var. *calcicolus* Fjerdingstad, *Synechococcus bigranulatus* Skuja, *Synechococcus brunneolus* Rabenhorst, *Synechococcus caldarius* Okada, *Synechococcus capitatus* A. E. Bailey-Watts & J. Komerek, *Synechococcus carcerarius* Norris, *Synechococcus elongatus* (Nageli) Nageli, *Synechococcus endogloeicus* F. Hindek, *Synechococcus epigloeicus* F. Hindek, *Synechococcus ferrunginosus* Wawrik, *Synechococcus intermedius* Gardner, *Synechococcus koidzumii* Yoneda, *Synechococcus lividus* Copeland, *Synechococcus marinus* Jao, *Synechococcus minutissimus* Negoro, *Synechococcus mundulus* Skuja, *Synechococcus nidulans* (Pringsheim) Komarek, *Synechococcus rayssae* Dor, *Synechococcus rhodobaktron* Komerek & Anagnostidis, *Synechococcus roseopersicinus* Grunow, *Synechococcus roseo-purpureus* G. S. West, *Synechococcus salinarum* Komarek, *Synechococcus salinus* Fremy, *Synechococcus sciophilus* Skuja, *Synechococcus sigmoideus* (Moore & Carter) Komerek, *Synechococcus spongiarum* Usher et al., *Synechococcus subsalsus* Skuja, *Synechococcus sulphuricus* Dor, *Synechococcus van-tieghemii* (Pringsheim) Bourrelly, *Synechococcus violaceus* Grunow, *Synechococcus viridissimus* Copeland. *Synechococcus vulcanus* Copeland.

In some aspects, a cyanobacterium can be any *Synechocystis* or *Synechococcus* species. In some aspects, the cyanobacterium can be *Synechocystis* sp. PCC 6803 or *Synechococcus* sp. PCC 7002 or a strain derived from *Synechocystis* sp. PCC 6803 or *Synechococcus* sp. PCC 7002. In some aspects, the cyanobacterium is *Synechococcus* sp. PCC 7002. *Synechococcus* sp. PCC 7002 can utilize high light irradiation, hence enabling it to grow with a short doubling time of under 3 h. Furthermore, *Synechococcus* sp. PCC 7002 can grow photoautotrophically, mixotrophically, or heterotrophically and tolerates a wide range of temperatures and salt concentrations. A schematic representation of an aspect of the system for genetically modifying a nucleic acid sequence of interest in *Synechococcus* sp. PCC 7002 is shown in FIG. 1.

(b) System Comprising One Nucleic Acid Construct.

One aspect of the present disclosure encompasses a system comprising at least one nucleic acid construct for genetically modifying at least one nucleic acid sequence of interest in a polyploid organism. A schematic representation of an aspect of the system comprising one nucleic acid construct is shown in FIG. 1.

The system comprises a first nucleic acid construct. The first construct encodes a first nucleic acid modification system for modifying the at least one nucleic acid sequence of interest in the organism. As such, the first construct comprises the tools for genetically modifying at least one nucleic acid sequence of interest in the organism. Nucleic acid modification systems can be as described in Sections I(d).

The first nucleic acid construct encodes a first reporter for identifying successful homologous recombination events. The first reporter can be as described in Section I(g). The first construct further comprises regions of homology to a first locus in an essential nucleic acid sequence in the organism flanking the nucleic acid modification system and the first reporter for integration of the first nucleic acid construct into the locus by homologous recombination. The regions of homology can be as described in Section I(f).

Essential nucleic acid sequences in an organism are sequences critical for the survival of the organism. The essential nucleic acid sequence can be an essential gene or an essential non-coding nucleic acid sequence. For instance, an essential non-coding nucleic acid sequence can be a regulatory sequence essential for survival of the organism. It should be recognized that being an essential nucleic acid sequence is highly dependent on the conditions in which an organism lives. For instance, when the nucleic acid sequence is a gene required to digest starch is only essential if starch is the only source of energy. As such, the term "essential nucleic acid sequence" as used herein refers to any nucleic acid sequence essential for survival of the organism under any growth conditions or a conditionally essential nucleic acid sequence. An individual of skill in the art will recognize methods of identifying essential nucleic acid sequences suitable for integration of the first construct. When the polyploid organism is *Synechococcus*, an essential gene can be the rbcLXS operon or the psbEFLJ operon.

In some aspects, the nucleic acid modification system is a modular nucleic acid modification system. As used herein, a modular nucleic acid modification system can be any modification system which comprises more than one component that, when separately expressed from, e.g., using more than one construct, can provide all the necessary functions to form a complete modification system for modifying a nucleic acid sequence. When the nucleic acid modification system is a modular nucleic acid modification system, in one aspect, the first nucleic acid construct encodes at least one component of the modification system, and the system can further comprise at least a second nucleic acid construct encoding a nucleic acid sequence comprising one or more components of the modification system. In these aspects, the first construct can encode one or more component of the modular modification system required for the function of the modular modification system in addition to the site-specific recombination system, and the at least second nucleic acid construct encodes one or more component of the modification system. Expression of the components of the modification system from the first nucleic acid construct and the at least second nucleic acid construct provide all the necessary components of the modification system for modifying a nucleic acid sequence. In another aspect, at least one, or all, component s, required for function of the modification system are included in the first construct. A non-limiting example of a modular nucleic acid modification system is a CRISPR nuclease system wherein a CRISPR nuclease and a guide RNA essential for the function of the modification system can be components expressed from separate nucleic acid constructs. In some aspects, the modular nucleic acid modification system is a CRISPR/cas9 nucleic acid modification system, wherein the first construct encodes the cas9 nuclease, and the sgRNA of the CRISPR/cas9 is provided in trans, e.g., by expression from a second nucleic acid construct.

(c) System Comprising Two Nucleic Acid Constructs.

One aspect of the present disclosure encompasses a system for genetically modifying at least one nucleic acid sequence of interest in a polyploid organism comprising at least two nucleic acid constructs for genetically modifying at least one nucleic acid sequence of interest in a polyploid organism. The system comprises a first and at least a second nucleic acid construct. The first construct, the at least a second nucleic acid construct, or both can be plasmid-free.

The first nucleic acid construct encodes a nucleic acid modification system. A nucleic acid modification system can be as described in Section I(d). In some aspects, the nucleic acid modification system is a site-specific recombination system having specificity for recombination recognition sequences. In these aspects, the at least second nucleic acid construct comprises recombination recognition sequences recognized by the site-specific recombination system for excising any nucleic acid sequences between the recombination recognition sequences. The first and second constructs of a system of this embodiment are described in Sections I(c)(A) and I(c)(B).

A. First Nucleic Acid Construct

Figure 2:
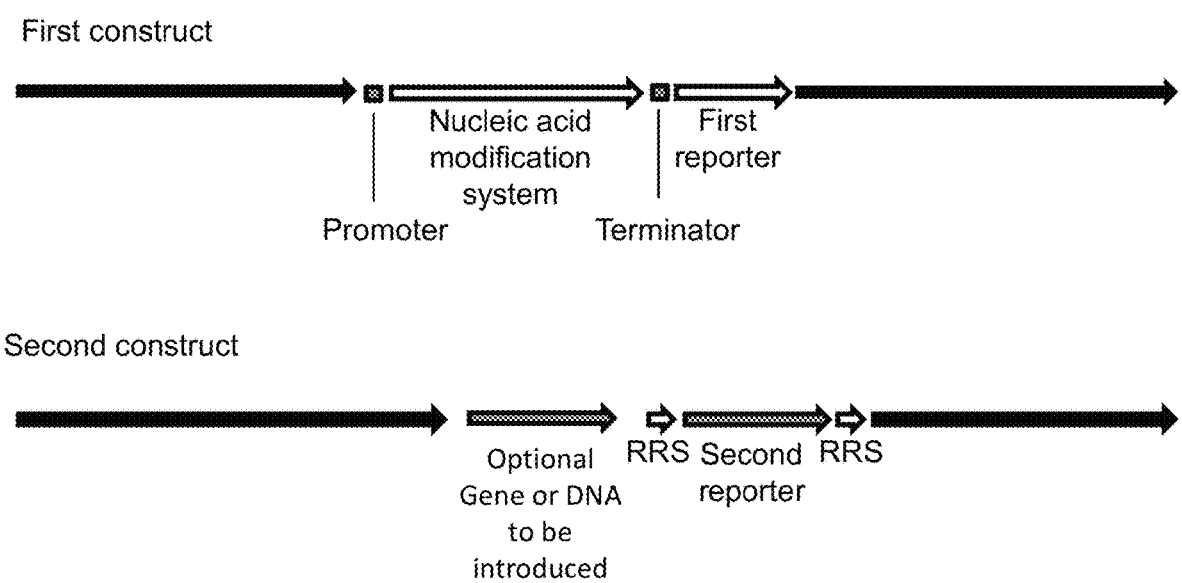
FIG. 2. Schematic representation of an aspect of the first and second constructs. The first construct (top) comprises a nucleic acid modification system flanked by a promoter and a terminator along with a first reporter (e.g., an antibiotic resistance cassette reporter). This construct integrates into an essential nucleic acid sequence in a polyploid organism. The second construct (bottom) represents a nucleic acid sequence of interest to be modified by the nucleic acid modification system encoded by the first construct. RRS is recombination recognition sequence. Black arrows are genomic sequences at, and adjacent to a first locus (top) and a second locus (bottom). The second construct may optionally include a nucleic acid sequence to be introduced into the host that is then not targeted for removal by the nucleic acid modification system FIG. 3A. Schematic of the wild type PCC 7002 glpK locus. Schematic depicting the genomic locus of the glpK neutral site in wild type *Synechococcus* sp. PCC 7002. Empty arrowheads depict the glpK-specific primers (glpK+ primers).

The system comprises a first nucleic acid construct. A schematic representation of an aspect of the first nucleic acid construct is shown in FIG. 2. The first construct encodes a site-specific recombination system having specificity for recombination recognition sequences. Site-specific recombination systems can be as described in Section I(e). Expression of the site-specific recombination system in a cell comprising an integrated second nucleic acid construct induces the excision of a second reporter. The second nucleic acid construct and the function of site-specific recombination systems in a system of the instant disclosure is further described in Section I(c)(B) below.

The first nucleic acid construct also encodes a first reporter for identifying a successful homologous recombination event, and integration of the first nucleic acid construct into the first locus in the essential gene. Reporters can be as described in Section I(g). The site-specific recombination system and the first reporter are flanked by regions of homology to a first locus in an essential nucleic acid sequence in the organism for integration of the first construct into the first locus by homologous recombination. The regions of homology can be as described in Section I(f), and the second reporter can be as described in Section I(g). Essential genes can be as described in Section I(b)(A). The polyploid organism can be plants, algae, or cyanobacteria. In some aspects, the polyploid organism is *Synechococcus* species. When the polyploid organism is *Synechococcus*, an essential gene can be the rbcLXS operon or the psbEFLJ operon.

B. Second Construct

The system further comprises at least a second nucleic acid construct. A schematic representation of an aspect of a second nucleic acid construct is shown in FIG. 2. The second construct comprises a nucleic acid sequence for introducing at least one genetic modification in the nucleic acid sequence of interest. The nucleic acid sequence for introducing at least one genetic modification in the nucleic acid sequence of interest can be a nucleic acid modification system. A nucleic acid modification system can be as described in Section I(d). The nucleic acid sequence for introducing at least one genetic modification can also be a sequence for inserting at least one nucleotide, a deletion of at least one nucleotide, and/or a substitution of at least one nucleotide into the second locus. In some aspects, the at least one genetic modification can be the introduction of a native or heterologous nucleic acid sequence of interest.

The second nucleic acid construct also encodes a second reporter for identifying successful homologous recombination events. The second reporter can be as described in Section I(g). The second construct further comprises recombination recognition sequences flanking the second reporter or the second reporter and the nucleic acid sequence for introducing at least one genetic modification. The recombination recognition sequences are recognized by the site-specific recombination system described in Section I(c)(A) having specificity for the recombinant recognition sequences for excising the second reporter or the second reporter and the nucleic acid sequence for introducing at least one genetic modification. As such, expression of the site-specific recombination system in a cell comprising an integrated second nucleic acid construct induces the excision of the second reporter or the second reporter and the nucleic acid sequence for introducing at least one genetic modification.

In some aspects, the recombination recognition sequences flank the second reporter. FIG. 2 depicts a schematic representation of such an aspect, where the recombination recognition sequences flank the second reporter. Using this system in a method of the disclosure generates a genetically modified organism comprising a nucleic acid sequence introduced into the second locus. In other aspects, the recombination recognition sequences flank the second reporter and the nucleic acid sequence for introducing at least one genetic modification.

Site-specific recombination systems and recombination sites can be as described in Section I(e). In some aspects, the site-specific recombination system is a recombinase system. In one aspect, the recombinase system is Cre-LoxP, wherein the site-specific nuclease is Cre and the first nucleic acid construct expresses Cre, and the LoxP recombination recognition sequences flank the second reporter or the second reporter and the nucleic acid sequence for introducing at least one genetic modification.

The nucleic acid sequence for introducing at least one genetic modification, the second reporter, and the recombination recognition sequences are flanked by regions of homology to a second locus for integration of the second construct into the second locus by homologous recombination. Nucleic acid modification systems can be as described in Sections I(d), regions of homology can be as described in Sections I(f), reporters can be as described in Sections I(g), and site-specific recombination systems can be as described in Sections I(e).

The second locus can be any locus in the genome of an organism, provided the insertion of the first construct does not negatively impact the survival of the organism. For instance, if the first locus is in a gene, the gene is not essential for survival of the organism. In some aspects when the organism is a *Synechococcus* species, the first locus is in a neutral integration site (NIS). NISs for standardized integration of non-native genes are an important tool for efficient genomic engineering in organisms. Several NISs in *Synechococcus* are known in the art, and continue to be annotated. As such, any NIS currently annotated or yet to be annotated can be suitable for integration of the first construct of the present disclosure. In some aspects, when the polyploid organism is *Synechococcus*, the NIS is the glpK gene of *Synechococcus*, aquI, or NS1.

(d) Nucleic Acid Modification System.

A nucleic acid modification system can be any single or group of components capable of effecting a genetic change in the organism. For instance, the nucleic acid modification system can be a post-transcriptional regulation system. The nucleic acid modification system can also be a programmable nucleic acid modification system. Programmable nucleic acid modification systems generally comprise a programmable, sequence-specific nucleic acid-binding domain, and a modification domain. The programmable nucleic acid-binding domain may be designed or engineered to recognize and bind different nucleic acid sequences. In some modification systems, the nucleic acid-binding domain is mediated by interaction between a protein and the target nucleic acid sequence. Thus, the nucleic acid-binding domain may be programmed to bind a nucleic acid sequence of interest by protein engineering. In other modification systems, the nucleic acid-binding domain is mediated by a guide nucleic acid that interacts with a protein of the modification system and the target nucleic acid sequence. In such instances, the programmable nucleic acid-binding domain may be targeted to a nucleic acid sequence of interest by designing the appropriate guide nucleic acid. Any of the multi-component systems described herein are to be considered modular, in that the different components may optionally be distributed among two or more nucleic acid constructs as described herein.

i. Post-Transcriptional Regulation System.

In some aspects, the nucleic acid modification system is an interfering nucleic acid (RNAi) molecule. RNAi molecules generally act by forming a heteroduplex between a nucleic acid sequence in the RNAi molecule and a target RNA molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid encoding the target. Non-limiting examples of interfering nucleic acid molecules are an antisense molecule, siRNA molecules, single-stranded siRNA molecules, miRNA molecules, and shRNA molecules.

ii. CRISPR Nuclease Systems.

The programmable nucleic acid modification system may be an RNA-guided CRISPR nuclease system. The CRISPR system is guided by a guide RNA to a target sequence at which a protein of the system introduces a double-stranded break in a target nucleic acid sequence.

The CRISPR nuclease system may be derived from any type of CRISPR system, including a type I (i.e., IA, IB, IC, ID, IE, or IF), type II (i.e., IIA, IIB, or IIC), type II (i.e., IIIA or IIIB), or type V CRISPR system. The CRISPR/Cas system may be from *Streptococcus* sp. (e.g., *Streptococcus pyogenes*), *Campylobacter* sp. (e.g., *Campylobacter jejuni*), *Francisella* sp. (e.g., *Francisella novicida*), *Acaryochloris* sp., *Acetohalobium* sp., *Acidaminococcus* sp., *Acidithiobacillus* sp., *Alicyclobacillus* sp., *Allochromatium* sp., *Ammonifex* sp., *Anabaena* sp., *Arthrospira* sp., *Bacillus* sp., *Burkholderiales* sp., *Caldicelulosiruptor* sp., *Candidatus* sp., *Clostridium* sp., *Crocosphaera* sp., *Cyanothece* sp., *Exiguobacterium* sp., *Finegoldia* sp., *Ktedonobacter* sp., *Lactobacillus* sp., *Lyngbya* sp., *Marinobacter* sp., *Methanohalobium* sp., *Microscilla* sp., *Microcoleus* sp., *Microcystis* sp., *Natranaerobius* sp., *Neisseria* sp., *Nitrosococcus* sp., *Nocardiopsis* sp., *Nodularia* sp., *Nostoc* sp., *Oscillatoria* sp., *Polaromonas* sp., *Pelotomaculum* sp., *Pseudoalteromonas* sp., *Petrotoga* sp., *Prevotella* sp., *Staphylococcus* sp., *Streptomyces* sp., *Streptosporangium* sp., *Synechococcus* sp., or *Thermosipho* sp.

Non-limiting examples of suitable CRISPR systems include CRISPR/Cas systems, CRISPR/Cpf systems, CRISPR/Cmr systems, CRISPR/Csa systems, CRISPR/Csb systems, CRISPR/Csc systems, CRISPR/Cse systems, CRISPR/Csf systems, CRISPR/Csm systems, CRISPR/Csn systems, CRISPR/Csx systems, CRISPR/Csy systems, CRISPR/Csz systems, and derivatives or variants thereof. Preferably, the CRISPR system may be a type II Cas9 protein, a type V Cpf1 protein, or a derivative thereof. More preferably, the CRISPR/Cas nuclease may be *Streptococcus pyogenes* Cas9 (SpCas9), *Streptococcus thermophilus* Cas9 (StCas9), *Campylobacter jejuni* Cas9 (CjCas9), *Francisella novicida* Cas9 (FnCas9), or *Francisella novicida* Cpf1 (FnCpf1).

In general, a protein of the CRISPR system comprises a RNA recognition and/or RNA binding domain, which interacts with the guide RNA. A protein of the CRISPR system also comprises at least one nuclease domain having endonuclease activity. For example, a Cas9 protein may comprise a RuvC-like nuclease domain and a HNH-like nuclease domain, and a Cpf1 protein may comprise a RuvC-like domain. A protein of the CRISPR system may also comprise DNA binding domains, helicase domains, RNase domains, protein-protein interaction domains, dimerization domains, as well as other domains.

A protein of the CRISPR system may be associated with one or more guide RNAs (gRNA). The guide RNA may be a single guide RNA (i.e., sgRNA), or may comprise two RNA molecules (i.e., crRNA and tracrRNA). The guide RNA interacts with a protein of the CRISPR system to guide it to a target site in the DNA. The target site has no sequence limitation except that the sequence is bordered by a protospacer adjacent motif (PAM). For example, PAM sequences for Cas9 include 3'-NGG, 3'-NGGNG, 3'-NNAGAAW, and 3-ACAY, and PAM sequences for Cpf1 include 5'-TTN (wherein N is defined as any nucleotide, W is defined as either A or T, and Y is defined as either C or T). Each gRNA comprises a sequence that is complementary to the target sequence (e.g., a Cas9 gRNA may comprise GN17-20GG). The gRNA may also comprise a scaffold sequence that forms a stem loop structure and a single-stranded region. The scaffold region may be the same in every gRNA. In some aspects, the gRNA may be a single molecule (i.e., sgRNA). In other aspects, the gRNA may be two separate molecules. Those skilled in the art are familiar with gRNA design and construction, e.g., gRNA design tools are available on the internet or from commercial sources.

A CRISPR system may comprise one or more nucleic acid binding domains associated with one or more, or two or more selected guide RNAs used to direct the CRISPR system to one or more, or two or more selected target nucleic acid loci. For instance, a nucleic acid binding domain may be associated with one or more, or two or more selected guide RNAs, each selected guide RNA, when complexed with a nucleic acid binding domain, causing the CRISPR system to localize to the target of the guide RNA.

iii. CRISPR Nickase Systems.

The programmable nucleic acid modification system may also be a CRISPR nickase system. CRISPR nickase systems are similar to the CRISPR nuclease systems described above except that a CRISPR nuclease of the system is modified to cleave only one strand of a double-stranded nucleic acid sequence. Thus, a CRISPR nickase in combination with a guide RNA of the system may create a single-stranded break or nick in the target nucleic acid sequence. Alternatively, a CRISPR nickase in combination with a pair of offset gRNAs may create a double-stranded break in the nucleic acid sequence.

A CRISPR nuclease of the system may be converted to a nickase by one or more mutations and/or deletions. For example, a Cas9 nickase may comprise one or more mutations in one of the nuclease domains, wherein the one or more mutations may be D10A, E762A, and/or D986A in the RuvC-like domain, or the one or more mutations may be H840A (or H839A), N854A and/or N863A in the HNH-like domain.

iv. ssDNA-Guided Argonaute Systems.

Alternatively, the programmable nucleic acid modification system may comprise a single-stranded DNA-guided Argonaute endonuclease. Argonautes (Agos) are a family of endonucleases that use 5'-phosphorylated short single-stranded nucleic acids as guides to cleave nucleic acid targets. Some prokaryotic Agos use single-stranded guide DNAs and create double-stranded breaks in nucleic acid sequences. The ssDNA-guided Ago endonuclease may be associated with a single-stranded guide DNA.

The Ago endonuclease may be derived from *Alistipes* sp., *Aquifex* sp., *Archaeoglobus* sp., *Bacteroides* sp., *Bradyrhizobium* sp., *Burkholderia* sp., *Cellvibrio* sp., *Chlorobium* sp., *Geobacter* sp., *Mariprofundus* sp., *Natronobacterium* sp., *Parabacteriodes* sp., *Parvularcula* sp., *Planctomyces* sp., *Pseudomonas* sp., *Pyrococcus* sp., *Thermus* sp., or *Xanthomonas* sp. For instance, the Ago endonuclease may be *Natronobacterium gregoryi* Ago (NgAgo). Alternatively, the Ago endonuclease may be *Thermus thermophilus* Ago (TtAgo). The Ago endonuclease may also be *Pyrococcus furiosus* (PfAgo).

The single-stranded guide DNA (gDNA) of an ssDNA-guided Argonaute system is complementary to the target site in the nucleic acid sequence. The target site has no sequence limitations and does not require a PAM. The gDNA generally ranges in length from about 15-30 nucleotides. The gDNA may comprise a 5' phosphate group. Those skilled in the art are familiar with ssDNA oligonucleotide design and construction.

v. Zinc Finger Nucleases.

The programmable nucleic acid modification system may be a zinc finger nuclease (ZFN). A ZFN comprises a DNA-binding zinc finger region and a nuclease domain. The zinc finger region may comprise from about two to seven zinc fingers, for example, about four to six zinc fingers, wherein each zinc finger binds three nucleotides. The zinc finger region may be engineered to recognize and bind to any DNA sequence. Zinc finger design tools or algorithms are available on the internet or from commercial sources. The zinc fingers may be linked together using suitable linker sequences.

A ZFN also comprises a nuclease domain, which may be obtained from any endonuclease or exonuclease. Non-limiting examples of endonucleases from which a nuclease domain may be derived include, but are not limited to, restriction endonucleases and homing endonucleases. The nuclease domain may be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. The type II-S nuclease domain may be modified to facilitate dimerization of two different nuclease domains. For example, the cleavage domain of FokI may be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. For example, one modified FokI domain may comprise Q486E, I499L, and/or N496D mutations, and the other modified FokI domain may comprise E490K, I538K, and/or H537R mutations.

vi. Transcription Activator-Like Effector Nuclease Systems.

The programmable nucleic acid modification system may also be a transcription activator-like effector nuclease (TALEN) or the like. TALENs comprise a DNA-binding domain composed of highly conserved repeats derived from transcription activator-like effectors (TALEs) that are linked to a nuclease domain. TALEs are proteins secreted by plant pathogen *Xanthomonas* to alter transcription of genes in host plant cells. TALE repeat arrays may be engineered via modular protein design to target any DNA sequence of interest. Other transcription activator-like effector nuclease systems may comprise, but are not limited to, the repetitive sequence, transcription activator like effector (RipTAL) system from the bacterial plant pathogenic *Ralstonia solanacearum* species complex (Rssc). The nuclease domain of TALEs may be any nuclease domain as described above in Section (I)(d)(i).

vii. Meganucleases or Rare-Cutting Endonuclease Systems.

The programmable nucleic acid modification system may also be a meganuclease or derivative thereof. Meganucleases are endodeoxyribonucleases characterized by long recognition sequences, i.e., the recognition sequence generally ranges from about 12 base pairs to about 45 base pairs. As a consequence of this requirement, the recognition sequence generally occurs only once in any given genome. Among meganucleases, the family of homing endonucleases named LAGLIDADG has become a valuable tool for the study of genomes and genome engineering. In some aspects, the meganuclease may be I-SceI or variants thereof. A meganuclease may be targeted to a specific nucleic acid sequence by modifying its recognition sequence using techniques well known to those skilled in the art.

The programmable DNA modification system having nuclease activity may be a rare-cutting endonuclease or derivative thereof. Rare-cutting endonucleases are site-specific endonucleases whose recognition sequence occurs rarely in a genome, preferably only once in a genome. The rare-cutting endonuclease may recognize a 7-nucleotide sequence, an 8-nucleotide sequence, or longer recognition sequence. Non-limiting examples of rare-cutting endonucleases include NotI, AscI, Pac, AsiSI, SbfI, and FseI.

viii. Optional Additional Domains.

The programmable nucleic acid modification system may further comprise at least one nuclear localization signal (NLS), at least one cell-penetrating domain, at least one reporter domain, and/or at least one linker.

In general, an NLS comprises a stretch of basic amino acids. Nuclear localization signals are known in the art (see, e.g., Lange et al., J. Biol. Chem., 2007, 282:5101-5105). The NLS may be located at the N-terminus, the C-terminal, or in an internal location of the fusion protein.

A cell-penetrating domain may be a cell-penetrating peptide sequence derived from the HIV-1 TAT protein. The cell-penetrating domain may be located at the N-terminus, the C-terminal, or in an internal location of the fusion protein.

A programmable nucleic acid modification system may further comprise at least one linker. For example, the programmable nucleic acid modification system, the nuclease domain of a protein, and other optional domains may be linked via one or more linkers. The linker may be flexible (e.g., comprising small, non-polar (e.g., Gly) or polar (e.g., Ser, Thr) amino acids). Examples of suitable linkers are well known in the art, and programs to design linkers are readily available (Crasto et al., Protein Eng., 2000, 13(5):3096-312). In alternate aspects, the programmable DNA modification protein, the cell cycle regulated protein, and other optional domains may be linked directly.

A programmable nucleic acid modification system may further comprise an organelle localization or targeting signal that directs a molecule to a specific organelle. A signal may be polynucleotide or polypeptide signal, or may be an organic or inorganic compound sufficient to direct an attached molecule to a desired organelle. Organelle localization signals can be as described in U.S. Patent Publication No. 20070196334, the disclosure of which is incorporated herein in its entirety.

(e) Site-Specific Recombination.

In some aspects, nucleic acid constructs of the disclosure comprise recombination recognition sequences flanking nucleic acid sequences for excising the nucleic acid sequences. In combination with a recombination system specific for the recombination recognition sequences, the recombination recognition sequences and any intervening nucleic acid sequences can be excised when the recombination system is expressed. Any recombination system capable of recognizing and excising a specific sequence can be used in the present disclosure. For instance, the excision system can be any of the nucleic acid modification systems described in Section I(d), modified to recognize the excision sequences and excise a nucleic acid sequence. The excision system can also be a recombinase system. A recombinase system comprises a recombinase enzyme that specifically recognizes and recombines a pair of short target recombination recognition sequences upstream and downstream of a nucleic acid sequence. Expression of the recombinase enzyme results in excision of any nucleic acid flanked by the upstream and downstream recombination sequences. Non-limiting examples of recombinase systems include, Cre-LoxP, VCre-V-LoxP, SCre-SLoxP, Vica-vox, Flp-FRT, Dre-Rox, λ-Int-attP, R-RRT, Kw-KwRT, Kd-KdRT, B2-B2RT, and B3-B3RT. In some aspects, the recombination sequences are LoxP and the DNA recombinase enzyme is Cre.

Figure 4A:
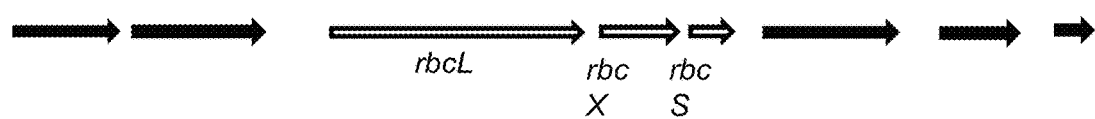
FIG. 4A. Transient delivery of Cre recombinase at the rbcLXS locus of PCC 7002. Schematic depicting the wild type rbcLXS operon of wt7002.
Figure 4B:
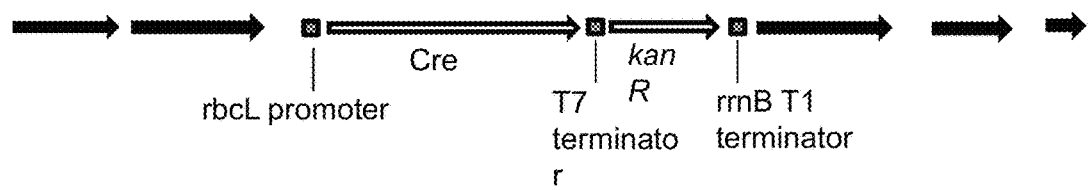
FIG. 4B. Transient delivery of Cre recombinase at the rbcLXS locus of PCC 7002. Schematic depicting the outcome of integrating the of Cre gene into the rbcLXS locus as a translational fusion of the rbcL promoter with kanR used for selection by kanamycin addition.

A schematic representation of an aspect of the system for genetically modifying a nucleic acid sequence of interest in *Synechococcus* PCC sp. 7002 depicting the second nucleic acid construct comprising LoxP recombination sequences and the first nucleic acid constructs comprising the Cre gene is shown in FIG. 4B.

(f) Regions of Homology.

The second and first constructs comprise upstream and downstream nucleic acid sequences homologous to the second or first locus. The upstream and downstream homologous sequences have substantial sequence identity to sequences located upstream and downstream of a locus in the genome of an organism. Because of these sequence similarities, the donor sequence may be integrated into (or exchanged with) a nucleic acid locus by homologous recombination. As used herein, the term "homologous" when used in reference to nucleic acid sequences, refers to sequences having at least about 75% sequence identity. Thus, the upstream and downstream sequences in the donor polynucleotide may have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with sequences upstream or downstream to the nucleic acid locus sequence.

As will be appreciated by those skilled in the art, the length of the donor polynucleotide can and does vary. For example, the construct sequence may vary in length from several base pairs to hundreds of base pairs to hundreds of thousands of base pairs. Each upstream or downstream sequence may range in length from about 20 base pairs to about 5000 base pairs. In some aspects, upstream and downstream sequences may comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 base pairs. In some aspects, upstream and downstream sequences may range in length from about 50 to about 1500 base pairs.

(g) Reporter.

The second and first nucleic acid constructs further comprise a second and first reporter to identify cells expressing the second or first construct. As used herein, the term "reporter" refers to any biomolecule that may be used as an indicator of transcription and/or translation through a promoter. A reporter may be a polypeptide. A reporter may also be a nucleic acid. Suitable polypeptide and nucleic acid reporters are known in the art, and may include visual reporters, selectable reporters, screenable reporters, and combinations thereof. Other types of reporters will be recognized by individuals of skill in the art.

Visual reporters typically result in a visual signal, such as a color change in the cell, or fluorescence or luminescence of the cell. Suitable visual reporters include fluorescent proteins, visible reporters, epitope tags, affinity tags, RNA aptamers, and the like. Non-limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato), or any other suitable fluorescent protein. Non-limiting examples of visual reporters include luciferase, alkaline phosphatase, beta-glucuronidase (GUS), beta-galactosidase, beta-lactamase, horseradish peroxidase, anthocyanin pigmentation, and variants thereof. Suitable epitope tags include, but are not limited to, myc, AcV5, AU1, AUS, E, ECS, E2, FLAG, HA, Maltose binding protein, nus, Softag 1, Softag 3, Strep, SBP, Glu-Glu, HSV, KT3, S, S1, T7, V5, VSV-G, 6×His, BCCP, and calmodulin. Non-limiting examples of affinity tags include chitin binding protein (CBP), thioredoxin (TRX), poly(NANP), tandem affinity purification (TAP) tag, and glutathione-S-transferase (GST). Non-limiting examples of RNA aptamers include fluorescent RNA aptamers that sequester small molecule dyes and activate their fluorescence, such as spinach, broccoli, mango, or biliverdin-binding variants thereof.

Other visual reporters may include fluorescent resonance energy transfer (FRET), lanthamide resonance energy transfer (LRET), fluorescence cross-correlation spectroscopy, fluorescence quenching, fluorescence polarization, scintillation proximity, chemiluminescence energy transfer, bioluminescence resonance energy transfer, excimer formation, phosphorescence, electrochemical changes, molecular beacons, and redox potential changes.

Selectable reporters typically confer a positively or negatively selectable trait to a cell, such as a drug resistance (e.g., antibiotic resistance) positive selection reporter. Examples of suitable selectable reporters include, without limit, herbicide resistance or tolerance such as resistance to glyphosate, glufosinate ammonium, bromoxynil, 2,4-dichlorophenoxyacetate (2,4-D), or sulfonylurea herbicides, antibiotic or chemical selectable reporters such as puromycin, zeomycin, streptomycin, chloramphenicol, gentamycin, kanamycin, neomycin, hydromycin, phleomycin, hygromycin, bleomycin, sulfonamide, bromoxynil, spectinomycin, methotrexate, and the like. Additional examples include dihydrofolate reductase, 5-eno/pyruvylshikimate-3-phosphate synthase, and acetolactate synthase, neomycin phosphotransferase I and II, cyanamide hydratase, aspartate kinase, dihydrodipicolinate synthase, bar gene, tryptophane decarboxylase, hygromycin phosphotransferase (HPT or HYG), dihydrofolate reductase (DHFR), phosphinothricin acetyltransferase, 2,2-dichloropropionic acid dehalogenase, acetohydroxyacid synthase, 5-enolpyruvyl-shikimate-phosphate synthase, haloarylnitrilase, acetyl-coenzyme A carboxylase, dihydropteroate synthase, and 32 kDa photosystem II polypeptide (psbA).

Additionally, selectable reporters can include environmental or artificial stress resistance or tolerance reporters including, but not limited to, high glucose tolerance, low phosphate tolerance, mannose tolerance, and/or drought tolerance, salt tolerance or cold tolerance. Reporters that confer environmental or artificial stress resistance or tolerance include, but are not limited to, trehalose phosphate synthase, phophomannose isomerase, *Arabidopsis* vacuolar H+-pyrophosphatase, AVPI, aldehyde resistance, and cyanamide resistance.

Other reporters may also be morphogenic reporters. A morphogenic reporter may be any reporter capable of inducing a morphogenic trait that may be used to identify and isolate successful products of homologous recombination. For instance, a morphogenic reporter may be used to activate proliferation of cells that have correct insertion in a desired target nucleic acid sequence of interest, when transcriptional activation of the target in the callus occurs. Such a reporter causes cells with the successful event to out-proliferate any other cell. Alternatively, a morphogenic reporter may be used to induce organogenesis by cells that have a correct homologous recombination event in a desired target nucleic acid sequence of interest, when transcriptional activation of the target in the callus occurs. Such a reporter causes cells with the successful event to produce a plant, instead thereby identifying the successful event. Non-limiting examples of morphogenic reporters include promoters of cellular proliferation. For instance, a morphogenic reporter may be a transcription factor that promotes stem cell proliferation or organogenesis.

It will be recognized that combinations of reporters may be used. For instance, a visual reporter fused to a protein expressed by the nucleic acid sequence of interest may be used to identify an accurate homologous recombination event, but the visual reporter is not permanently fused to the protein. A first reporter may be used in combination with the visual reporter, wherein the first reporter is permanently fused to the protein.

Additionally, irrespective of the reporter used in a donor polynucleotide, the reporter may be a split reporter system. Split reporter systems may be used to reduce the size of a reporter sequence introduced into a target nucleic acid locus. Non-limiting examples of suitable split reporter systems include split GFP systems, split 5-EnolpyruvylShikimate-3-Phosphate Synthase for glyphosate resistance, among others. Similarly, irrespective of the reporter used, a donor polynucleotide may encode an activator for activating a reporter encoded in a location other than the donor polynucleotide. For instance, a donor polynucleotide may encode an activator for activating a reporter encoded on nucleic acid sequences introduced into a cell with the donor polynucleotide.

II. Methods

One aspect of the present disclosure encompasses a method of genetically modifying at least one nucleic acid sequence of interest in a polyploid cell. The methods are based in part on exploiting polyploidy in a selection strategy based on polyploidy to modify the gene of interest. The methods can achieve full segregation of the genetic modification of the gene of interest. The methods can also achieve genetic modifications of a nucleic acid sequence without leaving behind a reporter (i.e., in a markerless manner). The method comprises using a system described in Section I.

The system can comprise at least one or at least two nucleic acid constructs. A system comprising at least one nucleic acid construct can be as described in Section I(b), and a system comprising at least two nucleic acid constructs can be as described in Section I(c). The one or more of the constructs can be plasmid-free.

(a) Methods Using One or More Constructs

When the nucleic acid modification system comprises a first nucleic acid modification system as described in Section I(b) above, the method comprises obtaining or having obtained the system, and introducing the first nucleic acid construct into the cell. The method further comprises identifying a homologous recombination event of the construct at the locus in the essential nucleic acid sequence by identifying a cell expressing the reporter. In some aspects, the first reporter is a selectable reporter, and identifying a homologous recombination event of the first construct with the gene of interest comprises selecting for expression of the reporter. In one aspect, the first reporter is gentamycin resistance, and identifying a homologous recombination event of the first construct with the gene of interest comprises identifying cells capable of growing in the presence of gentamycin. In another aspect, the first reporter is a zeocin resistance gene, and identifying a homologous recombination event of the first construct with the gene of interest comprises identifying cells capable of growing in the presence of gentamycin.

The cell is maintained under conditions for maintaining integration of the first construct into the essential nucleic acid sequence for a sufficient length of time for the nucleic acid modification system to modify the nucleic acid sequence of interest. Because the nucleic acid sequence is essential, the first construct cannot disrupt the expression of all copies of the nucleic acid sequence. In other words, integration of the first construct into the essential nucleic acid sequence cannot achieve full segregation. However, because the organism is polyploid, it is possible for an appropriate number of the copies of the nucleic acid sequence to be disrupted by integration of the first construct, all while a sufficient number of wild type copies of the nucleic acid sequence maintain sufficient expression of the nucleic acid sequence to allow survival of the organism. Accordingly, maintaining integration of the second construct into the essential nucleic acid sequence requires maintaining the cell under conditions suitable for expression of the first reporter to prevent excision of all copies of the first construct from the first locus and reverting the nucleic acid sequence to a wild type genotype.

In some aspects, the first reporter is a selectable reporter, and identifying a homologous recombination event of the first construct for insertion into the essential nucleic acid sequence comprises selecting for expression of the selectable reporter.

In some aspects, the method further comprises confirming that the at least one nucleic acid sequence of interest is modified. For example, if modifying a nucleic acid sequence of interest comprises expression of a fluorescent reporter, the cells are maintained under selection until the reporter is expressed.

Figure 10A:
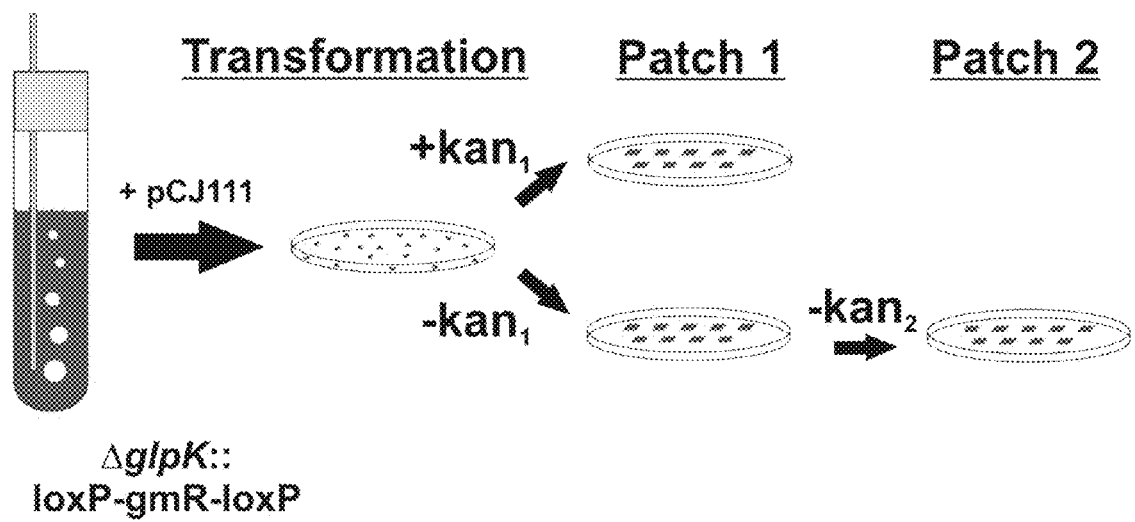
FIG. 10A. Determination of the loss of Cre from the rbcLXS locus in the absence of kanamycin selection. Patching workflow to determine the loss of Cre from the rbcLXS locus in the absence of kanamycin selection. The ΔglpK::loxP–gmR–loxP strain was transformed with the plasmid pCJ111, which encodes for Cre recombinase and a kanamycin resistance cassette and integrates into the rbcLXS locus by allelic exchange. From the initial transformation plate that contains 100 microgram/ml kanamycin colonies are patched onto plates that do not contain any kanamycin ($-kan_1$) or that contain 100 microgram/ml kanamycin ($+kan_1$). Once the second patches grown in the absence of kanamycin have reached maturity they are subsequently repatched onto a fresh agar plate that also does not contain kanamycin ($-kan_2$). Patches are then analyzed by colony PCR to test for the loss of the second nucleic acid construct.

The method further comprises conditions for maintaining expression of the first reporter. Because the first nucleic acid sequence is essential for survival of the organism, removing the conditions for maintaining expression of the first reporter relieves the selection for integration of the first construct into the essential gene, resulting in excision of the construct to restore a wild type essential nucleic acid sequence. The method then comprises identifying a cell that fails to express the first reporter, thereby generating a cell with at least one genetically modified nucleic acid sequence of interest. In one aspect, identifying a cell that fails to express the first reporter can be as depicted in FIG. 10A. In some aspects, the method further comprises confirming the absence of the first construct from the locus in the essential gene.

(b) Methods Using Two or More Constructs.

Figure 3A:
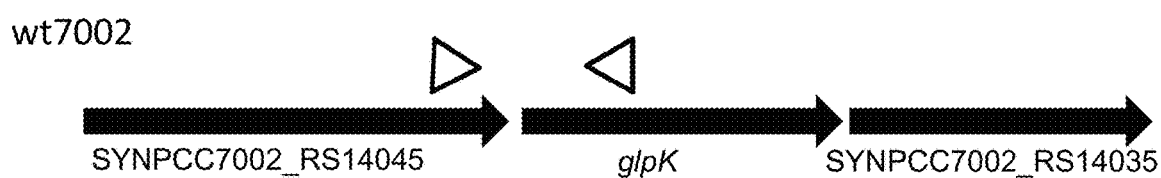
FIG. 3B. Schematic of the PCC 7002 ΔglpK::loxP::gmR::loxP locus. Schematic depicting the outcome of integrating the gentamycin resistance gene flanked by the loxP recombinase recognition sequences described as ΔglpK::loxP::gmR::loxP at the glpK locus. Solid arrowheads depict the gentamycin (gmR) specific primers.
FIG. 3C. Segregation of the PCC 7002 ΔglpK::loxP::gmR::loxP strain. Colony PCR analysis of ΔglpK::loxP::gmR::loxP transformants with both the glpK-specific primers (glpk+ primers) and gmR-specific primers (gent+ primers).
Figure 3B:
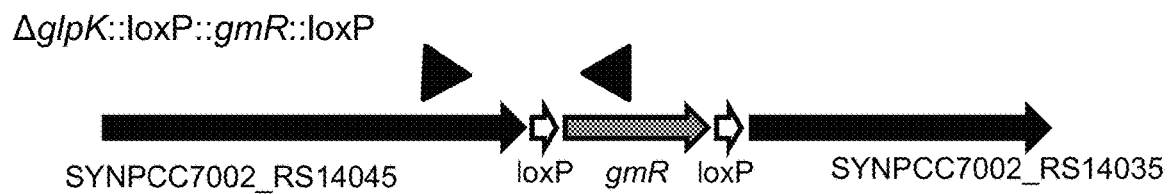
Figure 14:
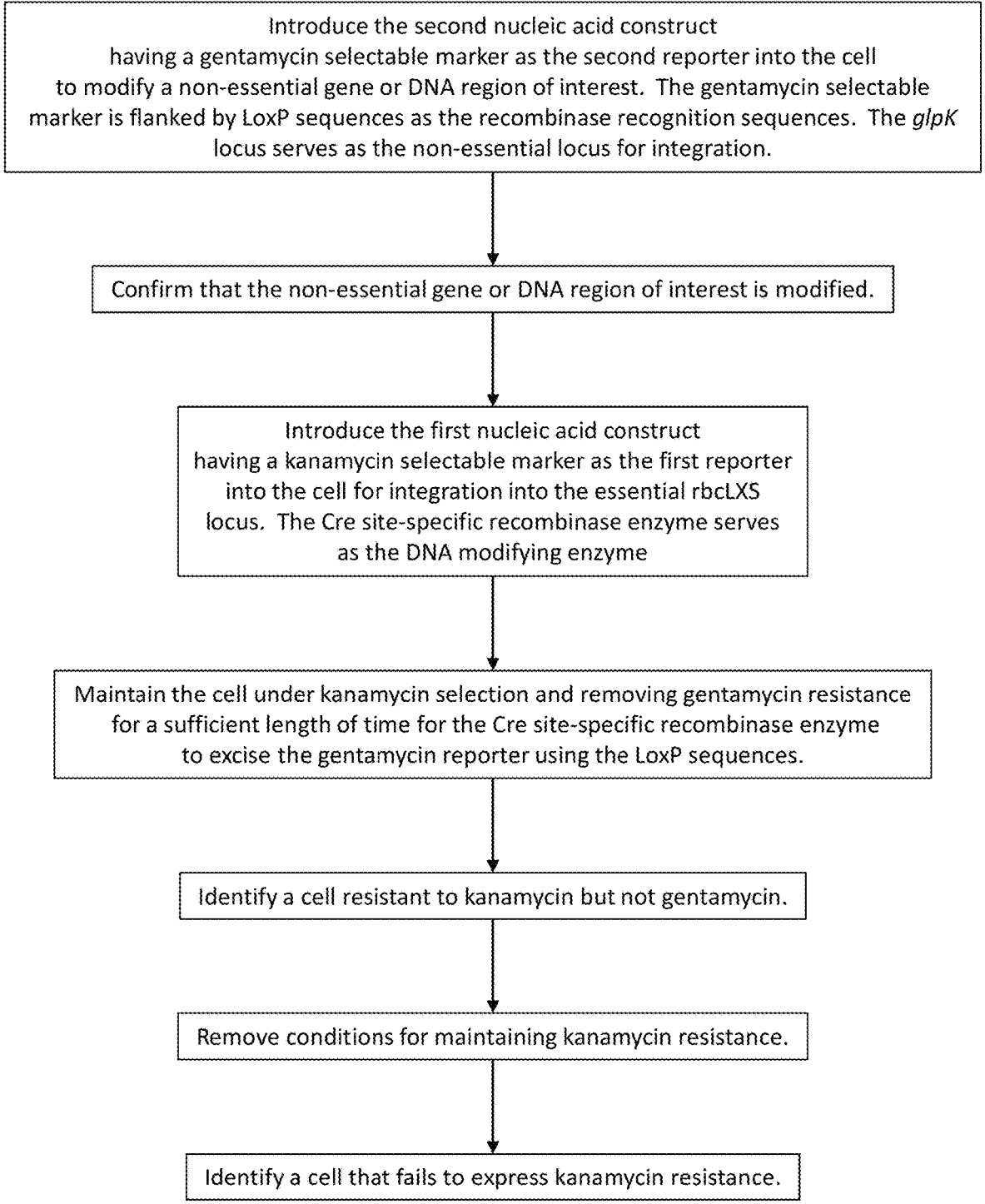
FIG. 14. Overview of an example workflow. A flow chart of one aspect of a method of the disclosure employing the first and second constructs depicted in FIG. 2.

When the nucleic acid modification system comprises a first and a second nucleic acid modification system as described above, an aspect of the present disclosure encompasses a method of genetically modifying at least one nucleic acid sequence of interest in a polyploid cell. The method comprises using the system described in Section I(c). A flow chart depicting an aspect of a method of the disclosure depicted in FIG. 2 and FIGS. 3A-3B is shown in FIG. 14.

The method comprises introducing the second nucleic acid construct of the system into a polyploid cell and identifying a homologous recombination event of the second construct at the second locus by identifying a cell expressing the second reporter. In some aspects, the second reporter is a selectable reporter, and identifying a homologous recombination event of the second construct with the nucleic acid sequence of interest comprises selecting for expression of the reporter. In one aspect, the second reporter is gentamycin resistance, and identifying a homologous recombination event of the second construct with the nucleic acid sequence of interest comprises identifying cells capable of growing in the presence of gentamycin.

The method further comprises introducing the first nucleic acid construct into the cell, and identifying a homologous recombination event of the first construct at a locus in the essential nucleic acid sequence by identifying a cell expressing the first reporter. Because the nucleic acid sequence is essential, the first construct cannot disrupt the expression of all copies of the nucleic acid sequence. In other words, integration of the first construct into the essential nucleic acid sequence cannot achieve full segregation. However, because the organism is polyploid, it is possible for an appropriate number of the copies of the nucleic acid sequence to be disrupted by integration of the first construct, all while a sufficient number of wild type copies of the nucleic acid sequence maintains sufficient expression of the nucleic acid sequence to allow survival of the organism. Accordingly, maintain integration of the first construct into the essential nucleic acid sequence requires maintaining the cell under conditions suitable for expression of the first reporter to prevent excision of all copies of the first construct from the first locus and reverting the nucleic acid sequence to a wild type genotype.

In some aspects, the first reporter is a selectable reporter, and identifying a homologous recombination event of the first construct for insertion of the construct into the essential nucleic acid sequence comprises selecting for expression of the selectable reporter.

The cell is then maintained under conditions for continuing expression of the first reporter and removing conditions for maintaining expression of the second reporter for a sufficient length of time for the site-specific recombination system to excise the second reporter. In some aspects, the method further comprises confirming excision of the second reporter from the second locus.

The method further comprises identifying a cell that expresses the first reporter and fails to express the second reporter. For example, if the second reporter is a fluorescent reporter, the cells can be identified by identifying cells that fail to fluoresce. Alternatively, if the second reporter is a selectable marker, the cells can be identified by identifying cells incapable of growth on media comprising the selectable marker.

When a cell that expresses the first reporter and fails to express the second reporter is identified, conditions for maintaining expression of the first reporter are removed. Because the first nucleic acid sequence is essential for survival of the organism, removing the conditions for maintaining expression of the first reporter relieves the selection for integration of the first construct into the essential nucleic acid sequence, resulting in excision of the first construct to restore full expression of the essential nucleic acid sequence. The method then comprises identifying a cell that fails to express the first reporter, thereby generating a cell with at least one genetically modified nucleic acid sequence of interest. In one aspect, identifying a cell that fails to express the first reporter can be as depicted in FIG. 6. In some aspects, the method further comprises confirming the absence of the first construct from the locus in the essential nucleic acid sequence.

Methods of confirming an integration event and an excision event into the genome of an organism are known in the art. For instance, PCR using primers flanking a specific sequence can be performed, to confirm the present or absence of an integrated or excised nucleic acid sequence.

(a) Introduction into the Cell.

The method comprises introducing nucleic acid constructs of the disclosure into a cell of interest. The constructs may be introduced into the cell as a purified isolated composition, purified isolated components of a composition, as one or more nucleic acids comprising the second and first nucleic acid constructs, or components of the second and first nucleic acid constructs, and combinations thereof.

When a system comprises more than one nucleic acid construct, the nucleic acid constructs (or nucleic acids comprising the nucleic acid constructs) can be simultaneously introduced into a cell. Alternatively, the nucleic acid constructs can be introduced separately. For instance, when the system comprises a first nucleic acid construct encoding a site-specific recombination system and a second construct encoding a recombination recognition sequences, the first and second nucleic acid constructs are introduced sequentially. In an aspect, when the nucleic acid modification system is Cre-LoxP, the second and first nucleic acid constructs are introduced into the cell sequentially.

The second and first nucleic acid constructs described above may be introduced into the cell by a variety of means. Suitable delivery means include microinjection, electroporation, sonoporation, biolistics, calcium phosphate-mediated transfection, cationic transfection, liposomes and other lipids, dendrimer transfection, heat shock transfection, nucleofection transfection, gene gun delivery, dip transformation, supercharged proteins, cell-penetrating peptides, implantable devices, magnetofection, lipofection, impalefection, optical transfection, proprietary agent-enhanced uptake of nucleic acids, *Agrobacterium tumefaciens* mediated foreign gene transformation, proprietary agent-enhanced uptake of nucleic acids, and delivery via liposomes, immunoliposomes, virosomes, or artificial virions. In an aspect, when the polyploid organism is *Synechococcus* cell, the second and first nucleic acid constructs are introduced into the cell via the natural competency of the cell.

(b) Culturing a Cell.

The method further comprises maintaining the cell under appropriate conditions such that a recombination event occurs. In general, the cell is maintained under conditions appropriate for cell growth and/or maintenance. Suitable cell culture conditions are well known in the art and are described, for example, in Stevens et al. (1973) J. Phycol. 9:427-430; Santiago et al. (2008) PNAS 105:5809-5814; Moehle et al. (2007) PNAS 104:3055-3060; Urnov et al. (2005) Nature 435:646-651; and Lombardo et al. (2007) Nat. Biotechnology 25:1298-1306; Taylor et al. (2012) Tropical Plant Biology 5: 127-139, the disclosures of which are incorporate herein in their entirety. Those of skill in the art appreciate that methods for culturing cells are known in the art and may and will vary depending on the cell type. Routine optimization may be used, in all cases, to determine the best techniques for a particular cell type.

(c) Identification of an Accurate Homologous Recombination Event.

The method further comprises identifying an accurate homologous recombination event. The accurate homologous recombination event may be identified by identifying a cell expressing the reporter. Methods of identifying a cell expressing a reporter may and will vary depending on the reporter, the cell, the tissue or the organism comprising the cell, among others. For instance, if a reporter is a visual reporter, a cell expressing a reporter may be identified by observing a visual signal in the cell. If a reporter is a selectable reporter such as antibiotic resistance, a cell expressing a reporter may be identified by selecting an antibiotic resistant cell.

Upon confirmation that an accurate homologous recombination event has occurred, single cell clones may be isolated. Additionally, cells comprising one accurate homologous recombination event may undergo one or more additional rounds of targeted modification to modify additional nucleic acid loci sequences.

III. Kits

A further aspect of the present disclosure provides kits comprising the system detailed above in Section I, wherein at least one of the nucleic acid constructs encodes a nucleic acid modification system for modifying a nucleic acid sequence of interest in a polyploid organism. Alternatively, the kit may comprise one or more cells comprising the system.

The kits may further comprise transfection reagents, cell growth media, selection media, in-vitro transcription reagents, nucleic acid purification reagents, protein purification reagents, buffers, and the like. The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A "genetically modified" cell refers to a cell in which the nuclear, organellar or extrachromosomal nucleic acid sequences of a cell have been modified, i.e., the cell contains at least one nucleic acid sequence that has been engineered to contain an insertion of at least one nucleotide, a deletion of at least one nucleotide, and/or a substitution of at least one nucleotide.

The terms "genome modification" and "genome editing" refer to processes by which a specific nucleic acid sequence in a genome is changed such that the nucleic acid sequence is modified. The nucleic acid sequence may be modified to comprise an insertion of at least one nucleotide, a deletion of at least one nucleotide, and/or a substitution of at least one nucleotide. The modified nucleic acid sequence is inactivated such that no product is made. Alternatively, the nucleic acid sequence may be modified such that an altered product is made.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "full segregation" refers to the modification of all copies of a target nucleic acid site in a polyploid cell.

The term "plasmid free" refers to a construct not contained in a plasmid capable of replicating in an organism of choice. However, it will be recognized that plasmids can be used during construction and preparation of the construct as practiced in the art using recognized laboratory techniques.

As used herein, the term "gene" means a segment of DNA that contains all the information for the regulated biosynthesis of an RNA product, including promoters, exons, introns, and other untranslated regions that control expression.

As used herein, the term "locus" means a location on a chromosome or DNA molecule corresponding to a gene or a physical or phenotypic feature.

As used herein, the term "encode" is understood to have its plain and ordinary meaning as used in the biological fields, i.e., specifying a biological sequence. The term "encode," when used to describe the function of nucleic acid molecules, customarily means to identify one single amino acid sequence that makes up a unique polypeptide, or one nucleic acid sequence that makes up a unique RNA. That function is implemented by the particular nucleotide sequence of each nucleic acid molecule. In this aspect, the term "encode" refers to a reporter operably linked to the regions of homology such that the reporter is expressed upon accurate homologous recombination into the nucleic acid sequence of interest and upon transcription activation of the nucleic acid sequence of interest comprising the locus of interest. As used herein, the term "express" refers to the conversion of DNA sequence information into messenger RNA (mRNA) and/or protein. In this aspect, the term "express" refers to production of a detectable reporter signal as a result of an accurate homologous recombination event and transcription activation of the nucleic acid sequence of interest.

A shuttle vector is a vector (usually a plasmid) constructed so that it can propagate in more than one host species. Therefore, DNA inserted into a shuttle vector can be tested or manipulated in two different cell types.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms may encompass known analogs of natural nucleotides, as well as nucleotides that are modified in the base, sugar and/or phosphate moieties. In general, an analog of a particular nucleotide has the same base-pairing specificity, i.e., an analog of A will base-pair with T. The nucleotides of a nucleic acid or polynucleotide may be linked by phosphodiester, phosphothioate, phosphoramidite, phosphorodiamidate bonds, or combinations thereof.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As used herein, the terms "target site", "target sequence", or "nucleic acid locus" refer to a nucleic acid sequence that defines a portion of a nucleic acid sequence to be modified or edited and to which a homologous recombination composition is engineered to target.

The terms "upstream" and "downstream" refer to locations in a nucleic acid sequence relative to a fixed position. Upstream refers to the region that is 5' (i.e., near the 5' end of the strand) to the position, and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a first nucleotide or amino acid sequence. Genomic sequences may also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). one implementation of this algorithm to determine percent identity of a sequence is provided by the Genetics Computer Group (Madison, Wis.)

in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Genome Engineering of *Synechococcus* sp. PCC 7002 Using the rbcLXS Locus as a Natural Counter-Selection System A method is described for genetic engineering of polyploid organisms in a plasmid-free and markerless manner using methods of natural counter-selection developed by the inventors. Using essential genes are integration loci, gene(s) encoding different nucleic acid modifying systems of interest can be delivered to and transiently maintained in the host by conventional antibiotic selection, allowing their expression and subsequent genome engineering. For polyploid organisms, use of genes in this capacity imposes no negative effects on the host cell. After the desired genome modification(s) is complete, the DNA modifying gene(s) are quickly and efficiently removed from the host by simple removal of the antibiotic selection. This approach eliminates the need for replicative plasmids and conventional counter-selection methods, and eliminates the persistence of undesirable genetic artifacts associated with conventional genome engineering methods.

Specific use of an essential gene for the transient integration and expression of a nucleic acid modifying systems in polyploid organisms dispenses with the need for both stable replicative plasmids and counter-selection systems, which represent an aspect of conventional genome engineering applications. Furthermore, by reducing the complexity of the steps involved, cost and time savings also result.

A schematic representation of an aspect of a system for genetically modifying at least one nucleic acid sequence of interest in a polyploid organism (FIG. 1). The system exploits polyploidy as an inherent counter-selection strategy in order to transiently introduce and express a DNA modification system in order to modify the nucleic acid sequence of interest in a markerless manner. Retention or loss of DNA modification system in the targeted essential nucleic acid sequence is transiently controlled by the presence or absence of a chosen antibiotic.

Figure 3C:

The cyanobacterium *Synechococcus* sp. PCC 7002 (wt7002) was chosen to provide a model polyploid host cell. To provide a model chromosomal target for genome engineering, a gene conferring gentamycin resistance flanked by two loxP sites is first introduced into the glpK neutral (nonessential) site of wt7002 by homologous recombination. FIG. 3A shows a construct having wild type genomic locus of the glpK neutral site in wt7002 along with the integration of the loxP–flanked gentamycin resistance cassette, described as ΔglpK::loxP::gmR::loxP (FIG. 3B). In FIG. 3A, white arrowheads depict the glpK-specific primers. In FIG. 3B, black arrowheads depict the gentamycin (gmR) specific primers (referred to as 'glpK+ primers' and 'gent+ primers', respectively). The absence of a PCR product using the 'glpK+ primers' and the presence of PCR product using the 'gent+ primers' in FIG. 3C is indicative of full segregation, i.e., transformants 2-6 in FIG. 3C are segregated. This result demonstrates that successful integration and full segregation of the gentamycin resistance gene was achieved, resulting in the deletion of glpK.

Figure 5:
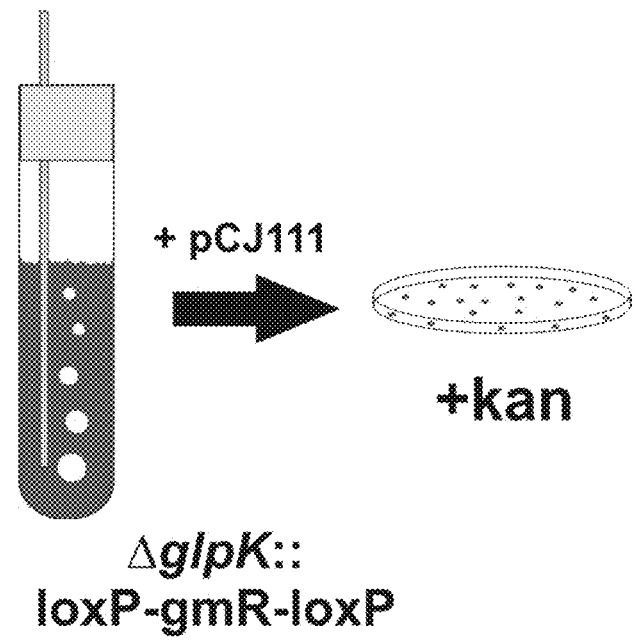
FIG. 5. Integrating a nucleic acid construct into rbcLXS does not negatively affect he transformation efficiency. A schematic illustrating the transformation of a ΔglpK::loxP::gmR::loxP strain with pCJ111, a plasmid carrying a construct composed of the genes encoding Cre recombinase and kanamycin resistance and that integrates into the rbcLXS locus. The graph compares the transformation efficiency when integrating a construct composed of the genes encoding Cre recombinase and kanamycin resistance into either the glpK neutral site or into the essential gene rbcLXS. These data are not statistically significantly different from each other.
Figure 5:
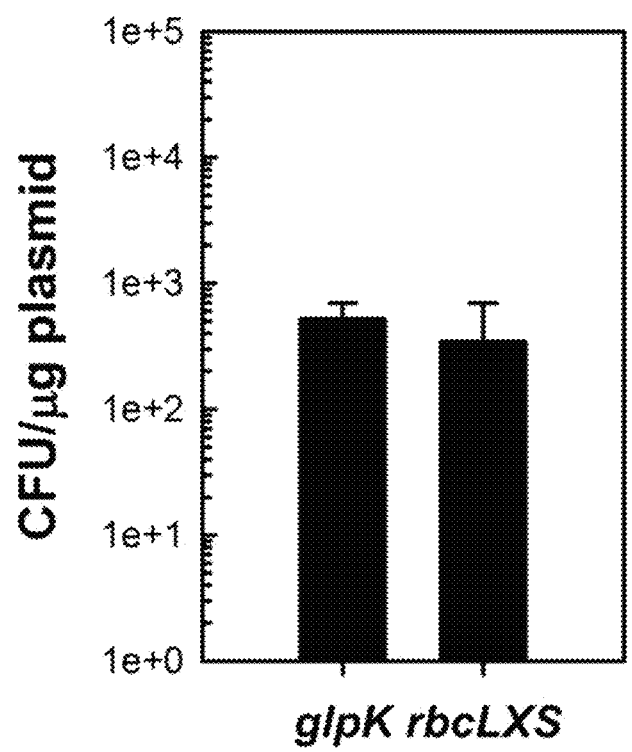

A plasmid was generated containing the following: a translational fusion of the gene encoding Cre recombinase from *Saccharomyces cerevisiae* to the native rbcL gene, a kanamycin resistance gene, and homology arms for allelic exchange into rbcLXS. This plasmid contains the cassette needed to introduce the ΔrbcLXS::$p_{rbcl}$Cre::kanR mutations and is referred to as pCJ111. FIG. 4A shows a construct having wild type genomic locus of the rbcLXS locus in wt7002. Following homologous recombination of this cassette into the chromosomal rbcLXS operon, this would result in the construction of a strain with the follow additional mutation: ΔrbcLXS::$p_{rbcl}$Cre::kanR (FIG. 4B). Clones carrying this mutation were selected for on the basis of kanamycin resistance. Per this design, Cre is expressed via the high activity of the rbcL promoter, eliminating the need for a chemical inducer, and better ensuring both efficient translation initiation and effective expression of the Cre gene product. Although the rbcLXS operon is essential for survival of the organism, the resulting transformation efficiency, as determined by the number of kanamycin resistant colonies per microgram of DNA, was not significantly different from the transformation efficiency of wt7002 with an analogous construct that instead integrates into the glpK neutral site (FIG. 5). This demonstrates the important finding that integration of a DNA cassette into an essential gene (such as rbcLXS) in a polyploid organism can be achieved with negligible fitness defects.

Figure 6A:
FIG. 6A. Gene schematic of the glpK neutral site in PCC 7002. The gene schematic of the glpK neutral site in wt7002 is depicted. Black arrowheads primers specific to the periphery of the glpK neutral site used for are colony PCR, which produce a 2261 bp product if glpK is present.
Figure 6B:
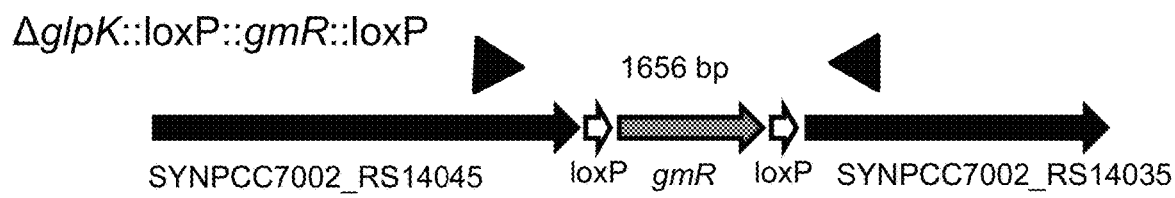
FIG. 6B. Gene schematic of the ΔglpK::loxP::gmR::loxP strain. Schematic illustrating the ΔglpK:loxP::gmR::loxP genomic locus when the strain is not also transformed with plasmid pCJ111. Blank arrowheads primers specific to the periphery of the glpK neutral site used for are colony PCR, which produce a 1656 bp product if gmR is present.
Figure 6C:
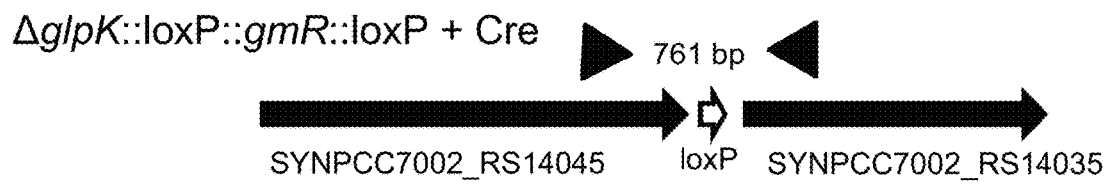
FIG. 6C. Gene schematic of the ΔglpK::loxP strain. Schematic illustrating the ΔglpK::loxP:gmR::loxP genomic locus after the strain is then also transformed with plasmid pCJ111. Black arrowheads primers specific to the periphery of the glpK neutral site used for are colony PCR, which produce a 761 bp only if Cre is also expressed and active.
Figure 7:
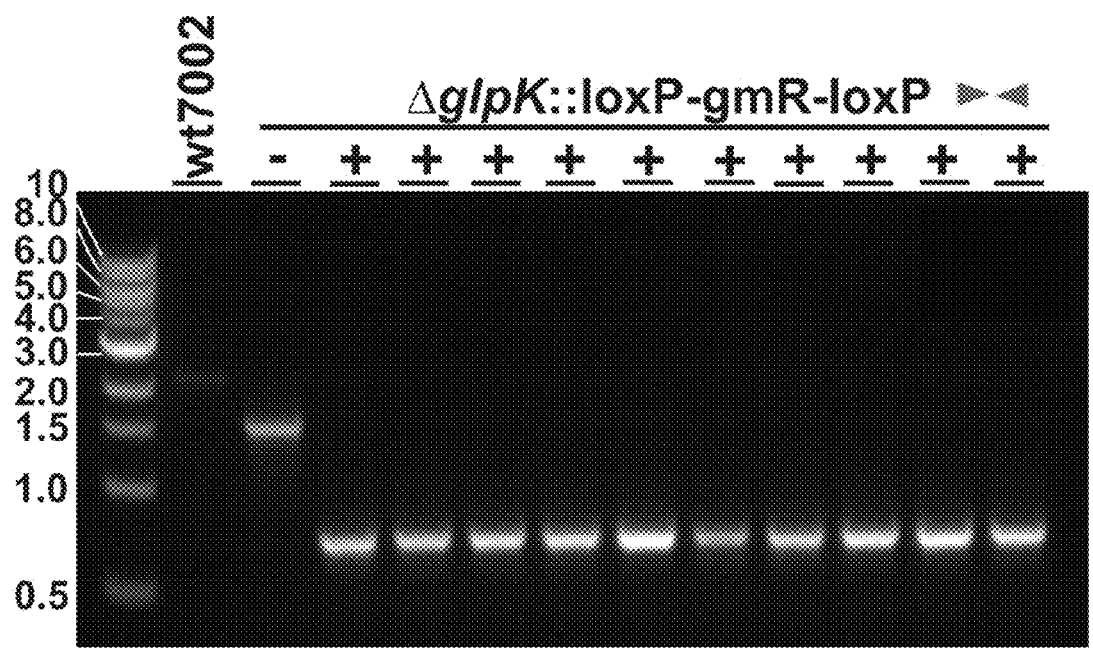
FIG. 7. Cre recombinase is 100% active in PCC 7002 when expressed from the rbcLXS locus. The gipK locus of the ΔglpK:loxP–gmR–loxP strain is shown. wt7002 represents the wild type glpK locus. '–' represents the strain not transformed with pCJ111. '+' represents the strain that is transformed with pCJ111. Green and pink heads represent PCR primers used to determine Cre recombinase activity. The gel demonstrates the colony PCR results from the indicated strains. wt7002 gives a band 2261 bp in size. ΔglpK:loxP–gmR–loxP–Cre or '–' gives a band 1656 bp in size. ΔglpK::loxP–gmR–loxP+Cre or '+' gives a band 761 bp in size.
Figure 7:
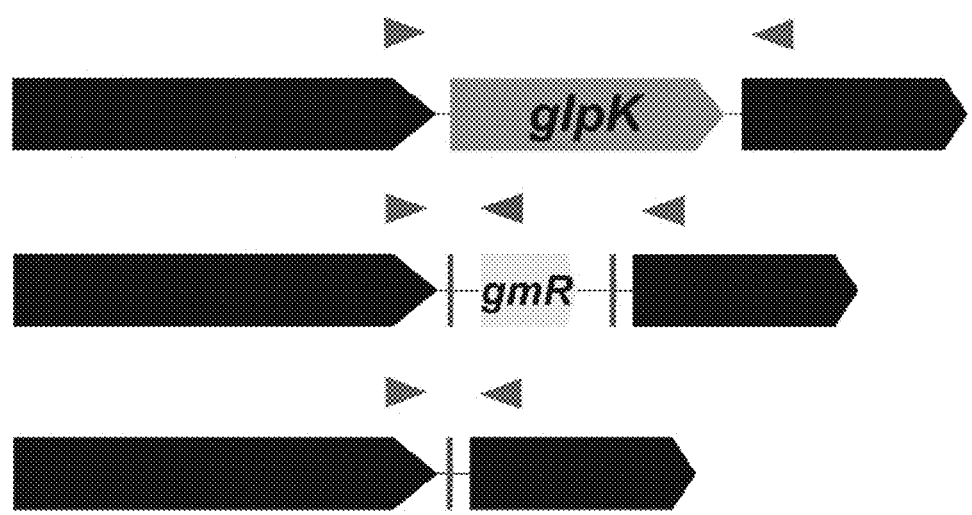
Figure 8:
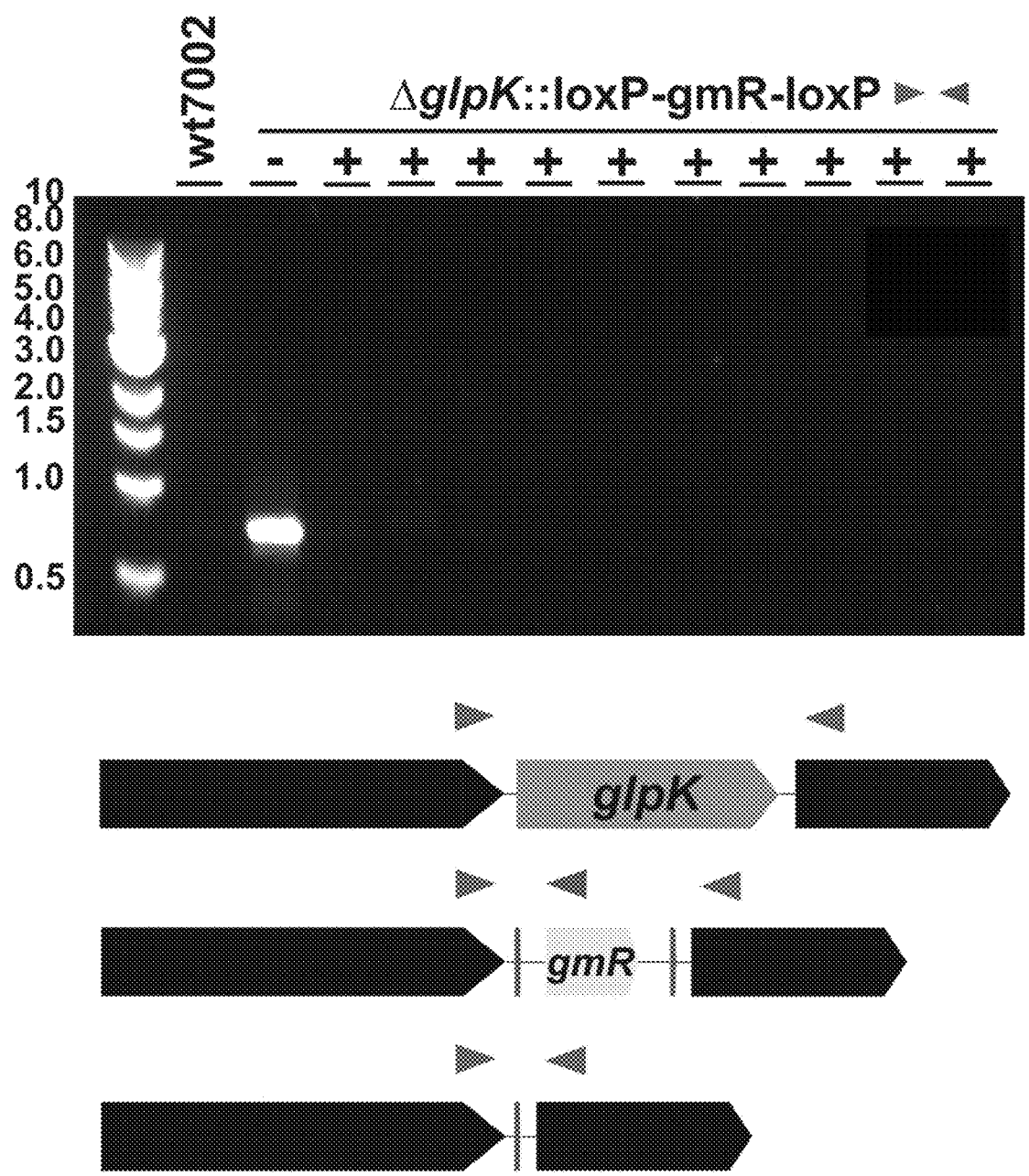
FIG. 8. PCR Validation of removal of the gentamycin resistance marker by Cre recombinase in PCC 7002. The glpK locus of the ΔglpK::loxP–gmR–loxP strain is shown. wt7002 represents the wild type glpK locus. '–' represents the strain not transformed with pCJ111. '+' represents the strain that is transformed with pCJ111. The green and pink arrowheads represent PCR primers used to determine loss of the gentamycin resistance marker. The gel demonstrates the colony PCR results from the indicated strains. wt7002 does not give a PCR product when tested with the indicated primer pair. ΔglpK::loxP–gmR–loxP–Cre or '–' gives a band 750 bp in size. ΔglpK::loxP–gmR–loxP+Cre or '+' does not give a PCR product when tested with the indicated primer pair.

Determination of whether or not Cre recombinase was active when it was expressed from the rbcLXS locus was done by assaying the loss of the gentamycin resistance gene from the test strain by 2 independent methods. Second, colony PCR was performed on 10 individual transformants and with two different primer pairs. The second primer pair would amplified a product outside the glpK gene 2261 bp in size (FIG. 6A). In the ΔglpK::loxP::gmR::loxP strain not transformed with pCJ111 this same primer pair would produce a product 1656 bp in size (FIG. 6B). However in the ΔglpK::loxP::gmR::loxP strain transformed with pCJ111 the expected band would be 761 bp in size (FIG. 6C). As seen in FIG. 7, all cells transformed with pCJ111 and carrying the Cre expression cassette subsequently lost the gentamycin resistance gene that was integrated at the glpK site. This assay indicates that Cre recombinase expressed in this fashion displays high activity. A first primer pair amplifies a product only when the gentamycin cassette is present. As seen in FIG. 8 only the ΔglpK::loxP::gmR::loxP strain that was not transformed with pCJ111 produces a product using this primer pair.

Figure 9A:
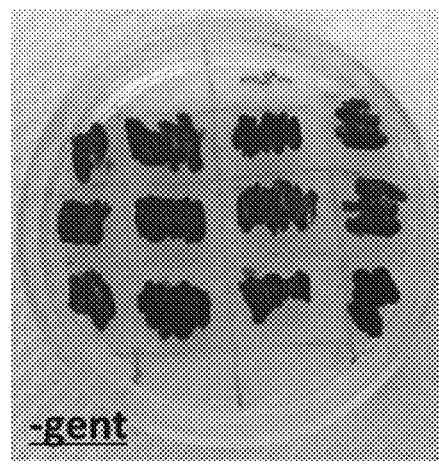
FIG. 9A. Phenotypic validation of the removal of the gentamycin resistance marker by Cre recombinase expressed from the rbcLXS locus. Patches of either wt7002, ΔglpK:loxP–gmR–loxP–Cre, or 10 individual patches of ΔglpK:loxP–gmR–loxP+Cre were streaked onto agar plates containing no antibiotics.
Figure 9B:
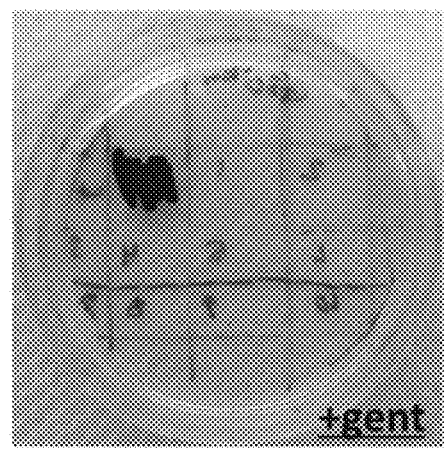
FIG. 9B. Phenotypic validation of the removal of the gentamycin resistance marker by Cre recombinase expressed from the rbcLXS locus. Patches of either wt7002, ΔglpK:loxP–go-loxP–Cre, or 10 individual patches of ΔglpK::loxP–gmR–loxP+Cre were streaked onto agar plates containing 30 microgram/ml gentamycin.
Figure 9C:
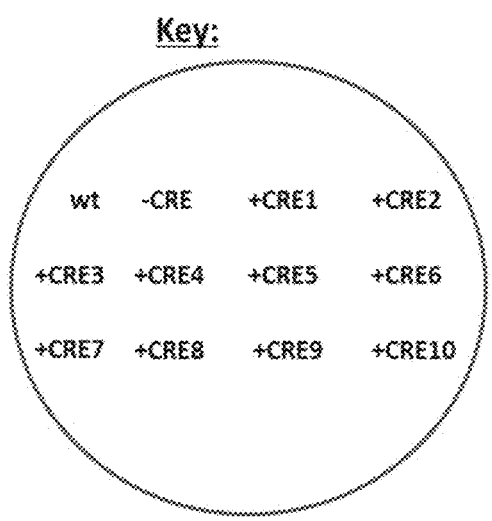
FIG. 9C. Phenotypic validation of the removal of the gentamycin resistance marker by Cre recombinase expressed from the rbcLXS locus. Patching key for FIG. 9A and FIG. 9B.

Loss of the gentamycin resistance gene integrated in the glpK locus should also render cells sensitive to gentamycin. All 10 transformants were patched on media A+ agar plates containing either 0 microgram/ml gentamycin (FIG. 9A) or 30 microgram/ml gentamycin (FIG. 9B; see FIG. 9C for a guide). As can be seen, only the strain not transformed with pCJ111 was able to grow in the presence of gentamycin, while wt7002 as well as those transformed with pCJ111 could only grow in the absence of gentamycin. Taken together, these data suggest that the Cre recombinase is fully active in Synechococcus sp. PCC 7002 and that Cre-dependent recombination can be used to excise a selection marker flanked by LoxP occurs after expressing Cre from a nucleic acid construct integrated into a locus consisting of an essential gene. Furthermore, with a sample size of n=10, these results demonstrate that Cre recombinase is active in PCC 7002 and enables efficient genome engineering of target sequences of interest.

Figure 10B:
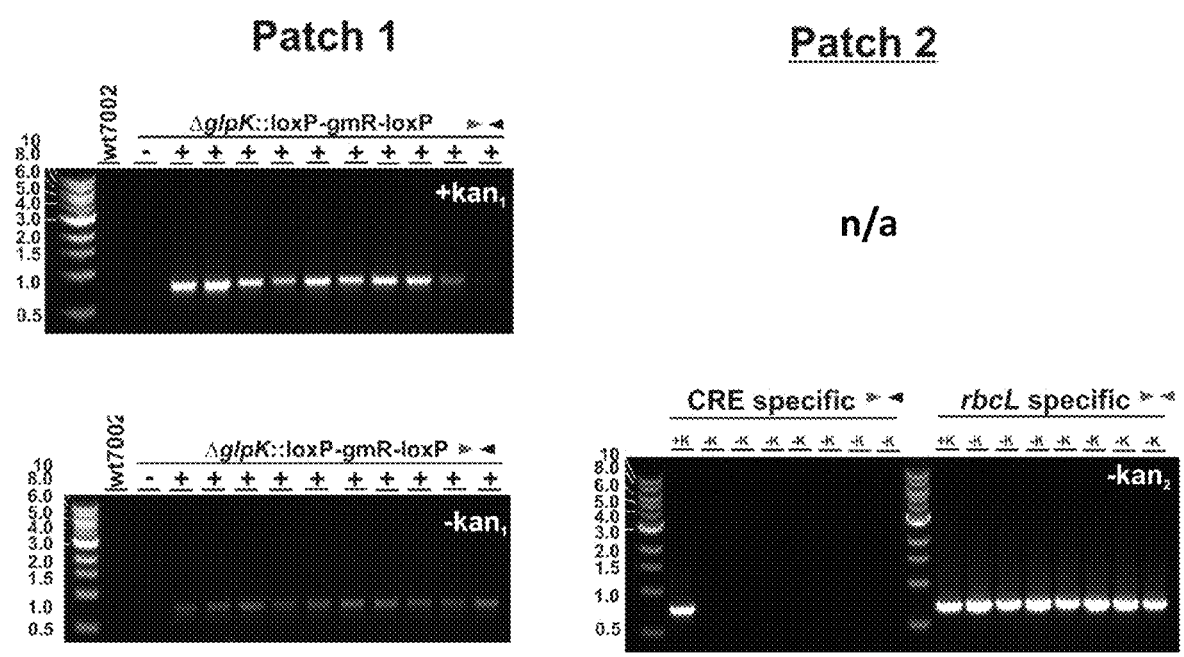
FIG. 10B. Determination of the loss of Cre from the rbcLXS locus in the absence of kanamycin selection. Colony PCR results from the patching experiment described in FIG. 10A. PCR primer pair colors are given in FIG. 10C. A positive band indicates the presence of Cre at the rbcLXS locus, the absence of a band indicates the absence of Cre at the rbcLXS locus. 'n/a', Not applicable.
Figure 10C:
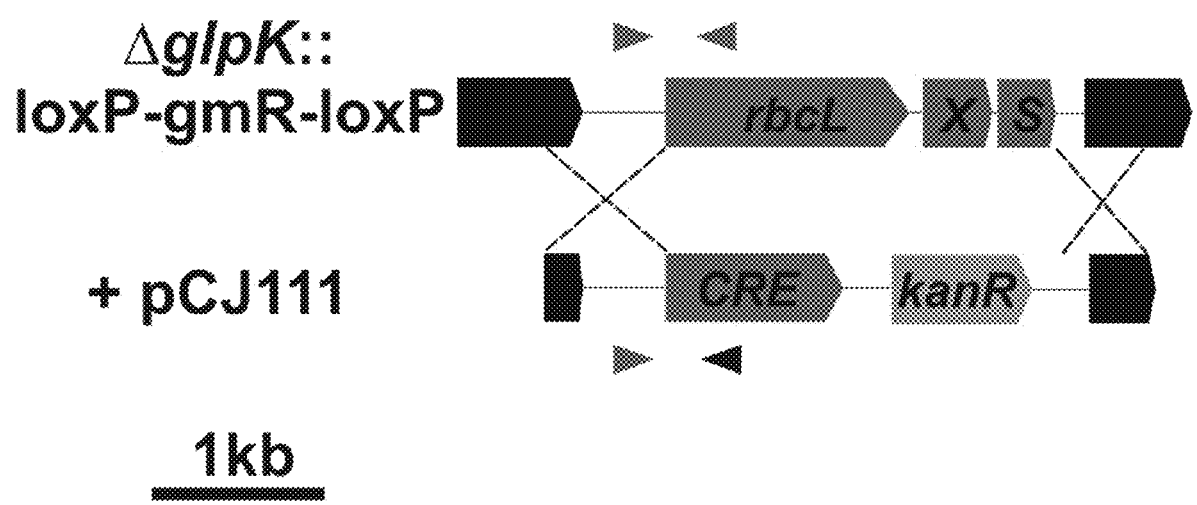
FIG. 10C. Determination of the loss of Cre from the rbcLXS locus in the absence of kanamycin selection. Cre recombinase was integrated into the rbcLXS locus using kanamycin selection. ΔglpK::loxP–gmR–loxP represents a strain that has a loxP flanked gentamycin resistance cassette integrated into the glpK locus. pCJ111 represents the plasmid used to transform the ΔglpK::loxP–gmR–loxP strain and encodes Cre recombinase as well as a kanamycin resistance cassette and integrates into the rbcLXS locus in PCC 7002 via allelic exchange. Blue and black arrowheads represent PCR primers used to determine the presence or absence of the integration product.

To then remove the integrated DNA cassette containing the genes encoding Cre recombinase and kanamycin resistance from the rbcLXS locus, cells still carrying the genes encoding Cre recombinase and kanamycin resistance were patched onto solid agar media A+ plates either with or without kanamycin (FIG. 10A). As depicted, re-patching of surviving clones onto plates without kanamycin continued until the Cre recombinase gene was no longer detectable by colony PCR. As seen in FIG. 10B, for all of 8 unique clones, only 2 patching events were required in this case for the Cre recombinase gene to no longer be detectable by colony PCR (FIG. 10C indicates the locations of the different primer pairs). This result demonstrates the ease with which the cassette containing the Cre recombinase gene is removed from the rbcLXS locus in the absence of selective pressure.

Figure 11:
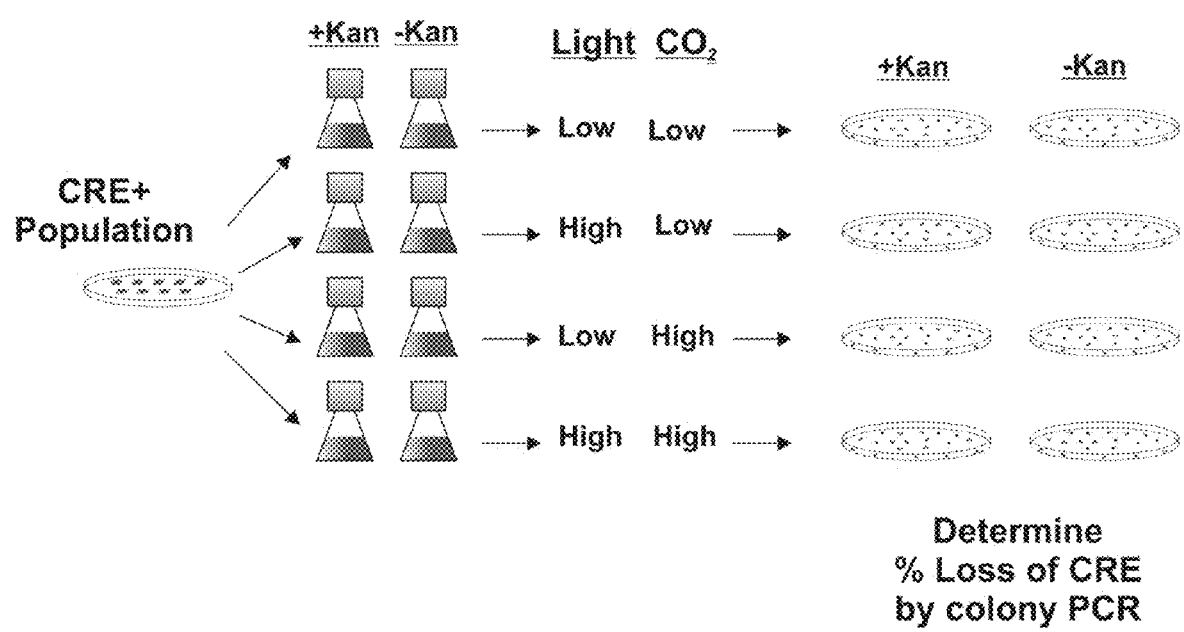
FIG. 11. Schematic describing conditions used to confirm removal of Cre recombinase from the rbcLXS locus. The ΔrbcLXS::$p_{rbcL}$Cre:kanR strain was patched on to a media A+ agar plate supplemented with kanamycin. Single patches were used to inoculate 50 ml media A+ in 250 ml shake flasks with or without kanamycin supplementation. Shake flasks were incubated under each of low light-low $CO_2$ conditions, high light-low $CO_2$ conditions, low light-high $CO_2$ conditions, and high light-high $CO_2$ conditions and grown to stationary phase before then being plated onto media A+ agar plates with or without kanamycin supplementation to isolate single colonies. Single colonies were analyzed by colony PCR to determine if the Cre gene were present or absent at the rbcLXS locus. Putative hits (i.e., those colonies that appeared to have lost the Cre gene by colony PCR analysis) were then plated again on media A+ agar plates with or without kanamycin supplementation to verify the loss of kanamycin resistance. Low light was 50 micromoles photons per square meter per second, high light was 250 micromoles photons per square meter per second. Low $CO_2$ was ambient $CO_2$ conditions. High $CO_2$ was ambient air supplemented with 1% $CO_2$. Kanamycin was supplied at 50 microgram/ml.
Figure 12:
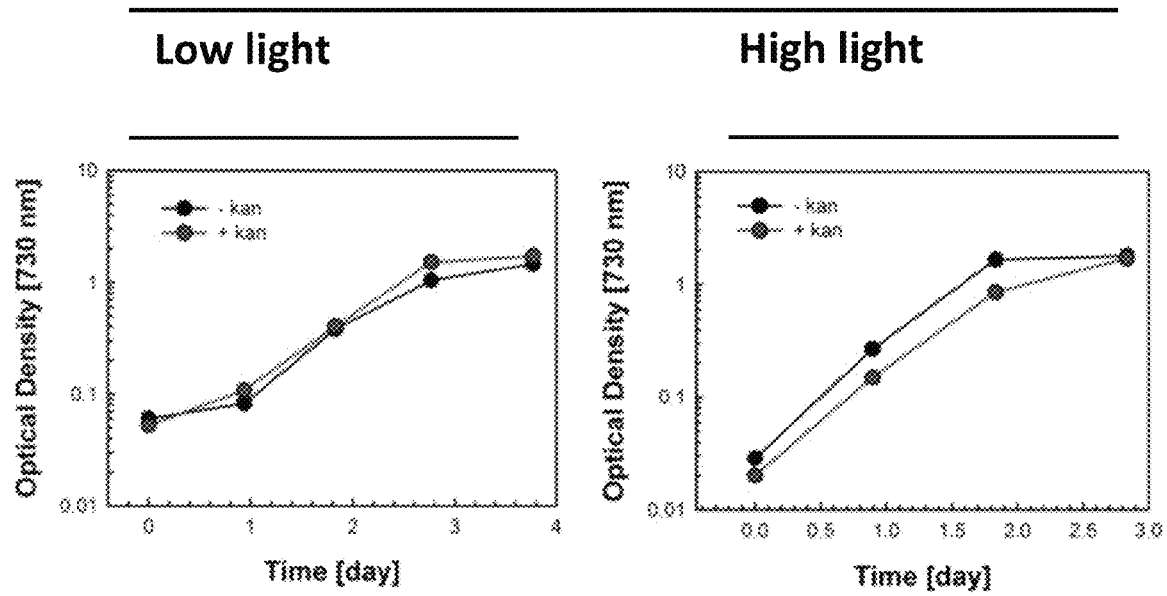
FIG. 12. Growth of cultures under the different conditions used to confirm removal of Cre recombinase from the rbcLXS locus. Growth of the ΔrbcLXS::$p_{rbcL}$Cre:kanR strain in media A+ with or without kanamycin under each of low light-low $CO_2$ conditions, high light-low $CO_2$ conditions, low light-high $CO_2$ conditions, and high light-high $CO_2$ conditions. Low light was 50 micromoles photons per square meter per second, high light was 250 micromoles photons per square meter per second. Low $CO_2$ was ambient $CO_2$ conditions. High $CO_2$ was ambient air supplemented with 1% $CO_2$. Kanamycin was supplied at 50 microgram/ml.
Figure 12:
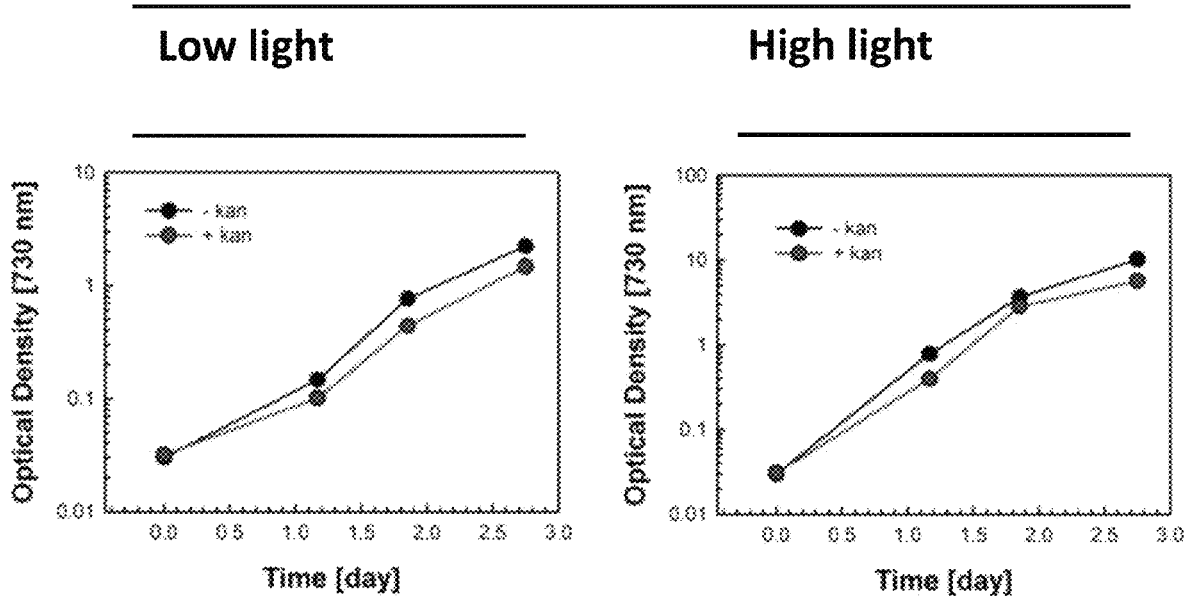
Figure 13:
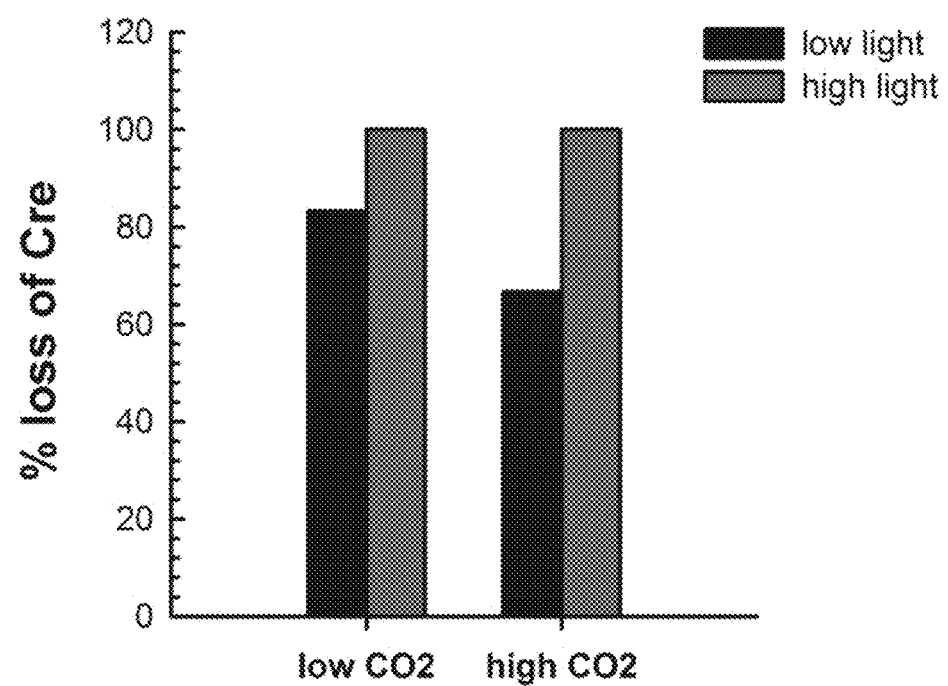
FIG. 13. Growth of cultures under the different conditions used to confirm removal of Cre recombinase from the rbcLXS locus. The percent loss of Cre was determined by colony PCR (n=6) on cell suspensions from indicated conditions in FIG. 11 and FIG. 12, using primers specific to both the rbcLXS (using the blue primer pair specific for rbcL, as shown in FIG. 10C; positive control) and Cre recombinase (using the blue and black primer pair specific for Cre, as shown in FIG. 10C).

It is known that availability of $CO_2$ and light effects the activity of RuBisCO as well as rbcLXS expression levels. To determine the effects of high and low light as well as high and low $CO_2$ on the loss of the cassette containing the Cre recombinase gene from the rbcLXS locus. Cells carrying the ΔrbcLXS::$p_{rbcL}$Cre::kanR mutation ('CRE+ Population') were second inoculated in media A+ liquid culture with or without kanamycin, as illustrated in FIG. 11. These liquid cultures were then incubated under each of low light-low $CO_2$ conditions, high light-low $CO_2$ conditions, low light-high $CO_2$ conditions, and high light-high $CO_2$ conditions. After reaching stationary phase, samples were plated on media A+ agar plates with or without kanamycin and grown under the same environmental conditions as the liquid cultures. Patches were then sampled for the loss of the Cre recombinase gene by colony PCR. Of note, as seen in FIG. 12, addition of kanamycin imparted little to no growth defects relative to those cultures that did not receive and antibiotics, further demonstrating that integration into rbcLXS does not significantly disrupt fitness. Testing 6 individual clones, colony PCR analysis demonstrated that the gene encoding Cre recombinase was lost from 100% of the cells grown under high light conditions, regardless of $CO_2$ availability (FIG. 13). However, under low light conditions, only 80% of cells lost the gene encoding Cre recombinase where grown under ambient $CO_2$ conditions and only 66% of cells lost the gene encoding Cre recombinase under high $CO_2$ conditions. These data indicate that the cassette containing the Cre recombinase gene is more readily removed from the rbcLXS locus where cells are grown in the absence of antibiotic selection and under high light conditions. This highlights the effectiveness of using essential genes as inherent or natural counter selection systems.

FIG. 14 summarizes the overall procedure used in this example.

Figure 15:
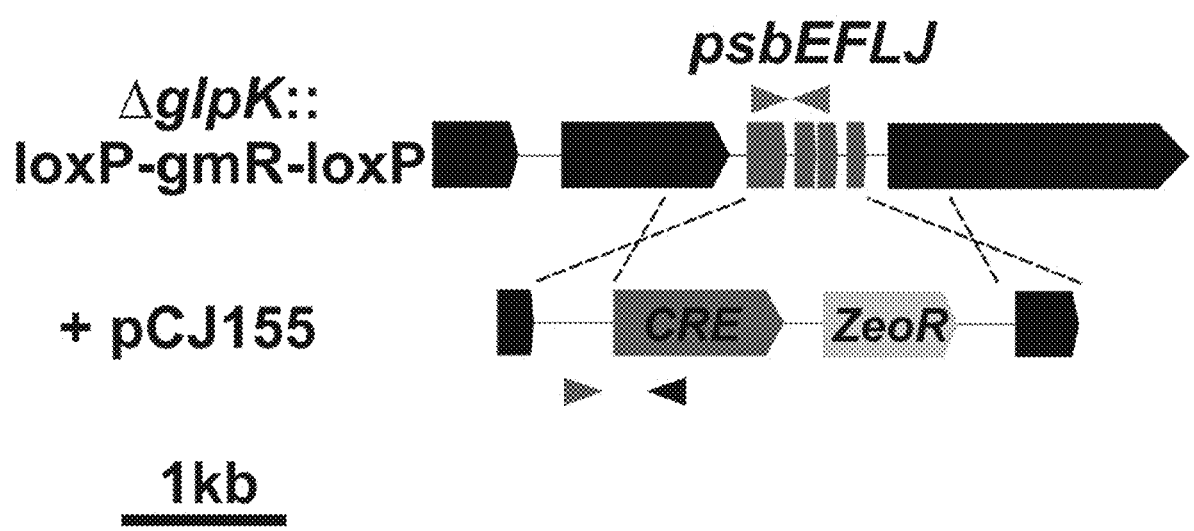
FIG. 15. Integration of Cre recombinase into the psbEFLJ locus using zeocin selection. Cre recombinase was integrated into the psbEFLJ locus using zeocin selection. ΔglpK::loxP–gmR–loxP represents a strain that has a loxP flanked gentamycin resistance cassette integrated into the glpK locus. pCJ155 represents the plasmid used to transform the ΔglpK::loxP–gmR–loxP strain and encodes Cre recombinase as well as a zeocin resistance cassette and integrates into the psbEFLJ locus in PCC 7002 via allelic exchange. The blue and black arrowheads represent PCR primers used to determine the presence or absence of the integration product. Purple arrowheads represent PCR primers used to determine the presence of the psbEFLJ locus.
Figure 16:
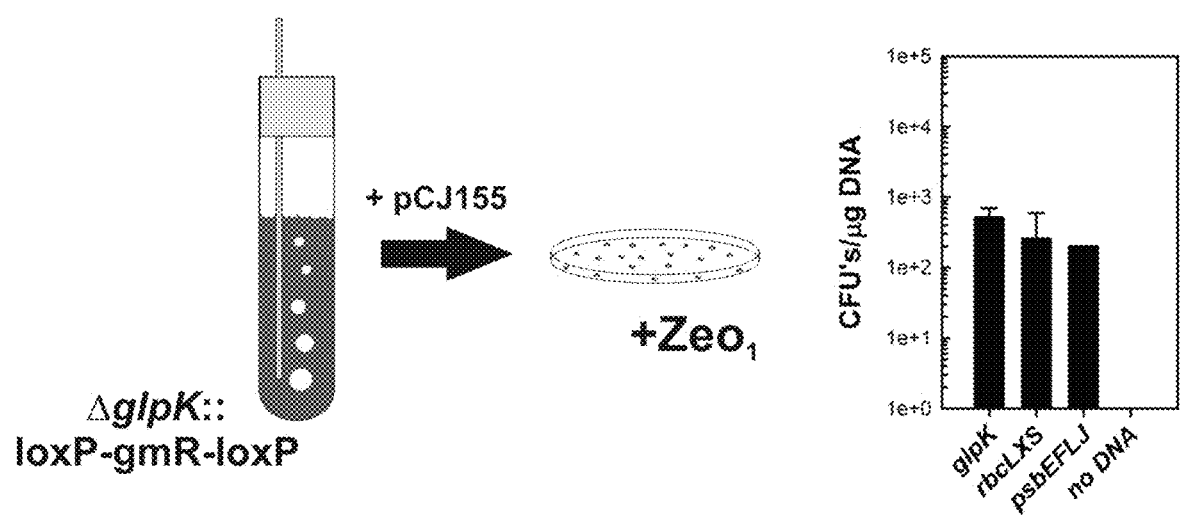
FIG. 16. Integrating of Cre recombinase into the psbEFLJ does not affect transformation efficiency. A schematic illustrating the transformation of a ΔglpK::loxP::gmR::loxP strain with pCJ155, a plasmid carrying a construct composed of the genes encoding Cre recombinase and zeocin resistance and that integrates into the psbEFLJ locus. The graph compares the transformation efficiencies obtained when integrating Cre recombinase into either the neutral site glpK, the essential rbcLXS locus, or the essential psbEFLJ locus. These data are not statistically significantly different from each other.

Example 2. Genome Engineering of Synechococcus sp. PCC 7002 Using the psbEFLJ Locus as a Natural Counter-Selection System To provide a first model essential gene target as a locus for transiently integrating and expressing a nucleic modification system, a new plasmid was prepared which would integrate into the essential psbEFLJ locus. This plasmid was generated using a translational fusion of the gene encoding Cre recombinase from Saccharomyces cerevisiae to the native rbcL promoter (as previously done in pCJ111), however, in this case a zeocin resistance gene was used and the homology arms for allelic exchange instead corresponded to the essential gene psbEFLJ. The plasmid contains the cassette needed to introduce the following mutation ΔpsbEFLJ::$p_{psbE}$Cre::zeoR and is referred to as pCJ155. Following homologous recombination of pCJ155 into the chromosomal psbEFLJ operon, this would result in the construction of a strain with the following additional mutation: ΔpsbEFLJ::$p_{psbE}$Cre::zeoR (FIG. 15). Cells in which a loxP-flanked gentamycin resistance cassette had already been integrated into the glpK locus, described as ΔglpK::loxP::gmR::loxP, were transformed with this construct and plated on media A+ agar plates containing 300 microgram/ml zeocin. Colony forming units were enumerated and the transformation efficiency was found not to be different from that of Example 1, where the genes encoding Cre recombinase and kanamycin resistance were instead integrated into the rbcLXS locus (FIG. 16). This result indicates that no discernable differences exist in terms of transformation efficiency or fitness when either rbcLXS or psbEFLJ are used as the essential gene locus for transient integration and expression of a nucleic acid modification system.

Figure 17:
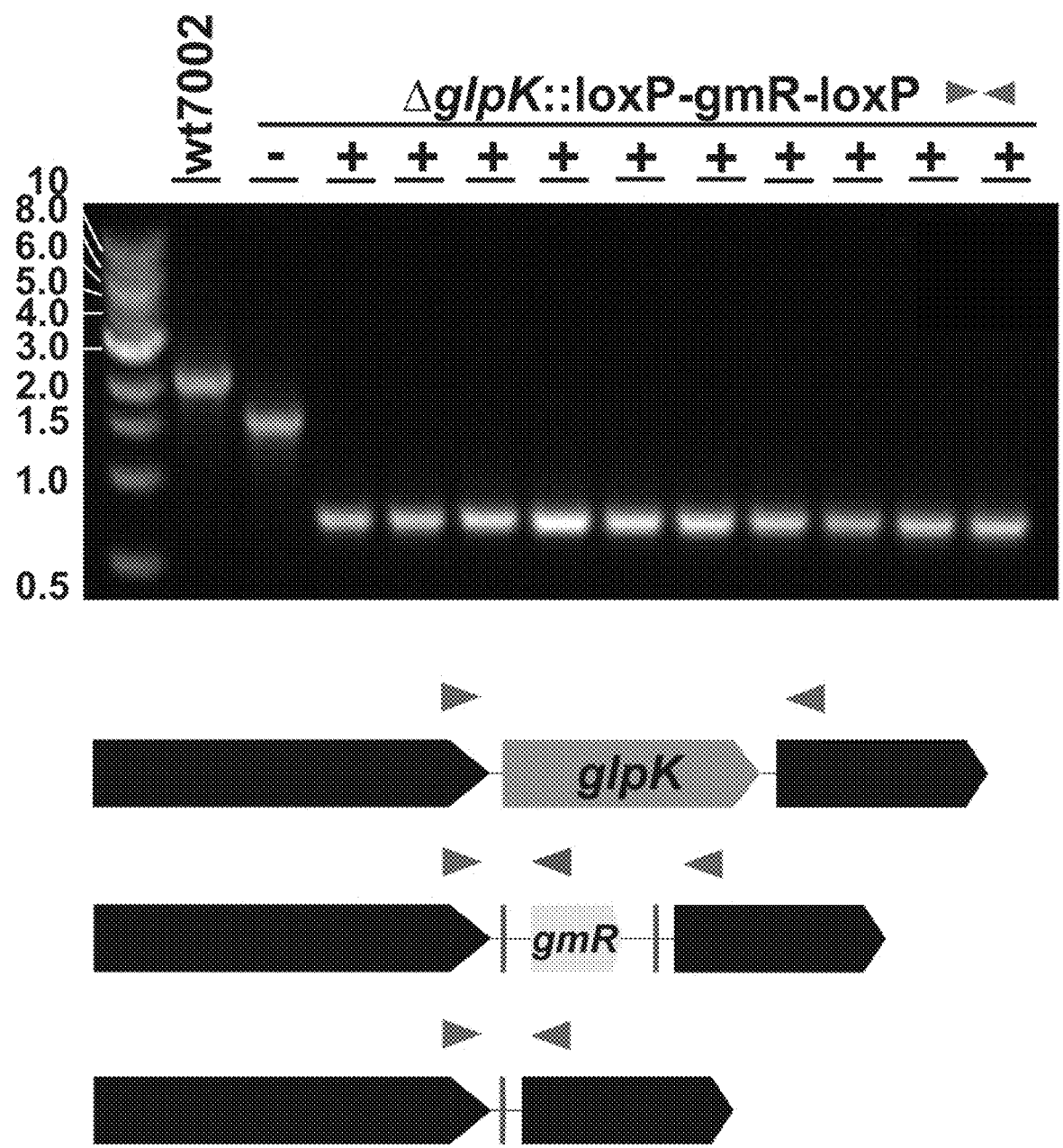
FIG. 17. Cre recombinase is 100% active in PCC 7002 when expressed from the psbEFLJ locus. The glpK locus of the ΔglpK:loxP–gmR–loxP strain is shown. wt7002 represents the wild type glpK locus. '–' represents the strain not transformed with pCJ155. '+' represents the strain that is transformed with pCJ155. Green and pink arrowheads represent PCR primers used to determine Cre activity. The gel demonstrates the colony PCR results from the indicated strains. wt7002 gives a band 2261 bp in size. ΔglpK::loxP–gmR–loxP–Cre or '–' gives a band 1656 bp in size. ΔglpK:loxP–gmR–loxP+Cre or '+' gives a band 761 bp in size.
Figure 18:
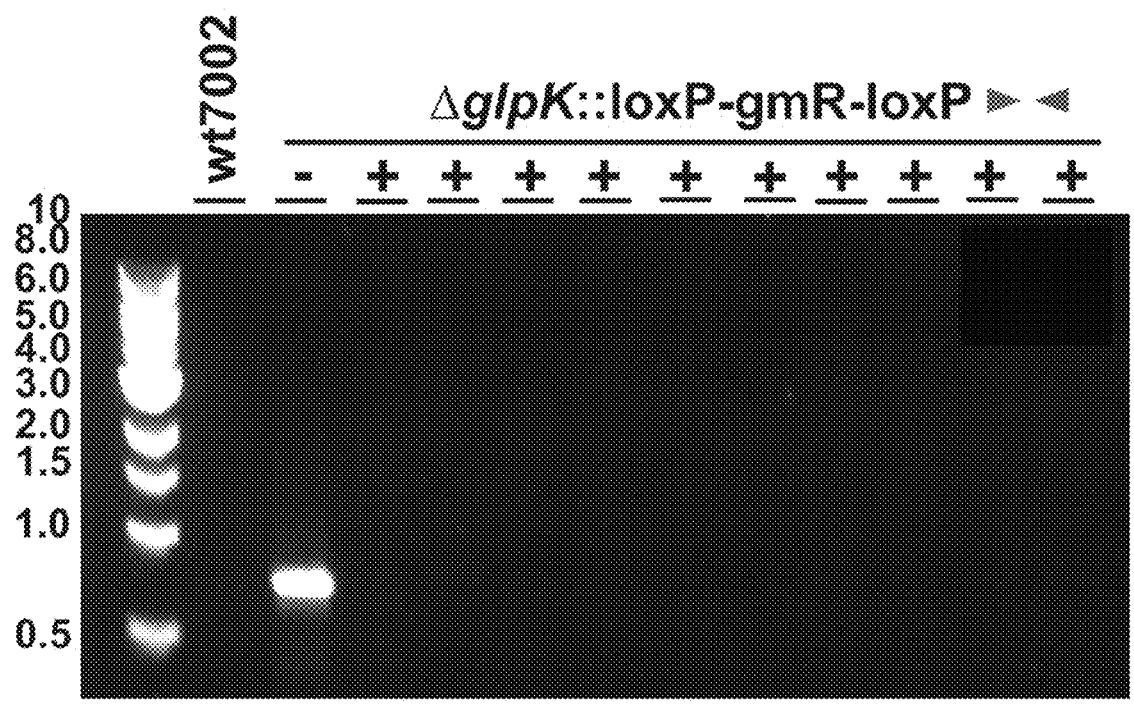
FIG. 18. PCR Validation of removal of the gentamycin resistance marker by Cre recombinase in PCC 7002. The glpK locus of the ΔglpK:loxP–gmR–loxP strain is shown. wt7002 represents the wild type gipK locus. '–' represents the strain not transformed with pCJ155. '+' represents the strain that is transformed with pCJ155. The green and pink arrowheads represent PCR primers used to determine loss of the gentamycin resistance marker. The gel demonstrates the colony PCR results from the indicated strains. wt7002 does not give a PCR product when tested with the indicated primer pair. ΔglpK::loxP–gmR–loxP–Cre or '–' gives a band 750 bp in size. ΔglpK::loxP–gmR–loxP+Cre or '+' does not give a PCR product when tested with the indicated primer pair.
Figure 18:
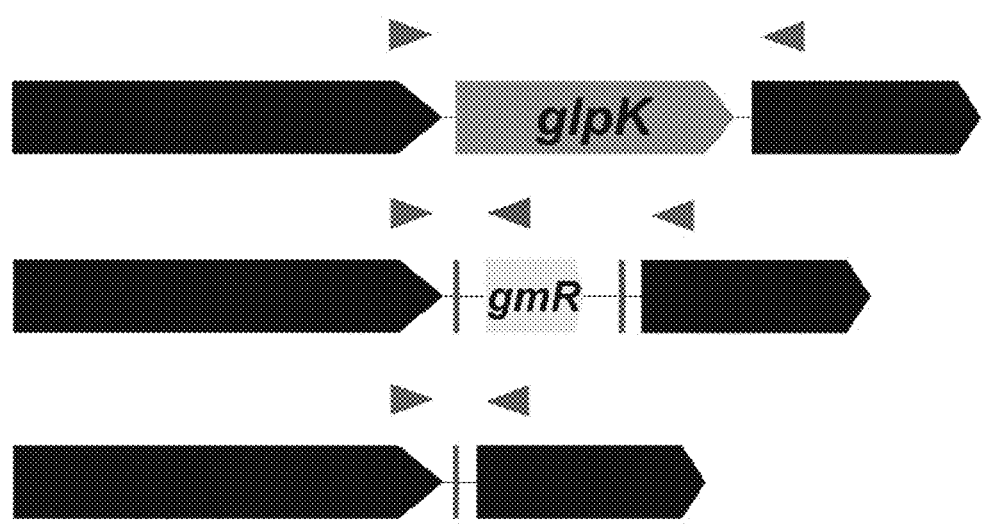

Following integration and expression of the genes encoding Cre recombinase and zeocin resistance from the psbE-FLJ locus, colony PCR was used to test for the loss of the gentamycin resistance gene which had been integrated into the glpK locus. Determination of whether or not Cre recombinase was active when it was expressed from the psbEFLJ locus was done by assaying the loss of the gentamycin resistance gene from the test strain by 2 independent methods. Second, colony PCR was performed on 10 individual transformants and with two different primer pairs. The second primer pair amplified a product outside the glpK gene 2261 bp in size. In the ΔglpK::loxP::gmR::loxP strain not transformed with pCJ155 this same primer pair produces a product 1656 bp in size. However in the ΔglpK::loxP::gmR::loxP strain transformed with pCJ111 the band is 761 bp in size. As seen in FIG. 17, all cells transformed with and carrying the Cre expression cassette within the psbEFLJ locus subsequently lost the gentamycin resistance gene that was integrated at the glpK site. This assay indicates that Cre recombinase expressed in this fashion displays high activity. A first primer pair amplifies a product only when the gentamycin cassette is present. As seen in FIG. 18 only the ΔglpK::loxP::gmR::loxP strain that was not transformed with pCJ155 produces a product using this primer pair.

Figure 19A:
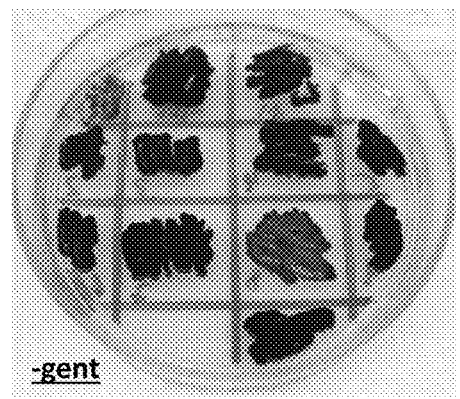
FIG. 19A. Phenotypic validation of the removal of the gentamycin resistance marker by Cre recombinase expressed from the psbEFLJ locus. Patches of either wt7002, ΔglpK::loxP–gmR–loxP–Cre, or 10 individual patches of ΔglpK::loxP–gmR–loxP+Cre were streaked onto agar plates containing no antibiotics.
Figure 19B:
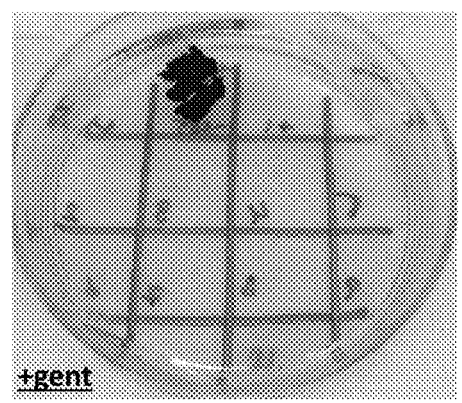
FIG. 19B. Phenotypic validation of the removal of the gentamycin resistance marker by Cre recombinase expressed from the psbEFLJ locus. Patches of either wt7002, ΔglpK::loxP–gmR–loxP–Cre, or 10 individual patches of ΔglpK::loxP–gmR–loxP+Cre were streaked onto agar plates containing 30 microgram/ml gentamycin.
Figure 19C:
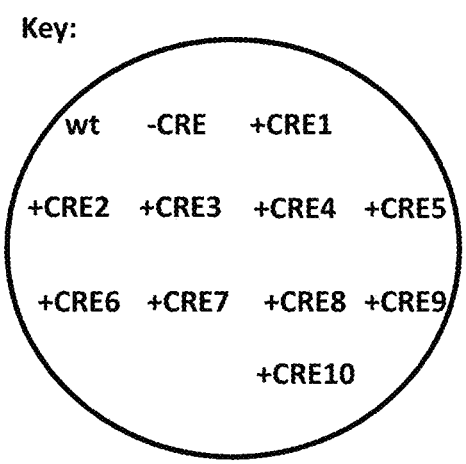
FIG. 19C. Phenotypic validation of the removal of the gentamycin resistance marker by Cre recombinase expressed from the psbEFLJ locus. Patching key for FIG. 19A and FIG. 19B.

Loss of the gentamycin resistance gene integrated in the glpK locus should also render cells sensitive to gentamycin. All 10 transformants were patched on media A+ agar plates containing either 0 microgram/ml gentamycin (FIG. 19A) or 30 microgram/ml gentamycin (FIG. 19B; see FIG. 19C for a guide). As can be seen, only the strain not transformed with pCJ155 was able to grow in the presence of gentamycin, while wt7002 as well as those transformed with pCJ155 could only grow in the absence of gentamycin. Taken together, these data suggest that the Cre recombinase is fully active in *Synechococcus* sp. PCC 7002 and that Cre-dependent recombination can be used to excise a selection marker flanked by LoxP occurs after expressing Cre from a nucleic acid construct integrated into a locus consisting of an essential gene. Furthermore, with a sample size of n=10, these results further demonstrate that Cre recombinase is active in PCC 7002 and enables efficient genome engineering of target sequences of interest.

Figure 20A:
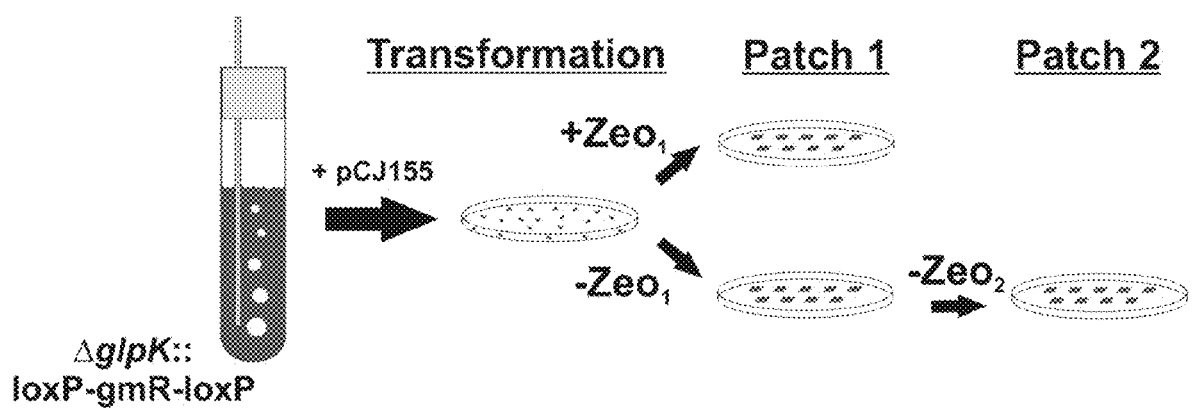
FIG. 20A. Determination of the loss of Cre from the psbEFLJ locus in the absence of zeocin selection. Patching workflow to determine the loss of Cre from the psbEFLJ locus in the absence of zeocin selection. The ΔglpK::loxP–gmR–loxP strain was transformed with the plasmid pCJ155, which encodes for Cre recombinase and a zeocin resistance cassette and integrates into the psbEFLJ locus by allelic exchange. From the initial transformation plate that contains 300 microgram/ml zeocin colonies are patched onto plates that either do not have any zeocin ($-Zeo_1$) or have 300 microgram/ml zeocin ($+Zeo_1$). Once the second patches grown in the absence of zeocin have reached maturity they are subsequently repatched onto a fresh agar plate that also does not contain zeocin ($-Zeo_2$). Patches are then sample by colony PCR.
Figure 20B:
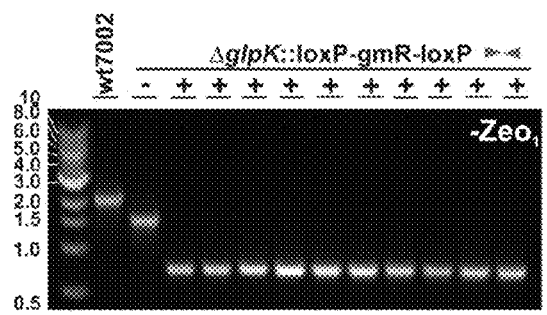
FIG. 20B. Determination of the loss of Cre from the psbEFLJ locus in the absence of zeocin selection. Colony PCR results from the patching experiment performed in the absence of zeocin selection. PCR primer pair colors are given in FIG. 15 and FIG. 17. A positive band indicates the presence of Cre at the psbEFLJ locus, the absence of a band indicates the absence of Cre at the psbEFLJ locus. 'n/a', Not applicable.
Figure 20B:
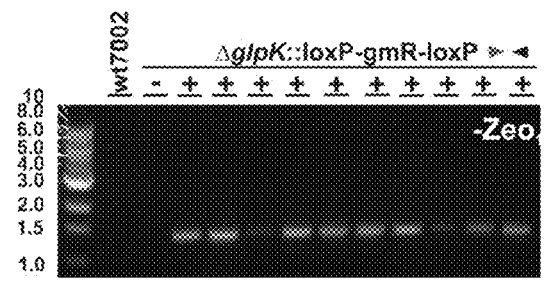
Figure 20B:
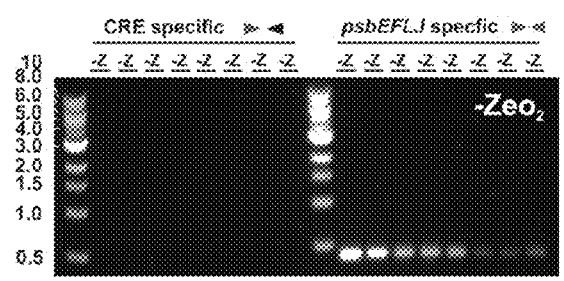

To then remove the integrated DNA cassette containing the genes encoding Cre recombinase and zeocin resistance from the psbEFLJ locus, cells still carrying the genes encoding Cre recombinase and zeocin resistance were cultured in liquid media A+ without zeocin at 300 micromole photons per square meter per first irradiation under air supplemented with 1% $CO_2$. Cells carrying the genes encoding Cre recombinase and zeocin resistance were cultured in plated on media A+ agar plates containing 300 microgram/ml zeocin (FIG. 20A). Colonies were patched onto on media A+ agar plates containing either 0 or 300 microgram/ml zeocin. Cells were re-patched in this manner until the full loss of the genes encoding Cre recombinase and zeocin resistance was achieved. As seen in FIG. 20B, initial patches grown on media A+ agar plates in the absence of zeocin still carried the gene encoding Cre recombinase at the psbEFLJ locus, albeit at reduced levels compared to those cells that were patched on media A+ agar plates containing zeocin. However, by the first patching, all cells initially carrying the genes encoding Cre recombinase and zeocin resistance had lost Cre recombinase from the psbEFLJ locus. These experiments further demonstrate that cells carrying unsegregated copies of a nucleic acid modification system (such as Cre) at other essential gene loci (such as psbEFLJ) will revert back to the wildtype genotype when the antibiotic selection is removed.

SEQUENCES

| SEQ ID NO: | Sequence | Description |
|---|---|---|
| 1 | gtgaatatttcaccccccattcaacttgtcgaag ccccacccaagctttactgacctgggctaaggc gatcgccacgggcaccccagacccatttcagcgg gggcaacaactgagtcagaaattgggcgcaacct atggcagtgatggcctaacccaaataggattctg gattccggaggtgggcgatcgccccgtttacctc gaaattttacgcccatggaggcaatcgattttc gccttgctgatcaagtcattccgttccgtcggga ggtgctagaactgccgcgccaggggggaatttgcc tgggccgttgtggcgggtctcaaagctggcaccc gtacccaagcgggatcgttttactggttgcgcag tggtgaacagattatccgcgatgtctttgcccac tctctgccctacggtgtgtttgcgccagccgagc tgtacgacatggcgcaactggagcgcgacagggc cgaccgcgactattttcaccaggaaacttgggtc acaccgccccgcaatattttgcagattcatgtgg gtaccgcttcccccacgggcaccctagccggact cagccgcatttaccgtgacctcgcccgcaaattg gccaatagccaacccctcaccgccgctgaaaaaa actatgtgggctttgatgcgattgaactgttacc cattgaacccacggtggaatttcgccccgccgaa aatgaaatgattcatgcttttggcaaattcggg cgatcaccaaccaagaagtgcaagtccacctgaa aaaaccagacacccaaaattggggctatgacgat ctgattttagggcgcgcggccaccagtcccgccc tcctcagtaccctcagacccaccgaagttgtgga ttttattgccacgctccacactgcctttgcccgc ccgatccagattatttttgacctggtttatgggc atatccatcaccaagccctgggattaatcaatgc gcgattttccggggcgcaaatatgtatggccat gatacaaaccagcaaaatccgatggtgcgggctg ttctcctggagttgcaacggcgaaaaattaatct aggggccgatgggattcgggtggatgggggtcaa gattttcaggtgtccgacgccatttccggccaac tagactatgacaatgatttcctgctgaagatggc tgcggtacccaaaccgttggtacagcgactcgc gagttgtacaccatttatgaagatgccgcccct ggcccaatgtcggttgggaagatatggctaccca tttggatttaatttacctaaagcccgattgtttt | glpK locus wt 7002, visible region (FIG. 3A) |

| SEQ ID NO: | Sequence | Description |
|---|---|---|
| | cagtggagtccgttgatcttcgagcataatacgc | |
| | ccacgttacagggattttggcaacgggaatggcg | |
| | ggatgtgtgcaaaattatggcccatggcgatcgc | |
| | tgggtgaccggttgcgccaaccatgacacggtac | |
| | gcaagggcaaccacatcaacaccgccgcaattcg | |
| | gattaatgaatatttaggggattctttgccggaa | |
| | attttacaaaatgcctacgataatccagcaaccc | |
| | aactgtggatccatggctttagcccaggaattcc | |
| | gatggatttttaaatgcattaatgcacactccc | |
| | tggggctttttcggaatacagatgaccaatatg | |
| | ccgtcaaaattatggcggacgaaattggctttct | |
| | ctattggcaaattacgccggaaatttaccgacaa | |
| | tcctgggcgtttcggcggtttaaaaccatgggct | |
| | tttatgatctctcgttaatgcggcagttctttaa | |
| | ggcagtgaacaggccattgaagcgattggctat | |
| | gatctaccaaagctggcgattttctgcaaaccg | |
| | aattagaaccacaatttgattttttaaagccgat | |
| | taccattgccaacctgaaggaaatagcgatcgcc | |
| | tttatggaggatggccacgaggcttgtcgggtct | |
| | cccattattgtggatcggtaccggatgagcgggc | |
| | gagctttaatttacgcttgcggcaatatcgccag | |
| | gcccagccttggctgcgaaatcatctcgatcctg | |
| | caaggggcgatcgcctgcaccattggtcggatca | |
| | ccaacgcaccattttctacggcaggcgcaccaat | |
| | cccgacacccagcagcggcttgtgttagtggcgc | |
| | acatggccggggctccgaagaccgttgagattgg | |
| | caaatggctcgccctggatttggatcgttggcag | |
| | ttggcgatcgccacaccgactttgaagatcaaca | |
| | ccatctatgacttagcccaaattcacttgcacaa | |
| | tggcgaaggttttctgttatctgaaattcctccc | |
| | taaatgatgtcttttgagcctaaaaacacacttt | |
| | tttgacctaatttaacccatttaaaaaactttat | |
| | ttaataatgaccatggcccatcaaaaatacattc | |
| | ttgcgttagacctcggtaccactggtaatcgtgc | |
| | ccttttgtttaaccacaaaggcgatattgttgcc | |
| | caagcctataaagaattaacccaatattatcccc | |
| | agccgggctgggtcgaacatgatgcgacggaaat | |
| | ttggaacgacaccaaagccgtcatgcaacaggtc | |
| | gtcaacaatagcagcattgaaacccaggatatcg | |
| | cggcgatcggcctgacggtgcagcgggaaacctg | |
| | tgtcctctgggataaaaccactggcaaaccactt | |
| | cataaagcaattgtctggcaggatcggcggacgg | |
| | ctcccctctgtcaaaccctcagtgcggcaggcaa | |
| | agcggcagaaatttacgataaaacgggcttggtg | |
| | ttggatgcttattttcggcgacgaaactgaatt | |
| | ggttattaagctgggctaaggaaaatagtgccat | |
| | taaccccaataatgtcctcgctggaaccattgac | |
| | acctgggccttgtggaacctcacgggaggcaaag | |
| | tccacgccacagatcacagtaatgccagccggac | |
| | aatgttgctcaatctcaaccaaaaagattgggat | |
| | ccggatttgttggatttattcgatattccccgcc | |
| | agatgatgccaacggtgcagtcgagcctagggga | |
| | atttggcaaaaccgatccaagtttattggggcg | |
| | gcaattccgatcaccgccatctttggggatcaac | |
| | aggcggccctctatgcccatggttgcgatcgcc | |
| | cggcttattaaaatgcacctatggcacaggggcg | |
| | ttttggtggcgcacacgggcgacgagattaaac | |
| | gctccaaacataagctcctaacgaccatcgcgca | |
| | accattggatacaagcccatcacgatggcacaaa | |
| | tctcgatattggctatgccctcgaagggagtatg | |
| | ttcaccgctggggcttgtatccaatggttgcgcg | |
| | atggcctacaaattatcgaaacggcggcggaaac | |
| | gaatgatcttgcccaaggggtgaatgataatggc | |
| | ggcgcttattttgttccggctttaagtggtctgg | |
| | gagcgccccactgggatatgagtgccaggggcgc | |
| | atttctgggtttaacgagaggcgtcaaaaaagaa | |
| | cacatggtacgggctgtcctagaggcgatcgcct | |
| | accaagccaaagaagtagtcgaagcgattaacca | |
| | agattccggtacgccgatccaagaattaaaagtc | |
| | gatggcggcgcgtgcaataacgactttctgatgc | |
| | aattccaagctgacgtgttgggtattcccgtgga | |
| | acgtcccgctgtcctcgatgccacggcccagggg | |
| | gcagccttgccgctggattagctgtcggttttt | |
| | gggatgattaccaaaccctggtgcaaaaccgcaa | |
| | aattgattacgtctttaagcccagtgccaacgcc | |

| SEQ ID NO: | Sequence | Description |
|---|---|---|
| | tcccaagcccaagcccatttcaaagtctggcaaa<br>aagccgttgaacgagcgaaaaactgggcctaacc<br>ccctcttgcctacagcatctcccccaggggagaa<br>ttcttcctgtttcaactccctctaacgtaaaccc<br>attgaatttaaaaaagactttatgactgctttac<br>tgctccatgaccaacattattcccttgatcatga<br>agcctttctctcaaccctcagcaacacagaaaat<br>ttactcattattcaagatctagatggcgtttgca<br>tggggttagtcaaagaccccttaacccgcaaaat<br>tgatcctgactatatccgcgccacacgcaagttt<br>agagaccacttctttgtcctcaccaacggtgaac<br>atgaaggcagaaggggagtaaatcgcatcgttga<br>acgggcatttcgcaatgttgaagccaaagaggaa<br>acaagctatttacctggtttagcagcaggggtg<br>tgcaatggcagacagataatggccaaatttccca<br>tcccggtgttagccaagcagaactcgatttcctt<br>gccacagtgccagatttaattggtcaaagtttag<br>gacaattttttactaaatatgttgatatttttcc<br>cgctgagcttcaacctgagctgatccatgcttct<br>gttttagataatctcgtttcaccgacggcaaatt<br>taaacgtcctggccgaatatttaggcgatcgcct<br>tgagatttaccaagacctccagcgcaccatggaa<br>accctgatgaatgatttgctagaaaaagctggcc<br>aacagggtttagacaatagttttttcgtgcacta<br>tgcgcccaatttaggcagagataatgtggggaaa<br>gaaattgtccgctttgccacagccaaggattctg<br>gcaccacagattttcagtttatggtgtgtggtgc<br>cgtcaaagaagcgggggttttagtgctgctgaat<br>tattactatgcccaacgcacgggccactatcccc<br>taggagaaaccttaacgcccgccaagcgcccca<br>aaaccacgaggaactattgcaactggtgcaagac<br>aatttcgatccgcaattgatgcctttaatcgttg<br>gcgtcggcgatacggtcacaagtcacaccgaagg<br>cgatcaagttcgacgggggggagcgatcgccta<br>ttcctgcagctcgtccaagacattggtaaatggg<br>caaagagcggcaatctcgtcgtgtatatcgacag<br>ctcccagggagaattaaaaaatcggattccctta<br>aaactggggacaatcaatggtcaaacccaagtga<br>ttgagggcattactgatccggctgatccgttaca<br>aattaacgttgcttttccgggcgggtttgaacaa<br>tacaccgccctttttcagcaggccgccgcaaacc<br>gatctggaacatag | |
| 2 | catctcgatcctgcaaggg | White arrow primer pair:<br>FWD. (FIG. 3A) |
| 3 | aaccaattcagtttcgtcgc | White arrow primer pair:<br>REV. (FIG. 3A) |
| 4 | gtgaatatttcaccccccattcaacttgtcgaag<br>cccccacccaagctttactgacctgggctaaggc<br>gatcgccacgggcacccagacccatttcagcgg<br>gggcaacaactgagtcagaaattgggcgcaacct<br>atggcagtgatggcctaacccaaataggattctg<br>gattccggaggtgggcgatcgccccgtttacctc<br>gaaattttacgcccatggaggcaatcgatttc<br>gccttgctgatcaagtcattccgttccgtcggga<br>ggtgctagaactgccgcgccaggggaatttgcc<br>tgggccgttgtggcgggtctcaaagctggcaccc<br>gtacccaagcgggatcgttttactggttgcgcag<br>tggtgaacagattatccgcgatgtctttgcccac<br>tctctgccctacggtgtgtttgcgccagccgagc<br>tgtacgacatggcgcaactggagcgcgacagggc<br>cgaccgcgactattttcaccaggaaacttgggtc<br>acaccgccccgcaatattttgcagattcatgtgg<br>gtaccgcttcccccacgggcaccctagccggact<br>cagccgcatttaccgtgacctcgcccgcaaattg<br>gccaatagccaacccctcaccgccgctgaaaaaa<br>actatgtgggctttgatgcgattgaactgttacc<br>cattgaaccacggtggaatttcgccccgccgaa<br>aatgaaatgattcatgcttttttggcaaattcggg<br>cgatcaccaaccaagaagtgcaagtccacctgaa<br>aaaaccagacacccaaaattggggctatgacgat<br>ctgattttaggggccgcggccaccagtcccgccc<br>tcctcagtaccctcagacccaccgaagttgtgga | ΔglpK::loxP-gmR-loxP,<br>visible region (FIG. 3B) |

| SEQ ID NO: | Sequence | Description |
|---|---|---|
| | tttattgccacgctccacactgcctttgcccgc | |
| | ccgatccagattattttgacctggtttatgggc | |
| | atatccatcaccaagccctgggattaatcaatgc | |
| | gcgattttccggggcgcaaatatgtatggccat | |
| | gatacaaaccagcaaaatccgatggtgcgggctg | |
| | ttctcctggagttgcaacggcgaaaaattaatct | |
| | aggggccgatgggattcgggtggatgggggtcaa | |
| | gattttcaggtgtccgacgccatttccggccaac | |
| | tagactatgacaatgatttcctgctgaagatggc | |
| | tgcggtaccccaaaccgttggtacagcgactcgc | |
| | gagttgtacaccatttatgaagatggccgcccct | |
| | ggcccaatgtcggttgggaagatatggctaccca | |
| | tttggatttaatttacctaaagcccgattgtttt | |
| | cagtggagtccgttgatcttcgagcataatacgc | |
| | ccacgttacagggattttggcaacgggaatggcg | |
| | ggatgtgtgcaaaattatggcccatggcgatcgc | |
| | tgggtgaccggttgcgccaaccatgacacggtac | |
| | gcaagggcaaccacatcaacaccgccgcaattcg | |
| | gattaatgaatatttaggggattctttgccggaa | |
| | attttacaaaatgcctacgataatccagcaaccc | |
| | aactgtggatccatggctttagcccaggaattcc | |
| | gatggattttttaaatgcattaatgcacactccc | |
| | tggggcttttttcggaatacagatgaccaatatg | |
| | ccgtcaaaattatggcggacgaaattggctttct | |
| | ctattggcaaattacgccggaaatttaccgacaa | |
| | tcctgggcgtttcggcggtttaaaaccatgggct | |
| | tttatgatctctcgttaatgcggcagttctttaa | |
| | ggcagtggaacaggccattgaagcgattggctat | |
| | gatctaccaaagctggcgattttctgcaaaccg | |
| | aattagaaccacaatttgatttttaaagccgat | |
| | taccattgccaacctgaaggaaatagcgatcgcc | |
| | tttatggaggatggccacgaggcttgtcgggtct | |
| | cccattattgtggatcggtaccggatgagcgggc | |
| | gagctttaatttacgcttgcggcaatatcgccag | |
| | gcccagccttggctgcgaaatcatctcgatcctg | |
| | caaggggcgatcgcctgcaccattggtcggatca | |
| | ccaacgcaccattttctacggcaggcgcaccaat | |
| | cccgacacccagcagcggcttgtgttagtggcgc | |
| | acatggccggggctccgaagaccgttgagattgg | |
| | caaatggctcgccctggatttggatcgttggcag | |
| | ttggcgatcgccacaccgactttgaagatcaaca | |
| | ccatctatgacttagcccaaattcacttgcacaa | |
| | tggcgaaggttttctgttatctgaaattcctccc | |
| | taaatgatgtcttttgagcctaaaaacacactt | |
| | tttgacctaattaacccataacttcgtataATG | |
| | TATGCtatacgaagttatCCTAGGCTGCAGCGGC | |
| | CGCTACTAGTACAACAAAGCCACGTTGTGTCTCA | |
| | AAATCTCTGATGTTACATTGCACAAGATAAAAT | |
| | ATATCATCATGAACAATAAAACTGTCTGCTTACA | |
| | TAAACAGTAATACAAGGGGTGTTatgttacgcag | |
| | cagcaacgatgttacgcagcagggcagtcgccct | |
| | aaaacaaagttaggtggctcaagtatgggcatca | |
| | ttcgcacatgtaggctcggccctgaccaagtcaa | |
| | atccatgcgggctgctcttgatcttttcggtcgt | |
| | gagttcggagacgtagccacctactcccaacatc | |
| | agccggactccgattacctcgggaacttgctccg | |
| | tagtaagacattcatcgcgcttgctgccttcgac | |
| | caagaagcggttgttggcgctctcgcggcttacg | |
| | ttctgcccaggtttgagcagccgcgtagtgagat | |
| | ctatatctatgatctcgcagtctccggcgagcac | |
| | cggaggcagggcattgccaccgcgctcatcaatc | |
| | tcctcaagcatgaggccaacgcgcttggtgctta | |
| | tgtgatctacgtgcaagcagattacggtgacgat | |
| | cccgcagtggctctctatacaaagttgggcatac | |
| | gggaagaagtgatgcactttgatatcgacccaag | |
| | taccgccacctaaTCAGAATTGGTTAATTGGTTG | |
| | TAACACTGGCAGAGCCTCTAGTATATAAACGCAG | |
| | AAAGGCCCACCCGAAGGTGAGCCAGTGTGACTCT | |
| | AGTAGAGAGCGTTCACCGACAAACAACAGATAAA | |
| | ACGAAAGGCCCAGTCTTTCGACTGAGCCTTTCGT | |
| | TTTATTTGATGCCTGGCTCTAGTCTCGAGataac | |
| | ttcgtataATGTATGCtatacgaagttatccccc | |
| | tcttgcctacagcatctcccccaggggagaattc | |
| | ttcctgtttcaactccctctaacgtaaacccatt | |
| | gaatttaaaaaagactttatgactgctttactgc | |

-continued

| SEQ ID NO: | Sequence | Description |
|---|---|---|
| | tccatgaccaacattattcccttgatcatgaagc<br>ctttctctcaaccctcagcaacacagaaaattta<br>ctcattattcaagatctagatggcgtttgcatgg<br>ggttagtcaaagacccccttaacccgcaaaattga<br>tcctgactatatccgcgccacacgcaagtttaga<br>gaccacttctttgtcctcaccaacggtgaacatg<br>aaggcagaaggggagtaaatcgcatcgttgaacg<br>ggcatttcgcaatgttgaagccaaagaggaaaca<br>agctatttacctggtttagcagcaggggtgtgc<br>aatggcagacagataatggccaaatttcccatcc<br>cggtgttagccaagcagaactcgatttccttgcc<br>acagtgccagatttaattggtcaaagtttaggac<br>aattttttactaaatatgttgatattttcccgc<br>tgagcttcaacctgagctgatccatgcttctgtt<br>ttagataatctcgtttcaccgacggcaaatttaa<br>acgtcctggccgaatatttaggcgatcgccttga<br>gatttaccaagacctccagcgcaccatggaaacc<br>ctgatgaatgatttgctagaaaaagctggccaac<br>agggtttagacaatagttttttcgtgcactatgc<br>gcccaatttaggcagagataatgtggggaaagaa<br>attgtccgctttgccacagccaaggattctggca<br>ccacagattttcagtttatggtgtgtggtgccgt<br>caaagaagcgggggttttagtgctgctgaattat<br>tactatgcccaacgcacgggccactatcccctag<br>gagaaacctttaacgcccgccaagcgccccaaaa<br>ccacgaggaactattgcaactggtgcaagacaat<br>ttcgatccgcaattgatgcctttaatcgttggcg<br>tcggcgatacggtcacaagtcacaccgaaggcga<br>tcaagttcgacgggggggagcgatcgcctattc<br>ctgcagctcgtccaagacattggtaaatgggcaa<br>agagcggcaatctcgtcgtgtatatcgacagctc<br>ccaggagaattaaaaaatcggattcccttaaaa<br>ctggggacaatcaatggtcaaacccaagtgattg<br>agggcattactgatccggctgatccgttacaaat<br>taacgttgcttttccgggcgggtttgaacaatac<br>accgccctttttcagcaggccgccgcaaaccgat<br>ctggaacatag | |
| 5 | catctcgatcctgcaaggg | Black arrow primer pair:<br>FWD. (FIG. 3B) |
| 6 | caagcgcgatgaatgtctta | Black arrow primer pair:<br>REV. (FIG. 3B) |
| 7 | catctcgatcctgcaaggg | Green/magenta primer<br>pair (FIG. 8): FWD |
| 8 | caagcgcgatgaatgtctta | Green/magenta primer<br>pair (FIG. 8): REV |
| 9 | aacacgccagcactcgccgttttaaaacccagtc<br>ttggctaggggcaggctttgtggagggtcattct<br>gctaatcagattttggcaaatatccaggcgatcg<br>ccgcccagttccccaacgaatatgtccagttaat<br>cgccgttgacccccaactccaaaacacgggccgca<br>gagatcatcatccaacgccctggcaacaatgcgc<br>ctgtccagacagcaaccgcaaccagtagtttttc<br>gggaggcacgaaagcagccccaagcagcaatggt<br>ttcgggggtcacagtagcgggagtctcagtgggg<br>atgtggtttctaaagtccgttcgcttttgatgca<br>aggctacaagattggaacagaacacgccgataag<br>cgccgtttccgtgttaagtcctggagtagttgtg<br>gcaccattgacagcacccaagaggcagaagtttt<br>acgtcacctcgaaggttgtctccaggagcacagt<br>ggcgaatatgtccgcatgattggtgtcgatgaag<br>cggctaaacgacgggtgcttgaggaaattatcca<br>acgcccctaggttgtgtaacgcgaccacttcgtt<br>atggggagaaaacgaatgtctatcccccaaccc<br>ttaccccacctgtgattaattgaatcaccgttga<br>cagaatcattgtgacttttccaggcaattacccat<br>ccagatattcaaattagtggcgatgtaaggattc<br>atccccgtgcggttattgccccggtgttattct<br>gcaagcaaccgaaggcaattatgtggcgatcgcc<br>actggtgcttgtattggtgcaggtgcgattatcc<br>aggcccacggcggcaacatcgagatccatgccgg | rbcLXS locus, wt 7002,<br>visible region FIG. 4A |

-continued

| SEQ ID NO: | Sequence | Description |
|---|---|---|
| | cgcgattatcggggcaggctgcctgatcattggc | |
| | caatgctcagtgggagaaaatgcctgcttaggtt | |
| | atggctctaccctatttcaagcggcgatcgccgc | |
| | cgccgcaattctcccgcccaaagcctcatcggc | |
| | gatccgtcccgccaagaaaccaccgcttcttacc | |
| | agactcaaccgccaaaacccgcgaatcaatcgac | |
| | aacccaacccctcgatccttggcaggcagaagat | |
| | acaactaaccagactgccacaaccttttcgccac | |
| | cagggcgatcgcccactagcagcagcaatcgtcc | |
| | caatgtccagccccaccagaagcaggatcccct | |
| | ccaactgaaacaccaaacaccgaagtgatgccga | |
| | cggttccagaatcaaaggaatccctagaatcggg | |
| | cgaaaaacaccagttgtcgggcaagtttatatc | |
| | aatcaactattaatgaccctattccctcaccaaa | |
| | attctctcaatacccaaatcaaccagatgagcc | |
| | ttagccccacaaaactttcatgattgcttgagtg | |
| | aaaattaaatgtttaaagttcttaaaggagattg | |
| | ttgagaaacataaatacttaattcatctcatttg | |
| | aacgctttccctctctaaagatcccgacagaaaa | |
| | cggttttagcccaatgtctcattaggtagcatgg | |
| | ctgaattcgagcgggattttatggcttttttagg | |
| | tattttttgtaagggtaaaataggcccatcaaaca | |
| | gcattagaaatgctaatcagcccaaaaaacaaaa | |
| | gcaatcttttttttgttgctaaaagataaaaataa | |
| | gtcgaggctgtggtaacatatcccacagattaaa | |
| | gaaagtcataagacttgaatcttcagaattttaa | |
| | aaagcagttttgccaacgtaagattttttgaagtt | |
| | ttcgaccaacaataccgttactggtatttgtctg | |
| | ttaaagataagcattttttgctggaggaaaaccgc | |
| | atggttcagaccaaatctgctgggtttaatgccg | |
| | gtgtacaggactaccgcctgacttactacaccc | |
| | cgattacaccccgaaagataccgacttactcgct | |
| | tgtttccggatgactccccaacctggagtccccc | |
| | ccgaagaatgtgctgcggctgttgcggctgaatc | |
| | ttctaccggtacttggaccactgtatggaccgat | |
| | ggtttaactgacctcgaccgctacaagggtcgtt | |
| | gctacaatgttgaacccgttcccggtgaagacaa | |
| | ccaatatttctgtttcgttgcttacccctcgat | |
| | ctgtttgaagaaggttctgtaaccaacgttttga | |
| | cttccttggttggtaacgtattcggttttaaagc | |
| | gctgcgtgccctgcgcctcgaagatatccgcttc | |
| | cccgttgcgttaatcaaaacttaccaagggcctc | |
| | cccacgggatcactgtagagcgtgacctcctcaa | |
| | caagtatggtcgtcctctcctcggttgtacgatt | |
| | aagccgaagctcggtctgtctgcgaagaactacg | |
| | gtcgtgcggtttatgaatgtctccgtggtggtct | |
| | tgacttcaccaaagatgacgaaaacatcaactct | |
| | cagcctttcatgcgttggcgcgatcgcttcctgt | |
| | tcgttcaagaagctatcgaaaaatcccaagctga | |
| | aaccaacgaagttaagggtcactaccttaacgtc | |
| | accgctggcactttgcgaagaaatgctcaagcggg | |
| | ctgaattcgctaaggaaatcggcactcccatcat | |
| | catgcacgacttcttaactggtggtttcactgcg | |
| | aatactacccttgcgaagtggtgtcgtgataacg | |
| | gcgttctgctccacatccaccgggcaatgcacgc | |
| | ggtaatcgaccgtcagaagaaccacgtgtattcac | |
| | ttccgcgttctcgctaagtgtctccgcctctctg | |
| | gtggtgaccacctccactccggtacggttgttgg | |
| | taagctcgaaggcgatcgcgccgccaccctcggt | |
| | ttcgtagacctgatgcgtgaagactacgttgaag | |
| | aagatcgttctcgcggtgtattcttcacccaaga | |
| | ctacgcttctctcccggcaccatgcctgtggct | |
| | tccggtggtatccacgtatggcacatgcctgccc | |
| | tcgttgaaatcttcggcgacgattcctgcctcca | |
| | gtttggtggtggtaccctcggtcacccctgggt | |
| | aacgcacctggtgcaactgcaaaccgtgttgctc | |
| | tggaagcttgtgttcaagctcgtaacgaaggtcg | |
| | cagcctggcccgtgaaggtaatgatgtcctccgt | |
| | gaagcaggtaagtggtcgcctgaattggcagccg | |
| | ccctcgacctgtggaaggaaatcaagttcgaatt | |
| | cgataccgttgacactctctaagctcctgatgag | |
| | catcagtggatgggaagtttgtcacaatctacc | |
| | tattcactgatgatttcctcccatggagtttaaa | |
| | aaagttgcgaaggaaacggccatcactttgcaaa | |
| | gctatttgacctaccaagcggtgcgtctaattag |

SEQUENCES

| SEQ ID NO: | Sequence | Description |
|---|---|---|
| | tcagcagcttagtgaaaccaatcctggacaggcg | |
| | atttggctaggagagttctctaaacgtcatccaa | |
| | ttcaggaaagtgatctttacctcgaagcgatgat | |
| | gctagaaaacaaagagctcgtcctcagaatcctg | |
| | acggtgcgagaaaaccttgcggaaggagttctgg | |
| | agttttgccagaaatggtcctcagccaaatcaa | |
| | gcagtccaatggaaaccatcgccgttctttatta | |
| | gagcgtttaactcaagttgattcttcatcaactg | |
| | atcagactgaacctaaccctggtgagtctgatac | |
| | ttcagaagattctgaataaactttgatccgataa | |
| | agaggacataaatcaatgaaaactttacctaaag | |
| | aaaagcgttacgaaactctttcttacttgccccc | |
| | cctcagcgaccagcaaatcgctcgccaagtccag | |
| | tacatgatggatcaaggctatattcctggtatcg | |
| | agttcgaaaaagatccgactcctgaactccacca | |
| | ctggacactgtggaagctgccccttttcaacgca | |
| | agctctgctcaagaagtactcaacgaagtgcgtg | |
| | agtgccgtagtgaatattctgactgctacatccg | |
| | tgttgttggtttcgacaacatcaagcagtgccaa | |
| | accgttagcttcatcgtttacaagcccaaccaaa | |
| | cccgttactaaggttttgttggttttgtgacct | |
| | gaatttaatttgaatcatgcggaatgcgatcgcc | |
| | ttaggacggtcgcattttttgtttacgtctaaaa | |
| | ttagtcgaaatcccccatcaacgccatggtagtg | |
| | attttgtcttaacgttattcacccatcaatttca | |
| | aaatgaacctgaagtttcttaaatctctctgggc | |
| | tacggcggcgatcgcctttgccattagcgtaaat | |
| | ccgagccttgtctttgctgaaacggaacccccaa | |
| | gcgaaaccaaaactgccctgatcaatgaactccg | |
| | caccttaactttccgggatgaaaacgcgacccag | |
| | attttggacttgatgctgcaacagatccaagctc | |
| | aatccaccaccatgggcgatggcttttgggtga | |
| | agaaacagatcccgaaacctggccgctatccaa | |
| | gaaagtgtcacccgcatcaccgaccgcatttata | |
| | ccctgatgcaagacagaattgatttcgttgccct | |
| | ccagcgggatatcgacttcaagctctatcacgaa | |
| | tatttcaccgaagccgaactccaagatttaatca | |
| | ccttctataaaacacccaccggacaaaagactgc | |
| | cgcaacttttccagaacttacagaacgctccaca | |
| | gccctctttagtgagcagctagcccagccatga | |
| | tagaaattacccaacaggtgatgttagaagaatt | |
| | tgcctctgcctttgcaacgttcgatgctccagaa | |
| | actgaagcgcctgaaaattcggagtcggctgaag | |
| | cagaagccatcgattaaacagagttgcggatgga | |
| | tctgtgtaatcatcctgaaacttctacagatccc | |
| | gcaaattaccaaccaagataattgaattccccat | |
| | catctcatcatggcaacggacggctttcttcaga | |
| | tattgctcgcctttctcattgggaacacacaatt | |
| | tactttttttgccaaacttgagccttaatcgcgc | |
| | cagtccccatgggtgagaaagccgcactagaatg | |
| | attctagagaagtgagattcgagggaattttta | |
| | agatgaaaaacgagtgactctgacatttcccca | |
| | ggacacggtgcaaatgcccgtcacctatcgcttg | |
| | gcaaaggattttaatattgcggcgaatatcatcc | |
| | gcgcccaggtcgctccaaaccaggtgggcaagtt | |
| | ggtggtggaactccaggggatattgatgccatt | |
| | gagatggccttggaatggatgaaaggcaagggga | |
| | ttttagtttccctcgcgagcaaagaaattgtgat | |
| | taacgaagatatttgtgtggattgtggtctctgt | |
| | acaggggtttgtccgacgggagcattatcgctag | |
| | atccccaaacgtttcgactaaaatttacccgcca | |
| | aaaatgtgtggtttgcgaacagtgtttacccgct | |
| | tgtccggtccaggcgatcgccacaaattttaag | |
| | gtaccttcccaaaaaaagtgctgttggcggtga | |
| | tgaaatcaacccaaagattgcaattgttaatgag | |
| | agtgattataaattctgttgaaaaatgtatttaa | |
| | aggtagaaaccattgtgttttaagcttttgggt | |
| | ctgttttgagcaattaagaagattattctaggcc | |
| | agagcatcccttaggatattgttaggaattccta | |
| | acttttaattcttcatgaaaaaacaggccaacg | |
| | ttcagcgtcacacagagcccgcagatcagaattt | |
| | gcggctaaaaagtcatggcaattatttattta | |
| | ttggctgtggcggcgggcttgattttttacagg | |
| | gttacatgattgcgcccttaattccccgtttatc | |
| | ggagattttggcgtttctgtccaggaaattggc | |

| SEQUENCES | | |
|---|---|---|
| SEQ ID NO: | Sequence | Description |
| | tttattgtgccgatttatatgctgtcctacgctg<br>tcatggctcttttttat | |
| 10 | aattcgagcgggattttatg | Blue arrow primer pair<br>(FIG. 10C): FWD |
| 11 | gggaagcggatatcttcgag | Blue arrow primer pair<br>(FIG. 10C): REV |
| 12 | aacacgccagcactcgccgttttaaaacccagtc<br>ttggctaggggcaggctttgtggagggtcattct<br>gctaatcagattttggcaaatatccaggcgatcg<br>ccgcccagttccccaacgaatatgtccagttaat<br>cgccgttgaccccaactccaaaacacgggccgca<br>gagatcatcatccaacgccctggcaacaatgcgc<br>ctgtccagacagcaaccgcaaccagtagttttc<br>gggaggcacgaaagcagcccaagcagcaatggt<br>ttcgggggtcacagtagcgggagtctcagtgggg<br>atgtggtttctaaagtccgttcgcttttgatgca<br>aggctacaagattggaacagaacacgccgataag<br>cgccgtttccgtgttaagtcctggagtagttgtg<br>gcaccattgacagcacccaagaggcagaagtttt<br>acgtcacctcgaaggttgtctccaggagcacagt<br>ggcgaatatgtccgcatgattggtgtcgatgaag<br>cggctaaacgacgggtgcttgaggaaattatcca<br>acgcccctaggttgtgtaacgcgaccacttcgtt<br>atggggagaaaacgaatgtctatcccccaaccc<br>ttaccccacctgtgattaattgaatcaccgttga<br>cagaatcattgtgactttccaggcaattacccat<br>ccagatattcaaattagtggcgatgtaaggattc<br>atccccgtgcggttattgccccccggtgttattct<br>gcaagcaaccgaaggcaattatgtggcgatcgcc<br>actggtgcttgtattggtgcaggtgcgattatcc<br>aggcccacggcggcaacatcgagatccatgccgg<br>cgcgattatcggggcaggctgcctgatcattggc<br>caatgctcagtgggagaaaatgcctgcttaggtt<br>atggctctaccctatttcaagcggcgatcgccgc<br>cgccgcaattctcccgccccaaagcctcatcggc<br>gatccgtcccgccaagaaaccaccgcttcttacc<br>agactcaaccgccaaaacccgcgaatcaatcgac<br>aacccaaccctcgatccttggcaggcagaagat<br>acaactaaccagactgccacaaccttttcgccac<br>cagggcgatcgcccactagcagcagcaatcgtcc<br>caatgtccagcccccaccagaagcaggatcccct<br>ccaactgaaacaccaaacaccgaagtgatgccga<br>cggttccagaatcaaaggaatccctagaatcggg<br>cgaaaaaacaccagttgtcgggcaagtttatatc<br>aatcaactattaatgaccctattccctcaccaaa<br>attctctcaataccccaaatcaaccagatgagcc<br>ttagccccacaaaactttcatgattgcttgagtg<br>aaaattaaatgtttaaagttcttaaaggagattg<br>ttgagaaacataaatacttaattcatctcatttg<br>aacgctttccctctctaaagatcccgacagaaaa<br>cggttttagcccaatgtctcattaggtagcatgg<br>ctgaattcgagcgggattttatggcttttttagg<br>tattttttgtaagggtaaaataggcccatcaaaca<br>gcattagaaatgctaatcagcccaaaaaacaaaa<br>gcaatcttttttttgttgctaaaagataaaaataa<br>gtcgaggctgtggtaacatatcccacagattaaa<br>gaaagtcataagacttgaatcttcagaattttaa<br>aaagcagttttgccaacgtaagattttttgaagtt<br>ttcgaccaacaataccgttactggtatttgtctg<br>ttaaagataagcatttttgctggaggaaaaccgc<br>atggttcagaccaaatctgctgggtttaatgccg<br>gttccaacctgctgacggtgcaccagaatctgcc<br>ggcactgccggtcgatgcaaccagtgacgaagtg<br>cgcaaaaatctgatggatatgtttcgtgaccgcc<br>aagccttcagcgaacatacgtggaaaatgctgct<br>gtcggtttgccgtagctgggcggcctggtgtaaa<br>ctgaacaatcgcaaatggtttccggcagaaccgg<br>aagatgtgcgtgactatctgctgtacctgcaggc<br>acgtggtctggcagttaaaaccatccagcaacat<br>ctgggccaactgaacatgctgcaccgtcgctctg<br>gtctgccgcgtccgagtgattccaatgccgtcag<br>tctggtgatgcgtcgcattcgtaaagaaaacgtg | CRE Recombinase<br>integration into rbcLXS,<br>visible region (FIG. 4B) |

| SEQUENCES | | |
|---|---|---|
| SEQ ID NO: | Sequence | Description |
| | gatgcaggcgaacgcgctaaacaggcactggctt | |
| | ttgaacgtaccgatttcgaccaagttcgctctct | |
| | gatggaaaacagtgatcgttgccaggacatccgc | |
| | aatctggcattcctgggtattgcttataacaccc | |
| | tgctgcgcattgcagaaatcgctcgtattcgcgt | |
| | gaaagatatcagccgtacggacggcggtcgcatg | |
| | ctgattcacatcggccgtaccaaaacgctggttt | |
| | ccaccgcgggcgtcgaaaaagccctgtcactggg | |
| | tgtcacgaaactggtggaacgctggatttcagtt | |
| | tcgggcgtcgcagatgacccgaacaattacctgt | |
| | tttgtcgtgtgcgcaaaaatggtgttgcagctcc | |
| | gagcgctacctctcagctgagtacgcgtgcgctg | |
| | gaaggcatcttcgaagccacccatcgcctgattt | |
| | atggcgcgaaagatgacagcggtcagcgttacct | |
| | ggcatggtccggtcactcagctcgtgttggtgca | |
| | gcacgtgatatggcacgtgcaggtgtctctatcc | |
| | cggaaattatgcaggccggcggttggacgaacgt | |
| | gaatattgttatgaactatattcgtaacctggac | |
| | tctgaaacgggtgcgatggtgcgtctgctggaag | |
| | atggcgactgaCGAGGGCGGTGCTTTGGCAGGAT | |
| | CCGGCTGCTAACAAAGCCCGAAAGGAAGCTGAGT | |
| | TGGCTGCTGCCACCGCTGAGCAATAACTAGCATA | |
| | ACCCCTTGGGGCCTCTAAACGGGTCTTGACGGGT | |
| | TTTTTGTCTAGATCAACGGCCTCAACCTACTACT | |
| | GGGCAACAAAGCCACGTTGTGTCTCAAAATCTCT | |
| | GATGTTACATTGCACAAGATAAAAATATATCATC | |
| | ATGAACAATAAAACTGTCTGCTTACATAAACAGT | |
| | AATACAAGGGGTGTTATGAGCCATATTCAACGGG | |
| | AAACGTCTTGCTCCAGGCCGCGATTAAATTCCAA | |
| | CATGGATGCTGATTTATATGGGTATAAATGGGCT | |
| | CGCGATAATGTCGGGCAATCAGGTGCGACAATCT | |
| | ATCGATTGTATGGGAAGCCCGATGCGCCAGAGTT | |
| | GTTTCTGAAACATGGCAAAGGTAGCGTTGCCAAT | |
| | GATGTTACAGATGAGATGGTCAGACTAAACTGGC | |
| | TGACGGAATTTATGCCTCTTCCGACCATCAAGCA | |
| | TTTTATCCGTACTCCTGATGATGCATGGTTACTC | |
| | ACCACTGCGATCCCCGGGAAAACAGCATTCCAGG | |
| | TATTAGAAGAATATCCTGATTCAGGTGAAAATAT | |
| | TGTTGATGCGCTGGCAGTGTTCCTGCGCCGGTTG | |
| | CATTCGATTCCTGTTTGTAATTGTCCTTTTAACA | |
| | GCGATCGCGTATTTCGTCTCGCTCAGGCGCAATC | |
| | ACGAATGAATAACGGTTTGGTTGATGCGAGTGAT | |
| | TTTGATGACGAGCGTAATGGCTGGCCTGTTGAAC | |
| | AAGTCTGGAAAGAAATGCATAAGCTTTTGCCATT | |
| | CTCACCGGATTCAGTCGTCACTCATGGTGATTTC | |
| | TCACTTGATAACCTTATTTTTGACGAGGGGAAAT | |
| | TAATAGGTTGTATTGATGTTGGACGAGTCGGAAT | |
| | CGCAGACCGATACCAGGATCTTGCCATCCTATGG | |
| | AACTGCCTCGGTGAGTTTTCTCCTTCATTACAGA | |
| | AACGGCTTTTTCAAAAATATGGTATTGATAATCC | |
| | TGATATGAATAAATTGCAGTTTCATTTGATGCTC | |
| | GATGAGTTTTTCTAATCAGAATTGGTTAATTGGT | |
| | TGTAACACTGGCAGAGCCTCTAGTATATAAACGC | |
| | AGAAAGGCCCACCCGAAGGTGAGCCAGTGTGACT | |
| | CTAGTAGAGAGCGTTCACCGACAAACAACAGATA | |
| | AAACGAAAGGCCCAGTCTTTCGACTGAGCCTTTC | |
| | GTTTTATTTGggttttgttggttttgtgacctg | |
| | aatttaatttgaatcatgcggaatgcgatcgcct | |
| | taggacggtcgcattttttgtttacgtctaaaat | |
| | tagtcgaaatccccatcaacgccatggtagtga | |
| | ttttgtcttaacgttattcacccatcaatttcaa | |
| | aatgaacctgaagtttcttaaatctctctgggct | |
| | acggcggcgatcgcctttgccattagcgtaaatc | |
| | cgagccttgtctttgctgaaacggaaccccaag | |
| | cgaaaccaaaactgccctgatcaatgaactccgc | |
| | accttaactttccgggatgaaaacgcgacccaga | |
| | ttttggacttgatgctgcaacagatccaagctca | |
| | atccaccaccatgggcgatggcttttgggtgaa | |
| | gaaacagatcccgaaaccctggccgctatccaag | |
| | aaagtgtcacccgcatcaccgaccgcatttatac | |
| | cctgatgcaagacagaattgatttcgttgccctc | |
| | cagcgggatatcgacttcaagctctatcacgaat | |
| | atttcaccgaagccgaactccaagatttaatcac | |
| | cttctataaaacacccaccggacaaaagactgcc | |
| | gcaacttttccagaacttacagaacgctccacag | |

| SEQ ID NO: | Sequence | Description |
|---|---|---|
| | ccctctttagtgagcagctagccccagccatgat<br>agaaattacccaacaggtgatgttagaagaattt<br>gcctctgcctttgcaacgttcgatgctccagaaa<br>ctgaagcgcctgaaaattcggagtcggctgaagc<br>agaagccatcgattaaacagagttgcggatggat<br>ctgtgtaatcatcctgaaacttctacagatcccg<br>caaattaccaaccaagataattgaattccccatc<br>atctcatcatggcaacggacggctttcttcagat<br>attgctcgcctttctcattgggaacacacaattt<br>acttttttgccaaacttgagccttaatcgcgcc<br>agtccccatgggtgagaaagccgcactagaatga<br>ttctagagaagtgagattcgaggggaattttaa<br>gatgaaaaaacgagtgactctgacatttccccag<br>gacacggtgcaaatgcccgtcacctatcgcttgg<br>caaaggattttaatattgcggcgaatatcatccg<br>cgcccaggtcgctccaaaccaggtgggcaagttg<br>gtggtggaactccaggggatattgatgccattg<br>agatggccttggaatggatgaaaggcaagggat<br>tttagtttccctcgcgagcaaagaaattgtgatt<br>aacgaagatatttgtgtggattgtggtctctgta<br>caggggtttgtccgacgggagcattatcgctaga<br>tccccaaacgtttcgactaaaatttacccgccaa<br>aaatgtgtggtttgcgaacagtgtttacccgctt<br>gtccggtccaggcgatcgccacaaattttaagg<br>taccttcccaaaaaaagtgctgttggcggtgat<br>gaaatcaacccaaagattgcaattgttaatgaga<br>gtgattataaattctgttgaaaaatgtatttaaa<br>ggtagaaaccattgtgttaagcttttgggtc<br>tgttttgagcaattaagaagattattctaggcca<br>gagcatcccttaggatattgttaggaattcctaa<br>cttttaattcttcatgaaaaacaggccaacgt<br>tcagcgtcacacagagcccgcagatcagaatttg<br>cggctaaaaagtcatggcaatttatttatttat<br>tggctgtggcggcgggcttgatttttttacaggg<br>ttacatgattgcgcccttaattccccgtttatcg<br>gagattttggcgtttctgtccaggaaattggct<br>ttattgtgccgatttatatgctgtcctacgctgt<br>catggctcttttttat | |
| 13 | aattcgagcgggatttatg | Blue and black primer pairs (FIG. 10C): FWD |
| 14 | agagagcgaacttggtcgaa | Blue and black primer pairs (FIG. 10C): REV |
| 15 | gtgaatatttcaccccccattcaacttgtcgaag<br>cccccacccaagcttactgacctgggctaaggc<br>gatcgccacgggcacccccagacccatttcagcgg<br>gggcaacaactgagtcagaaattgggcgcaacct<br>atggcagtgatggcctaacccaaataggattctg<br>gattccggaggtgggcgatcgccccgtttacctc<br>gaaatttttacgcccatggaggcaatcgatttc<br>gccttgctgatcaagtcattccgttccgtcggga<br>ggtgctagaactgccgcgccaggggaatttgcc<br>tgggccgttgtggcgggtctcaaagctggcaccc<br>gtacccaagcgggatcgttttactggttgcgcag<br>tggtgaacagattatccgcgatgtctttgcccac<br>tctctgccctacggtgtgtttgcgccagccgagc<br>tgtacgacatggcgcaactggagcgcgacagggc<br>cgaccgcgactattttcaccaggaaacttgggtc<br>acaccgccccgcaatattttgcagattcatgtgg<br>gtaccgcttcccccacgggcaccctagccggact<br>cagccgcatttaccgtgacctcgcccgcaaattg<br>gccaatagccaaccccctcaccgccgctgaaaaaa<br>actatgtgggctttgatgcgattgaactgttacc<br>cattgaacccacggtggaatttcgccccgccgaa<br>aatgaaatgattcatgcttttggcaaattcggg<br>cgatcaccaaccaagaagtgcaagtccacctgaa<br>aaaaccagacacccaaaattggggctatgacgat<br>ctgattttaggggccgcggccaccagtcccgccc<br>tcctcagtaccctcagacccaccgaagttgtgga<br>ttttattgccacgctccacactgcctttgcccgc<br>ccgatccagattattttgacctggtttatgggc<br>atatccatcaccaagccctgggattaatcaatgc<br>gcgattttccggggcgcaaatatgtatggccat | Δglp:loxP (+CRE recombinase) visible region FIG. 6C |

| SEQ ID NO: | Sequence | Description |
|---|---|---|
| | gatacaaaccagcaaaatccgatggtgcgggctg | |
| | ttctcctggagttgcaacggcgaaaaattaatct | |
| | aggggccgatgggattcgggtggatgggggtcaa | |
| | gattttcaggtgtccgacgccatttccggccaac | |
| | tagactatgacaatgatttcctgctgaagatggc | |
| | tgcggtaccccaaaccgttggtacagcgactcgc | |
| | gagttgtacaccatttatgaagatggccgcccct | |
| | ggcccaatgtcggttgggaagatatggctaccca | |
| | tttggatttaatttacctaaagcccgattgtttt | |
| | cagtggagtccgttgatcttcgagcataatacgc | |
| | ccacgttacagggattttggcaacgggaatggcg | |
| | ggatgtgtgcaaaattatggcccatggcgatcgc | |
| | tgggtgaccggttgcgccaaccatgacacggtac | |
| | gcaagggcaaccacatcaacaccgccgcaattcg | |
| | gattaatgaatatttaggggattctttgccggaa | |
| | attttacaaaatgcctacgataatccagcaaccc | |
| | aactgtggatccatggctttagcccaggaattcc | |
| | gatggattttttaaatgcattaatgcacactccc | |
| | tggggcttttttcggaatacagatgaccaatatg | |
| | ccgtcaaaattatggcggacgaaattggctttct | |
| | ctattggcaaattacgccggaaatttaccgacaa | |
| | tcctgggcgtttcggcggtttaaaaccatgggct | |
| | tttatgatctctcgttaatgcggcagttctttaa | |
| | ggcagtggaacaggccattgaagcgattggctat | |
| | gatctaccaaagctggcgattttctgcaaaccg | |
| | aattagaaccacaatttgatttttaaagccgat | |
| | taccattgccaacctgaaggaaatagcgatcgcc | |
| | tttatggaggatggccacgaggcttgtcgggtct | |
| | cccattattgtggatcggtaccggatgagcgggc | |
| | gagctttaatttacgcttgcggcaatatcgccag | |
| | gcccagccttggctgcgaaatcatctcgatcctg | |
| | caaggggcgatcgcctgcaccattggtcggatca | |
| | ccaacgcaccattttctacggcaggcgcaccaat | |
| | cccgacacccagcagcggcttgtgttagtggcgc | |
| | acatgccggggctccgaagaccgttgagattgg | |
| | caaatggctcgccctggatttggatcgttggcag | |
| | ttggcgatcgccacaccgactttgaagatcaaca | |
| | ccatctatgacttagcccaaattcacttgcacaa | |
| | tggcgaaggttttctgttatctgaaattcctccc | |
| | taaatgatgtcttttgagcctaaaaacacacttt | |
| | tttgacctaatttaacccataacttcgtataATG | |
| | TATGCtatacgaagttatcccctcttgcctaca | |
| | gcatctcccccaggggagaattcttcctgtttca | |
| | actccctctaacgtaaacccattgaatttaaaaa | |
| | agactttatgactgctttactgctccatgaccaa | |
| | cattattcccttgatcatgaagcctttctctcaa | |
| | ccctcagcaacacagaaaatttactcattattca | |
| | agatctagatggcgtttgcatggggttagtcaaa | |
| | gacccctttaacccgcaaaattgatcctgactata | |
| | tccgcgccacacgcaagtttagagaccacttctt | |
| | tgtcctcaccaacggtgaacatgaaggcagaagg | |
| | ggagtaaatcgcatcgttgaacgggcatttcgca | |
| | atgttgaagccaaagaggaaacaagctatttacc | |
| | tggtttagcagcaggggtgtgcaatggcagaca | |
| | gataatggccaaatttcccatcccggtgttagcc | |
| | aagcagaactcgatttccttgccacagtgccaga | |
| | tttaattggtcaaagtttaggacaattttttact | |
| | aaatatgttgatattttcccgctgagcttcaac | |
| | ctgagctgatccatgcttctgttttagataatct | |
| | cgtttcaccgacggcaaatttaaacgtcctggcc | |
| | gaatatttaggcgatcgccttgagatttaccaag | |
| | acctccagcgcaccatggaaaccctgatgaatga | |
| | tttgctagaaaaagctggccaacagggtttagac | |
| | aatagttttttcgtgcactatgcgcccaatttag | |
| | gcagagataatgtggggaaagaaattgtccgctt | |
| | tgccacagccaaggattctggcaccacagatttt | |
| | cagtttatggtgtgtggtgccgtcaaagaagcgg | |
| | gggttttagtgctgctgaattattactatgccca | |
| | acgcacgggccactatcccctaggagaaaacctt | |
| | aacgcccgccaagcgccccaaaaccacgaggaac | |
| | tattgcaactggtgcaagacaatttcgatccgca | |
| | attgatgcctttaatcgttggcgtcggcgatacg | |
| | gtcacaagtcacaccgaaggcgatcaagttcgac | |
| | gggggggagcgatcgcctattcctgcagctcgt | |
| | ccaagacattggtaaatgggcaaagagcggcaat | |

| SEQUENCES | | |
|---|---|---|
| SEQ ID NO: | Sequence | Description |
| | ctcgtcgtgtatatcgacagctcccagggagaat<br>taaaaaatcggattcccttaaaactggggacaat<br>caatggtcaaacccaagtgattgagggcattact<br>gatccggctgatccgttacaaattaacgttgctt<br>ttccgggcgggtttgaacaatacaccgccctttt<br>tcagcaggccgccgcaaaccgatctggaacatag | |
| 16 | catctcgatcctgcaaggg | FIG. 6A-6C black arrow primer pair: FWD |
| 17 | ttgtttcctctttggcttcaa | FIG. 6A-6C black arrow primer pair: REV |
| 18 | atgagcgatcgccccatagaaaaaaccctcgccg<br>aaaaggctcctgctagttacgaatgccccagctg<br>cggttacatttacaccsctgcaaagggagaaagc<br>cgtaccaacacgccaccgggtacagcctttgaag<br>atctgcccctcatttggaactgtcctgtttgtag<br>cgttgatcgcgcccaatttcgcaatattggtgca<br>gcggatgcccctcaggttttgaagaaaatctga<br>aatatggttttggcgtgaataacctcagctccaa<br>ccaaaaaaacctactcattttttggagccatgggc<br>ttggcaatccttttcttcctgagcctttatggtc<br>tggactaaagaccccatagcaaagccttgtctt<br>aattccaaattttttacttttattgcttttatatt<br>gcgctatgacttcagttttaggtctattaaaacc<br>cttaaaaaaagccattgcggcgatcgccgttttg<br>gtattgtgcatcggctgtgtccaggcaccaacca<br>ttagcgaaaatccctggcaagaaatcgacttaaa<br>taccgattcgacctttgccaatattgcttttacc<br>gacgacctccaacatggctggcttgtcggtacca<br>aagaaaccctctttgaaactaccgatggcggcaa<br>aacctgggccgagcgagttattgatctcggtgac<br>gaaaaagaaagttttaccggtgttagcttctctg<br>gccaagaaggctggattaccggacggccttcgat<br>cctgctccacaccgacgatggtggtgagcactgg<br>agtcgcatcgccctcagcagtcaattgcccggtg<br>ccccctacaacatcaccgccctagggccgaacac<br>cgccgaaatggtcaccgatcttggggccatttac<br>aaaaccaccgacggcggcaaaaactggaaagccc<br>ttgtcgaaggtgccgttggcgttgcccgcaccat<br>tgaacgttctgccgatggtaaatatgtggccgtt<br>tctgcccgggtaattttatccacttggtcgc<br>ctggggacacagaatggacgccccataaccggaa<br>ttcttcccgtcgcctccaaagcatgggctttaat<br>ggcgaagataagctctggttgttagcccgtgggg<br>gagttgtgcaatttagcgacgatacaaatccaga<br>caatgcagaagcctggagcgaaccagtgacaccg<br>cagtaccgcaacagtgttggtttgttgcacattg<br>gctatcgtaccccccgcagaactatgggccgtcgg<br>tggtagtggcagtgttgttgtgagtaaagatggt<br>ggcgacacttggttccgggacgctgccctagaag<br>agatcccgacaaacttttaccgagtcgttttctt<br>aaatgagaataaaggcttcatccttgggcaacag<br>ggggtgattttacggtacgatacatccacggaag<br>cggcctaagggcaacccattctattgtgggagtg<br>tctgttaattccgtatgatataggctaatttgtt<br>taataagtttttttttcattaacaattgagaggag<br>aatagtcgcatggcaggttctaccggagaacgcc<br>cgttttctgacattgtgaccagtattcgctactg<br>ggttattcacagcatcaccattccgatgttattt<br>attgctggctggctctttgtgagcactggcttgg<br>cttacgatactttcgggacaccccgtcctgacca<br>atactttactgaaactcgtcaagagattcccatt<br>gtgactgatcgttacaaagcgattgatcagatca<br>atgagtttaacaattaagtaacgcgcgttttttct<br>ttgctgtattcactaaaaggttttgtattatgac<br>aagcggtcctaaccaacctgtttcttatccaatt<br>tttaccgtccgttggttggcggtgcacaccctgg<br>ctgtaccctcggttttcttcctaggggcgatcgc<br>cgctatgcagtttattcaacgttaggagcttccg<br>atggaaagaaatcaaaatcccaacagacagcctg<br>tggaactaaaccggacttctctatatctgggttt<br>acttctaatcgctgtgctcggtattctatttttcc<br>agctacttctttaactaagctggcagcccttttaa | psbEFLJ locus wt 7002, visible region FIG. 15 |

| SEQ ID NO: | Sequence | Description |
|---|---|---|
| | tttcagcccttttaatttatttttttcggaggttg
ttctcatgtctgaaggcggaaaaatccccactttg
gatcgttgcagttgtcgctggtatgggcgtcatt
gcggttgtcggtatctttttctacggtgcatatg
caggggtaggctctgcggtttagatgcacaattc
gctctaattaattgttgagacaccacctgctcta
attgagggtgggtttttgttttaggaacttctggg
gcaatagggagtccaaaaaagtttggggataatc
gtcaacggtgcagtatgactatgaaaagacagtt
gcgggatctgaaagtatgggtgatggtgggtctg
ttgagtttaggtggagcctggggtcaaagggcga
tcgccgctgaaaccctccgactaaaattagggcc
acttcaacaaactttacaattagaagatttagaa
acctttgccgaaacgggtcaagtcccccgcaacc
tccgaccctatggggtatttttggatggtaattt
gcagaaattctccaacgacgcttgcagatcgag
ccagagatggcggatcagtttttttgatcagttgt
ggcgatcgcctacgggaaaacagattttggcgca
aattcaaacggccctaccgggaacttctattcag
gatctccaggcgacggtggatttggcgttaggtc
agggagtagaaatcagcgccctgaatttgttgca
ggcttaccccaagcaggaactgactattgatctt
acggcggtggctggcctcttgttacaactcaatt
taccgaatatccagaatcaactcctcgcgccgag
ggtgactgaagccctcgaaagtacagaaccgcag
atttttcaacgctcaaacctcaaccccacagccc
ccggcccccaaacggtgcggcgtcaaagcttaat
tctgcaagatgcaaagcgcgatcgcaccattccc
attgatatttttgatagtccccaatcccagtctc
agctagtggttttgtcccatgggtttgcggccaa
ccgtcatttctcgattatcggcggtgcatctg
gcctccatggttacaccgtcgttaccctcgatc
accccggcagtaatattcagtctctgtttaatcc
gggcttaaatcttgatactttgctcccggcgacg
gaatttgtcgatcggcccaaggatattcaatttg
tgctggatcaactggagcgcctcaaccaggatca
aaccctcacaaccgctttgccacggacaatgtg
acggtaattggccattccttcggaggttacacgg
ccttggcgatcgccgaggaattgtcgatcccat
tgctatccgtgctcactgccagcgggcaacccct
ttaaccagagcaccggggactggctccaatgtg
cagcggcgaaactccccctatgaccagttaaattt
gcgggatgaacgggtcaaacaggcgatcgccctc
aatccctcagcgatcaaatctttggggagcagg
gtttagaaaaaattaaaattccgaccttgatcgt
tgctagtacaaaggataccgtcacccccaagcttg
gcccaccagttgaaaccgttccagcagttgggcg
gcgaaaaatatctcgtcgtcgccgacggtgcaac
ccacatgagcgtcactgatgttagcaatcgcgat
agcgccttggcccaaagtacccttgtcccggagg
tgatgggcaacgcggcagaaccagtccgacaaat
ggtacgagggtaagcttaagctttctggcgcgc
caccaaaccggaggacaaaattaccagcaatttc
tcacgggggcctatgtgcaatctctttcccaggg
ggcgattaagctacgcctcacggaaacgatttct
ccagagttagaacgattcctgagtcgcttacccc
aggctcccaattctgccgaagtggcgacaccgac
tcaacaggctgctttttttgaatatggggcgatcg
ccaaacccaaccccccaaccgcacctatccccagg
gcgttctcacggaaagccttaagcccttgatgac
gaacttggaatcggaaacttttctcgcaataaag
ccggataattttgatgtcttgtatcaaaaacct
ga | |
| 19 | tttctgacattgtgaccagtattc | Purple primer pair set: FWD. FIG. 15 |
| 20 | cggaagctcctaacgttgaat | Purple primer pair set: REV. FIG. 15 |
| 21 | gccccataaccggaattcttcccgtcgcctccaa
agcatgggctttaatggcgaagataagctctggt
tgttagcccgtggggagttgtgcaatttagcga
cgatacaaatccagacaatgcagaagcctggagc
gaaccagtgacaccgcagtaccgcaacagtgttg | CRE recombinase integration into psbEFLJ locus, visible region. FIG. 15 |

| SEQ ID NO: | Sequence | Description |
|---|---|---|
| | gtttgttgcacattggctatcgtaccccgcaga | |
| | actatgggccgtcggtggtagtggcagtgttgtt | |
| | gtgagtaaagatggtggcgacacttggttccggg | |
| | acgctgccctagaagagatcccgacaaactttta | |
| | ccgagtcgttttcttaaatgagaataaaggcttc | |
| | atccttgggcaacaggggggtgattttacggtacg | |
| | atacatccacggaagcggcctaagggcaacccat | |
| | tctattgtgggagtgtctgttaattccgtatgat | |
| | ataggctaatttgtttaataagttttttttcatt | |
| | aacaattgagaggagaatagtcgcccccacaaaa | |
| | cttcatgattgcttgagtgaaaattaaatgttt | |
| | aaagttcttaaaggagattgttgagaaacataaa | |
| | tacttaattcatctcatttgaacgctttccctct | |
| | ctaaagatcccgacagaaaacggttttagcccaa | |
| | tgtctcattaggtagcatggctgaattcgagcgg | |
| | gattttatggcttttttaggtatttttgtaaggg | |
| | taaaataggcccatcaaacagcattagaaatgct | |
| | aatcagcccaaaaaacaaaagcaatctttttttg | |
| | ttgctaaaagataaaaataagtcgaggctgtggt | |
| | aacatatcccacagattaaagaaagtcataagac | |
| | ttgaatcttcagaattttaaaaagcagttttgcc | |
| | aacgtaagattttttgaagttttcgaccaacaata | |
| | ccgttactggtatttgtctgttaaagataagcat | |
| | ttttgctggaggaaaaccgcatggttcagaccaa | |
| | atctgctgggtttaatgccggttccaacctgctg | |
| | acggtgcaccagaatctgccggcactgccggtcg | |
| | atgcaaccagtgacgaagtgcgcaaaaatctgat | |
| | ggatatgtttcgtgaccgccaagccttcagcgaa | |
| | catacgtggaaaatgctgctgtcggtttgccgta | |
| | gctgggcggcctggtgtaaactgaacaatcgcaa | |
| | atggtttccggcagaaccggaagatgtgcgtgac | |
| | tatctgctgtacctgcaggcacgtggtctggcag | |
| | ttaaaaccatccagcaacatctgggccaactgaa | |
| | catgctgcaccgtcgctctggtctgccgcgtccg | |
| | agtgattccaatgccgtcagtctggtgatgcgtc | |
| | gcattcgtaaagaaaacgtggatgcaggcgaacg | |
| | cgctaaacaggcactggcttttgaacgtaccgat | |
| | ttcgaccaagttcgctctctgatggaaaacagtg | |
| | atcgttgccaggacatccgcaatctggcattcct | |
| | gggtattgcttataacaccctgctgcgcattgca | |
| | gaaatcgctcgtattcgcgtgaaagatatcagcc | |
| | gtacgacggcggtcgcatgctgattcacatcgg | |
| | ccgtaccaaaacgctggtttccaccgcgggcgtc | |
| | gaaaaagccctgtcactgggtgtcacgaaactgg | |
| | tggaacgctggatttcagtttcgggcgtcgcaga | |
| | tgacccgaacaattacctgttttgtcgtgtgcgc | |
| | aaaaaatggtgttgcagctccgagcgctacctctc | |
| | agctgagtacgcgtgcgctggaaggcatcttcga | |
| | agccacccatcgccgatttatggcgcgaaagat | |
| | gacagcggtcagcgttacctggcatggtccggtc | |
| | actcagctcgtgttggtgcagcacgtgatatggc | |
| | acgtgcaggtgtctctatcccggaaattatgcag | |
| | gccggcggttggacgaacgtgaatattgttatga | |
| | actatattcgtaacctggactctgaaacgggtgc | |
| | gatggtgcgtctgctggaagatggcgactgaCGA | |
| | GGGCGGTGCTTTGGCAGGATCCGGCTGCTAACAA | |
| | AGCCCGAAAGGAAGCTGAGTTGGCTGCTGCCACC | |
| | GCTGAGCAATAACTAGCATAACCCCTTGGGGCCT | |
| | CTAAACGGGTCTTGACGGGTTTTTTGTCTAGATC | |
| | AACGGCCTCAACCTACTACTGGGGTTGACAATTA | |
| | ATCATCGGCATAGTATATCGGCATAGTATAATAC | |
| | GACAAGGTGAGGAACTAAACCATGaagctgacca | |
| | gcgccgttccggtgctcaccgcgcgcgacgtcgc | |
| | cggagcggtcgagttctggaccgaccggctcggg | |
| | ttctcccgggacttcgtggaggacgacttcgccg | |
| | gtgtggtccgggacgacgtgaccctgttcatcag | |
| | cgcggtccaggaccaggtggtgccggacaacacc | |
| | ctggcctgggtgtgggtgcgcggcctggacgagc | |
| | tgtacgccgagtggtcggaggtcgtgtccacgaa | |
| | cttccgggacgcctccgggccggccatgaccgag | |
| | atcggcgagcagccgtggggcgggagttcgccc | |
| | tgcgcgacccggccggcaactgcgtgcacttcgt | |
| | ggccgaggagcaggactaaccgacgtcgacccac | |
| | tctagaggatccccgctccgtgtaaatggaggcg | |
| | ctcgttgatctgagccttgcccctgacgaacgg | |

SEQUENCES

| SEQ ID NO: | Sequence | Description |
|---|---|---|
| | cggtggatggaagatactgctctcaagtgctgaa<br>gcggtagcttagctcccgtttcgtgctgatcag<br>tcttttcaacacgtaaaaagcggaggagttttg<br>caattttgttggttgtaacgatcctccgttgcaa<br>ttgatgcacaattcgctctaattaattgttgaga<br>caccacctgctctaattgaggggtggttttgttt<br>taggaacttctggggcaatagggagtccaaaaaa<br>gtttggggataatcgtcaacggtgcagtatgact<br>atgaaaagacagttgcgggatctgaaagtatggg<br>tgatggtgggtctgttgagtttaggtggagcctg<br>gggtcaaagggcgatcgccgctgaaaccctccga<br>ctaaaattagggccacttcaacaaactttacaat<br>tagaagatttagaaacctttgccgaaacgggtca<br>agtcccccgcaacctccgaccctatgggtattt<br>ttggatggtaatttgcagaaatttctccaacgac<br>gcttgcagatcgagccagagatggcggatcagtt<br>ttttgatcagttgtggcgatcgcctacgggaaaa<br>cagattttggcgcaaattcaaacggccctaccgg<br>gaacttctattcaggatctccaggcga | |
| 22 | aattcgagcgggatttttatg | Blue and black primer pairs: FWD. FIG. 15 |
| 23 | agagagcgaacttggtcgaa | Blue and black primer pairs: REV. FIG. 15 |

---

What is claimed is:

1. A system for genetically modifying a nucleic acid sequence of interest in a Cyanobacterium, the system comprising a first nucleic acid construct comprising:
   a. a nucleic acid modification system comprising a Cre-Lox system;
   b. a first antibiotic resistance reporter gene; and
   c. regions of homology to a first locus in an essential nucleic acid sequence in the organism flanking the nucleic acid modification system and the first reporter gene for integration of the first nucleic acid construct into the locus, wherein the Cyanobacterium is selected from *Synechocystis* species and *Synechococcus* species.

2. The system of claim 1, wherein the nucleic acid modification system is a modular modification system further comprising one or more nucleic acid constructs encoding a nucleic acid sequence comprising one or more components of the modification system, wherein the one or more components comprises:
   a. a second antibiotic resistance reporter gene; and
   b. recombination recognition sequences of the Cre-Lox system flanking the second reporter gene or flanking the second reporter gene and the nucleic acid sequence selected from a native sequence, a heterologous sequence, an insertion sequence, and a substitution sequence;
   c. regions of homology to a second locus in a neutral integration site (NIS), the second locus flanking the nucleic acid sequence and the second reporter gene for integration of the second nucleic acid construct into the second locus.

3. The system of claim 2, wherein the nucleic acid modification system comprising two nucleic acid constructs.

4. The system of claim 3, wherein the first construct, the second construct, or both are plasmid-free.

5. The system of claim 1, wherein the cyanobacterium is *Synechococcus* species.

6. The system of claim 2, wherein the NIS is the glpK gene.

7. The system of claim 1, wherein the essential nucleic acid sequence is selected from a rbcLXS operon and a psbEFLJ operon.

8. The system of claim 1, wherein the first reporter is a kanamycin resistance gene or a zeocin resistance gene.

9. The system of claim 2, wherein the second reporter is a gentamycin resistance gene.

10. The system of claim 1, wherein the cyanobacterium is *Synechocystis* species.

* * * * *